United States Patent
Yanowitz et al.

(10) Patent No.: US 12,087,422 B2
(45) Date of Patent: Sep. 10, 2024

(54) IDENTIFYING DISCREPANCIES BETWEEN EVENTS FROM DISPARATE SYSTEMS

(71) Applicant: Bluesight, Inc., Alexandria, VA (US)

(72) Inventors: Jeremy Ian Yanowitz, Washington, DC (US); Eric Russell Brody, Reston, VA (US); Christian Lee Doyle, Silver Spring, MD (US); Michael Christopher Wimpee, Washington, DC (US); Ramsey Richard Chambers, Reston, VA (US); Cameron James Alexander Ferroni, Washington, DC (US); Hannah Margaret Holtzman, Washington, DC (US); Ross Andrew Reed, Washington, DC (US); Matthew Jordan Kirk, Kenmore, WA (US); Lukas Nagel, Washington, DC (US)

(73) Assignee: BLUESIGHT, INC., Alexandria, VA (US)

( * ) Notice: Subject to any disclaimer, the term of this patent is extended or adjusted under 35 U.S.C. 154(b) by 0 days.

(21) Appl. No.: 18/301,934

(22) Filed: Apr. 17, 2023

(65) Prior Publication Data

US 2024/0029852 A1     Jan. 25, 2024

Related U.S. Application Data

(63) Continuation of application No. 17/807,689, filed on Jun. 17, 2022, now Pat. No. 11,664,105, which is a
(Continued)

(51) Int. Cl.
*G16H 20/13*     (2018.01)
*G06F 9/54*     (2006.01)
(Continued)

(52) U.S. Cl.
CPC ............. *G16H 20/13* (2018.01); *G06F 9/547* (2013.01); *G06F 11/3438* (2013.01);
(Continued)

(58) Field of Classification Search
CPC ........ G16H 20/13; G16H 40/20; G16H 40/60; G16H 50/30; G06F 16/9535;
(Continued)

(56) References Cited

U.S. PATENT DOCUMENTS 4,884,827 A    12/1989   Kelley
4,961,533 A    10/1990   Teller et al.
(Continued)

FOREIGN PATENT DOCUMENTS

CA    2 722 328    10/2009
CA    2 790 220    6/2013
(Continued)

OTHER PUBLICATIONS

"AmerisourceBergen Specialty Group Reconfigures Cubixx Medical Cabinet", Jan. 9, 2011, pp. 2, <https://web.archive.org/web/20180620192642/http://pharmaceuticalcommerce.com/supply-chain-logistics/amerisourcebergen-specialty-group-reconfigures-cubixx-medical-cabinet/>.
(Continued)

*Primary Examiner* — Michael Tomaszewski
(74) *Attorney, Agent, or Firm* — Knobbe Martens Olson & Bear LLP

(57) ABSTRACT

A system and method for determining event discrepancies between disparate systems is described. The system can receive sets of events from multiple systems. The system can normalize the sets of events to convert them into normalized events. From a normalized set of events, the system can concurrently generate a plurality of event arrays. The system
(Continued)

can apply one or more rules to the event arrays to generate at least one event array parameter.

20 Claims, 16 Drawing Sheets

Related U.S. Application Data continuation of application No. 16/121,155, filed on Sep. 4, 2018, now abandoned.

(60) Provisional application No. 62/554,145, filed on Sep. 5, 2017, provisional application No. 62/553,675, filed on Sep. 1, 2017, provisional application No. 62/553,641, filed on Sep. 1, 2017.

(51) Int. Cl.
| | |
|---|---|
| *G06F 11/34* | (2006.01) |
| *G06F 16/9535* | (2019.01) |
| *G06F 16/955* | (2019.01) |
| *G06K 19/07* | (2006.01) |
| *G16H 40/20* | (2018.01) |
| *G16H 40/60* | (2018.01) |
| G06K 19/06 | (2006.01) |
| G16H 50/30 | (2018.01) |

(52) U.S. Cl.
CPC ...... *G06F 16/9535* (2019.01); *G06F 16/9554* (2019.01); *G06K 19/0723* (2013.01); *G16H 40/20* (2018.01); *G16H 40/60* (2018.01); G06K 2019/06253 (2013.01); G16H 50/30 (2018.01)

(58) Field of Classification Search
CPC .. G06F 16/9554; G06F 9/547; G06F 11/3438; G06K 19/0723; G06K 2019/06253
USPC ........................................................ 705/2–3
See application file for complete search history.

(56) References Cited

U.S. PATENT DOCUMENTS

| | | | |
|---|---|---|---|
| 5,713,485 | A | 2/1998 | Liff et al. |
| 5,930,145 | A | 7/1999 | Yuyama et al. |
| 5,963,134 | A | 10/1999 | Bowers et al. |
| 5,986,662 | A | 11/1999 | Argiro et al. |
| 6,112,502 | A | 9/2000 | Frederick et al. |
| 6,249,299 | B1 | 6/2001 | Tainer |
| 6,275,157 | B1 | 8/2001 | Mays et al. |
| 6,294,999 | B1 | 9/2001 | Yarin et al. |
| 6,330,351 | B1 | 12/2001 | Yasunaga |
| 6,574,166 | B2 | 6/2003 | Niemiec |
| 6,632,619 | B1 | 10/2003 | Harrison et al. |
| 6,771,369 | B2 | 8/2004 | Rzasa et al. |
| 6,825,864 | B2 | 11/2004 | Botten et al. |
| 6,842,736 | B1* | 1/2005 | Brzozowski ........... G06Q 10/10 705/2 |
| 6,847,861 | B2 | 1/2005 | Lunak et al. |
| 6,851,615 | B2 | 2/2005 | Jones |
| 6,861,954 | B2 | 3/2005 | Levin |
| 6,877,658 | B2 | 4/2005 | Raistrick et al. |
| 6,879,876 | B2 | 4/2005 | O'Dougherty et al. |
| 6,900,021 | B1 | 5/2005 | Harrison et al. |
| 6,933,849 | B2 | 8/2005 | Sawyer |
| 6,935,560 | B2 | 8/2005 | Andreasson et al. |
| 6,952,681 | B2 | 10/2005 | McQuade et al. |
| 6,985,870 | B2 | 1/2006 | Martucci et al. |
| 6,992,574 | B2 | 1/2006 | Aupperle et al. |
| 6,994,249 | B2 | 2/2006 | Peterka et al. |
| 7,036,729 | B2 | 5/2006 | Chung |
| 7,061,831 | B2 | 6/2006 | De La Huerga |
| 7,111,780 | B2 | 9/2006 | Broussard et al. |
| 7,116,343 | B2 | 10/2006 | Botten et al. |
| 7,118,029 | B2 | 10/2006 | Nycz et al. |
| 7,140,542 | B2 | 11/2006 | Andreasson et al. |
| 7,146,247 | B2 | 12/2006 | Kirsch et al. |
| 7,151,456 | B2 | 12/2006 | Godfrey |
| 7,158,030 | B2 | 1/2007 | Chung |
| 7,165,077 | B2 | 1/2007 | Kalies |
| 7,175,081 | B2 | 2/2007 | Andreasson et al. |
| 7,177,721 | B2 | 2/2007 | Kirsch et al. |
| 7,178,729 | B2 | 2/2007 | Shaffer et al. |
| 7,182,256 | B2 | 2/2007 | Andreasson et al. |
| 7,212,100 | B2 | 5/2007 | Terenna |
| 7,212,127 | B2 | 5/2007 | Jacober et al. |
| 7,227,469 | B2 | 6/2007 | Varner et al. |
| 7,232,066 | B2 | 6/2007 | Andreasson et al. |
| 7,253,736 | B2 | 8/2007 | Tethrake et al. |
| 7,256,699 | B2 | 8/2007 | Tethrake et al. |
| 7,263,501 | B2 | 8/2007 | Tirinato et al. |
| 7,264,323 | B2 | 9/2007 | Tainer et al. |
| 7,268,684 | B2 | 9/2007 | Tethrake et al. |
| 7,275,645 | B2 | 10/2007 | Mallett et al. |
| 7,299,981 | B2 | 11/2007 | Hickle et al. |
| 7,316,231 | B2 | 1/2008 | Hickle |
| 7,317,393 | B2 | 1/2008 | Maloney |
| 7,318,529 | B2 | 1/2008 | Mallett et al. |
| 7,339,550 | B2 | 3/2008 | Hayama et al. |
| 7,341,147 | B2 | 3/2008 | Mallett et al. |
| 7,348,884 | B2 | 3/2008 | Higham |
| 7,354,884 | B2 | 4/2008 | Hada et al. |
| 7,362,228 | B2 | 4/2008 | Nycz et al. |
| 7,375,737 | B2 | 5/2008 | Botten et al. |
| 7,394,383 | B2 | 7/2008 | Hager et al. |
| 7,440,818 | B2 | 10/2008 | Handfield et al. |
| 7,446,747 | B2 | 11/2008 | Youngblood et al. |
| 7,454,880 | B1 | 11/2008 | Austin et al. |
| 7,486,188 | B2 | 2/2009 | Van Alstyne |
| 7,492,257 | B2 | 2/2009 | Tethrake et al. |
| 7,492,261 | B2 | 2/2009 | Cambre et al. |
| 7,504,954 | B2 | 3/2009 | Spaeder |
| 7,518,502 | B2 | 4/2009 | Austin et al. |
| 7,518,516 | B2 | 4/2009 | Azevedo et al. |
| 7,551,089 | B2 | 6/2009 | Sawyer |
| 7,559,483 | B2 | 7/2009 | Hickle et al. |
| 7,564,364 | B2 | 7/2009 | Zweig |
| 7,630,791 | B2 | 12/2009 | Nguyen et al. |
| 7,639,136 | B1 | 12/2009 | Wass et al. |
| 7,644,016 | B2 | 1/2010 | Nycz et al. |
| 7,672,872 | B2 | 3/2010 | Shanton |
| 7,706,915 | B2 | 4/2010 | Mohapatra et al. |
| 7,706,916 | B2 | 4/2010 | Hilton |
| 7,712,670 | B2 | 5/2010 | Sauerwein, Jr. et al. |
| 7,715,277 | B2 | 5/2010 | De La Huerga |
| 7,729,597 | B2 | 6/2010 | Wright et al. |
| 7,734,157 | B2 | 6/2010 | Wright et al. |
| 7,737,858 | B2 | 6/2010 | Matityaho |
| 7,747,477 | B1 | 6/2010 | Louie et al. |
| 7,752,085 | B2 | 7/2010 | Monroe |
| 7,772,964 | B2 | 8/2010 | Tethrake et al. |
| 7,775,056 | B2 | 8/2010 | Lowenstein |
| 7,783,163 | B2 | 8/2010 | Wright et al. |
| 7,783,174 | B2 | 8/2010 | Wright et al. |
| 7,801,422 | B2 | 9/2010 | Wright et al. |
| 7,815,117 | B2 | 10/2010 | Tuschel et al. |
| 7,834,765 | B2 | 11/2010 | Sawyer |
| 7,834,766 | B2 | 11/2010 | Sawyer |
| 7,837,093 | B1 | 11/2010 | Leu et al. |
| 7,837,107 | B1 | 11/2010 | Leu et al. |
| 7,858,841 | B2 | 12/2010 | Krautkramer et al. |
| 7,860,730 | B1 | 12/2010 | Goodall et al. |
| 7,868,754 | B2 | 1/2011 | Salvat, Jr. |
| 7,893,876 | B2 | 2/2011 | Brown et al. |
| 7,908,030 | B2 | 3/2011 | Handfield et al. |
| 7,918,830 | B2 | 4/2011 | Langan et al. |
| 7,928,844 | B2 | 4/2011 | Mackenzie et al. |
| 7,933,033 | B2 | 4/2011 | Ohishi et al. |
| 7,976,508 | B2 | 7/2011 | Hoag |
| 7,985,711 | B2 | 7/2011 | Tohmatsu et al. |
| 7,990,272 | B2 | 8/2011 | Wass et al. |
| 7,996,286 | B2 | 8/2011 | Kreiner et al. |

(56) References Cited

U.S. PATENT DOCUMENTS

| | | |
|---|---|---|
| 8,002,174 B2 | 8/2011 | Coyne, III et al. |
| 8,006,903 B2 | 8/2011 | Braun et al. |
| 8,009,913 B2 | 8/2011 | Greyshock |
| 8,019,471 B2 | 9/2011 | Bogash et al. |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |
| 8,065,858 B2 | 11/2011 | Leu et al. |
| 8,072,635 B2 | 12/2011 | Roberts et al. |
| 8,077,041 B2 | 12/2011 | Stern et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,600,548 B2 | 12/2013 | Bossi et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,838,215 B2 | 9/2014 | John et al. |
| 8,868,616 B1 | 10/2014 | Otto et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnakar |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 9,058,435 B2 | 6/2015 | Keefe et al. |
| 9,171,280 B2 | 10/2015 | Gitchell et al. |
| 9,189,769 B2 | 11/2015 | Caputo et al. |
| 9,367,665 B2 | 6/2016 | MacDonald et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 | 2/2019 | Caputo et al. |
| 10,600,513 B2 | 3/2020 | Gitchell et al. |
| 10,609,845 B2 | 3/2020 | Elizondo, II |
| 10,621,394 B2 | 4/2020 | Hussain et al. |
| 10,643,743 B2 | 5/2020 | Caputo et al. |
| 10,658,077 B2 | 5/2020 | Hussain et al. |
| 10,658,078 B2 | 5/2020 | Caputo et al. |
| 10,664,740 B2 | 5/2020 | Elizondo, II |
| 10,853,380 B1 * | 12/2020 | Agnew ............... G06F 16/2428 |
| 10,930,393 B2 | 2/2021 | Gitchell et al. |
| 11,017,352 B2 | 5/2021 | MacDonald et al. |
| 11,037,342 B1 * | 6/2021 | Agnew ............... G06F 3/04847 |
| 11,139,075 B2 | 10/2021 | MacDonald et al. |
| 11,551,797 B2 | 1/2023 | Kress-Spatz et al. |
| 11,557,393 B2 | 1/2023 | Gitchell et al. |
| 11,664,105 B2 | 5/2023 | Yanowitz et al. |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0158507 A1 | 8/2004 | Meek et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |

(56) References Cited

U.S. PATENT DOCUMENTS

| | | |
|---|---|---|
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0244593 A1 | 11/2006 | Nycz et al. |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1 | 2/2007 | Miller et al. |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0185615 A1 | 8/2007 | Bossi et al. |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2007/0272746 A1 | 11/2007 | Ortiz et al. |
| 2008/0004908 A1 | 1/2008 | Oh et al. |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0061153 A1 | 3/2008 | Hickle et al. |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0186180 A1 | 8/2008 | Butler et al. |
| 2008/0191013 A1 | 8/2008 | Liberatore |
| 2008/0218307 A1 | 9/2008 | Schoettle |
| 2008/0228160 A1 | 9/2008 | Harrison |
| 2008/0231456 A1 | 9/2008 | Matityaho |
| 2008/0243088 A1 | 10/2008 | Evans |
| 2008/0270178 A1 | 10/2008 | McRae et al. |
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0060455 A1 | 3/2011 | Bogash et al. |
| 2011/0063091 A1 | 3/2011 | Kang |
| 2011/0068922 A1 | 3/2011 | Ross |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0202174 A1 | 8/2011 | Bogash et al. |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173440 A1 | 7/2012 | Becker et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0197927 A1* | 8/2013 | Vanderveen ............ G16H 40/20 705/2 |
| 2013/0218329 A1* | 8/2013 | Henderson ............. G16H 10/60 705/3 |
| 2013/0221082 A1 | 8/2013 | Botten |
| 2013/0225945 A1 | 8/2013 | Prince et al. |
| 2014/0060729 A1 | 3/2014 | Srnka et al. |
| 2014/0066880 A1 | 3/2014 | Prince et al. |
| 2014/0114472 A1 | 4/2014 | Bossi et al. |
| 2014/0117081 A1 | 5/2014 | Jablonski et al. |
| 2014/0136229 A1 | 5/2014 | Levine et al. |
| 2014/0142975 A1 | 5/2014 | Keefe et al. |
| 2014/0184390 A1 | 7/2014 | Elizondo, II |
| 2014/0184391 A1 | 7/2014 | Elizondo, II |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0282197 A1 | 9/2014 | Keefe et al. |
| 2014/0291397 A1 | 10/2014 | Caputo et al. |
| 2014/0367080 A1 | 12/2014 | Hussain et al. |
| 2015/0058182 A1 | 2/2015 | Kress-Spatz et al. |
| 2017/0109497 A1* | 4/2017 | Tribble ............ G06F 16/24578 |
| 2017/0132734 A1 | 5/2017 | MacDonald et al. |
| 2017/0212993 A1 | 7/2017 | Gitchell et al. |
| 2018/0039758 A1 | 2/2018 | MacDonald et al. |
| 2018/0247703 A1* | 8/2018 | D'Amato ............ G16H 10/60 |
| 2019/0088354 A1 | 3/2019 | Yanowitz et al. |
| 2019/0272396 A1 | 9/2019 | Clouser et al. |

(56) References Cited

U.S. PATENT DOCUMENTS

| | | | |
|---|---|---|---|
| 2019/0304583 A1* | 10/2019 | Henderson | G16H 20/10 |
| 2020/0013494 A1 | 1/2020 | Caputo et al. | |
| 2020/0167534 A1 | 5/2020 | Elizondo, II | |
| 2020/0357509 A1 | 11/2020 | Gitchell et al. | |
| 2021/0043291 A1 | 2/2021 | James et al. | |
| 2021/0241891 A1 | 8/2021 | Gitchell et al. | |
| 2021/0319872 A1* | 10/2021 | Valentine | G16H 40/67 |
| 2021/0383323 A1 | 12/2021 | MacDonald et al. | |
| 2022/0238219 A1 | 7/2022 | MacDonald et al. | |
| 2022/0282199 A1* | 9/2022 | Vann | G16B 40/00 |

FOREIGN PATENT DOCUMENTS

| | | |
|---|---|---|
| CN | 102791310 B | 12/2014 |
| EP | 2 496 283 | 9/2012 |
| IN | 2012/04914 P4 | 10/2013 |
| WO | WO 02/095675 | 11/2002 |
| WO | WO 03/071943 | 9/2003 |
| WO | WO 2006/026246 | 3/2006 |
| WO | WO 2006/135830 | 12/2006 |
| WO | WO 2010/074781 | 7/2010 |
| WO | WO 2011/056888 | 9/2011 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |
| WO | WO 2015/026387 | 2/2015 |

OTHER PUBLICATIONS

Bacheldor, Beth, "ASD Healthcare Deploys RFID Refrigerated Drug Cabinets", RFID Journal, Sep. 24, 2007, p. 1. <http://www.rfidjournal.com/articles/view?3632>.

Bacheldor, Beth, "Cardinal Health Readies Item-Level Pilot", RFID Journal, May 31, 2006, p. 1. <http://www.rfidjournal.com/articles/view?2380>.

Bacheldor, Beth, "UCSD Medical Center Expands Its RFID Deployment", RFID Journal, Oct. 29, 2008, pp. 2. <http://www.rfidjournal.com/articles/view?4423>.

Bacheldor, Beth, "UMass Med Center Finds Big Savings Through Tagging", RFID Journal, Nov. 21, 2007, pp. 2. <http://www.rfidjournal.com/articles/view?3763/2>.

Barlas, Stephen, "Pharmacy Product Tracing Likely to Go National—Costs to Pharmacies Worrisome," Pharmacy & Therapeutics, Jan. 2009, vol. 34 No. 1, p. 14.

Baum, "How did RFID help University of MD Medical Center cut medication error rate?" Med City News, https://medcitynews.com/2013/12/rfid-help-university-md-medical-center-cut-medication-error-rate/?rf=1, Dec. 4, 2013, 2 Pages.

Becker et al., "SmartDrawer: RFID-Based Smart Medicine Drawer for Assistive Environments", Conference: Proceedings of the 2nd International Conference on Pervasive Technologies Related to Assistive Environments, PETRA 2009, Corfu, Greece, Jun. 9-13, 2009, pp. 8.

Belson, D., "Storage, Distribution, and Dispensing of Medical Supplies," Create Interim Report Under FEMA Grant EMW-2004-GR-0112, Apr. 21, 2005, pp. 1-36.

Bendavid et al., "Using RFID to Improve Hospital Supply Chain Management for High Value and Consignment Items", Procedia Computer Science, vol. 5, 2011, pp. 849-856.

Bendavid et al., "Redesigning the Replenishment Process of Medical Supplies in Hospitals with RFID", Business Process Management Journal, 2010, vol. 16, No. 6, pp. 991-1013.

Brown, Dennis E., "RFID Implementation", McGraw-Hill Communications, 2007, Ch. 3 & 7 (portions), pp. 62-65, 81, 92-96, 106-113, 188-193 & 429.

Bryant, Blake, "Hacking SIEMs to Catch Hackers: Decreasing the Mean Time to Respond to Network Security Events with a Novel Threat Ontology in SIEM Software", Master's Thesis, University of Kansas, 2016, pp. 257.

çakici et al., "Using RFID for the Management of Pharmaceutical Inventory-System Optimization and Shrinkage Control," Decision Support Systems, 2011, pp. 842-852.

Cangialosi et al., "Leveraging RFID in Hospitals: Patient Life Cycle and Mobility Perspectives", IEEE Applications & Practice, Sep. 2007, pp. 18-23.

Chao et al., "Determining Technology Trends and Forecasts of RFID by a Historical Review and Bibliometric Analysis from 1991 to 2005", Technovation, vol. 27, 2007, pp. 268-279.

Collins, "RFID Cabinet Manages Medicine", RFID Journal, Aug. 12, 2004, p. 1. <http://www.rfidjournal.com/articles/pdf?1081>.

CPG Sec. 400.210, Radiofrequency Identification Feasibility Studies and Pilot Programs for Drugs Nov. 2004 Compliance Policy Guide available at: <http://www.fda.gov/ICECI/ComplianceManuals/CompliancePolicyGuidanceManual/ucm074357.htm>.

"Crash Cart Inventory Checklist", Outpatient Surgery Magazine, Oct. 2004, p. 1. <http://www.outpatientsurgery.net/resources/forms/2004/pdf/OutpatientSurgeryMagazine_0410_crashCart.pdf>.

Curtin et al., "Making the 'Most' out of RFID: a research agenda for the study of the adoption, usage and impact of RFID," Information Technology Management, Apr. 2007, pp. 87-110.

"Data Gathering Developments", Manufacturing Chemist, Feb. 1, 2005, p. 24. <https://www.manufacturingchemist.com/news/article_page/Data_gathering_developments/35805>.

Dutta et al., "RFID and Operations Management: Technology, Value, and Incentives", Production and Operations Management (POMS), vol. 16, No. 5, Sep.-Oct. 2007, pp. 646-655.

Edwards, John, "RFID Smart Shelves and Cabinets", RFID Journal, Aug. 24, 2009, pp. 4. <http://www.rfidjournal.com/articles/view?5140/4>.

*Electric Power Group* v. *Alstom, S.A.*, 830 F.3d 1350, 1353-54, 119 USPQ2d 1739, 1741-42 (Fed. Cir. 2016), pp. 12.

Epstein et al., "Development of a Scheduled Drug Diversion Surveillance System Based on an Analysis of Atypical Drug Transactions", Anesthesia and Analgesia, Oct. 2007, vol. 105, No. 4, pp. 1053-1060.

Erdem et al., "Investigation of RFID Tag Readability for Pharmaceutical Products at Item Level", Drug Development and Industrial Pharmacy, 2009, vol. 35, No. 11, pp. 1312-1324.

Fahrni, Jerry, "More RFID Refrigerator Stuff—Cubixx and myCubixx", Sep. 3, 2012, pp. 4. <http://jerryfahrni.com/2012/09/more-rfid-refrigerator-stuff-cubixx-and-mycubixx/>.

"Faraday Cage", Wikipedia, last edited Apr. 12, 2018, pp. 5. <https://en.wikipedia.org/wiki/Faraday_cage>.

Floerkemeier et al., "The Smart Box Concept for Ubiquitous Computing Environments", The Smart Box Concept for Ubiquitous Computing Environments, 2004, pp. 4.

Garza, Anyssa, "The Future of Pharmacy Medication Kit Storage", Pharmacy Times, https://www.pharmacytimes.com/contributor/anyssa-garza/2014/12/the-future-of-pharmacy-medication-kit-storage, Dec. 12, 2014, 2 Pages.

Glover et al., "RFID Essentials", O'Reilly Media, 2006, pp. 2, 14, 24, 31, 33, 107-110, 113-114, 117, 137-143, 162-169, 178-179.

Gonzalez, Stephanie, "Health Maintenance System (HMS) Hardware Research, Design, and Collaboration," NASA USRP—Internship Final Report, 2010, pp. 1-20.

Green, Kathryn, "Doing the Wave: Inventory Management with RFID", Diagnostic & Interventional Services, UMass Memorial Medical Center, Worcester, MA, vol. 15, No. 9, Sep. 2007, pp. 7. <https://www.cathlabdigest.com/articles/Doing-Wave-Inventory-Management-RFID>.

Harrop et al., "RFID for Healthcare and Pharmaceuticals, 2008-2018," Securing Pharma, May 2008, pp. 1-12.

Hawkins-Simons, "RFID Streamlines Refilling of Drug Trays", Pharmacy Technology Report, https://www.pharmacypracticenews.com/Pharmacy-Technology-Report/Article/03-14/RFID-Streamlines-Refilling-of-Drug-Trays/26159, Mar. 21, 2014, 9 Pages.

(56) References Cited

OTHER PUBLICATIONS

Ho et al., "A Prototype on RFID and Sensor Networks for Elder Healthcare: Progress Report", SIGCOMM '05 Workshops, Aug. 22-26, 2005, Philadelphia, PA, pp. 70-75.
Houliston, Bryan, "Integrating RFID Technology into a Drug Administration System," Bulletin of Applied Computing and Information Technology, vol. 3, No. 1, May 2005, pp. 8. Retrieved Sep. 26, 2013 from <http://citrenz.ac.nz/bacit/0301/2005Houliston_RFID.htm>.
Howard, JD, "Implementation of RFID in the Pharmaceutical Industry", Advisor: Dr. Jay Singh, California Polytechnic State University, San Luis Obispo, CA, Feb. 2009, pp. 11.
Humble, RN, Carol, "How RFID Freed Nurses From the Pain of Inventory Duties", Cath Lab Digest, Dec. 2009, vol. 17, No. 12. <https://www.cathlabdigest.com/articles/How-RFID-Freed-Nurses-From-Pain-Inventory-Duties>.
"Intel & Siemens Launch RFID Blood Bank in Malaysia", RFID Journal, Aug. 16, 2007, p. 1. <https://www.rfidjournal.com/articles/view?6801>.
Jones et al., "The Benefits, Challenges and Impacts of Radio Frequency Identification Technology (RFID) for Retailers in the UK", Marketing Intelligence & Planning, Mar. 2005, vol. 23, No. 4, pp. 395-402.
Jorgensen et al., "Executable Use Cases: Requirements for a Pervasive Health Care System," IEEE Software, Mar./Apr. 2004, pp. 34-41.
Juels, Ari, "RFID Security and Privacy: A Research Survey", IEEE Journal on Selected Areas in Communications, vol. 24, No. 2, Feb. 2006, pp. 381-394.
Kinsella, Bret, "Premier, Inc. Identifies Kit Check as 'Technology Breakthrough Product'—Awards exclusive agreement for pharmacy kit medication tracking solution", Press Release, https://kitcheck.com/2014/04/premier-inc-identifies-kit-check-technology-breakthrough-product-awards-exclusive-agreement-pharmacy-kit-medication-tracking-solution/, Apr. 2, 2014, 5 Pages.
KitCheck, Bluesight for Controlled Substances Overview, as retrieved Aug. 30, 2018 from https://web.archive.org/web/20180830001131/https://kitcheck.com/learn-more/video/bluesight-for-controlled-substances-overview/ in 1 page.
KitCheck, Diversion Events, as retrieved Aug. 30, 2018 from https://web.archive.org/web/20180830001851/https://kitcheck.com/solutions/controlled-substances/diversion-events/ in 3 pages.
KitCheck, "PharMEDium Prefilled Syringes with Kit Check: ASHP Symposium Summary", Jun. 2016, <https://kitcheck.com/wp-content/uploads/2016/06/pharmedium-prefilled-syringes-with-kit-check-download.pdf> in 9 pages.
KitCheck, Security, as retrieved Aug. 30, 2018 from https://web.archive.org/web/20180830000040/https://kitcheck.com/security/ in 1 page.
KitCheck, "St. Rita's Medical Center: 75% First-year ROI, Less Frustration", Case Study, 2016, <https://kitcheck.com/learn-more/case-study/st-ritas-medical-center/> in 2 pages.
Lahtela et al., "RFID and NFC in Healthcare: Safety of Hospitals Medication Care", 2008 Second International Conference on Pervasive Computing Technologies for Healthcare, Tampere, Finland, Jan. 30-Feb. 1, 2008, pp. 4.
Lai et al., "Enhancing Medication Safety and Reduce Adverse Drug Events on Inpatient Medication Administration using RFID," WSEAS Transactions on Communications, Oct. 2008, vol. 7, No. 10, pp. 1045-1054.
Lampe et al., "The Smart Box Application Model," Advances in Pervasive Computing, 2004, pp. 1-6.
Lewis, Mark O., "RFID-Enabled Capabilities and their Impact on Healthcare Process Performance", 31st International Conference on Information Systems, St. Louis, 2010, pp. 1-20.
Liu et al., "Point-of-Care Support for Error-Free Medication Process" (Jun. 25, 2007), retrieved Aug. 21, 2017, 12 pages, available at http://ieeexplore.ieee.org/document/4438162/.
McCall et al., "RMAIS: RFID-based Medication Adherence Intelligence System" (Aug. 31, 2010), retrieved Aug. 21, 2017, 4 pages, available at http://ieeexplore.ieee.org/document/5627529/.

"McKesson's Announces New Touch-Screen Driven Medication Dispensing Solution", Business Wire, Jun. 15, 2009, pp. 2, Available at: <http://www.businesswire.com/news/home/20090615005349/en/McKesson- Announces-Touch-Screen-Driven-Medication-Dispensing-Solution#.VR7quPnF_10>.
"Medical Packaging Inc. Announces Clear Stem Flag Label System for Ampoules, Vials, and Syringes" Feb. 1, 2006 available at: <http://www.medpak.com/v1/news/20060201_CSFLAG.pdf>, in 1 page.
"Medication Tray Management" Pharmacy Purchasing & Products, Feb. 2018, pp. 18 & 20.
"Medication Tray Management" Pharmacy Purchasing & Products, Presentation, Nov. 2018, pp. 76 & 78.
"Medication Tray Management" Pharmacy Purchasing & Products, State of Pharmacy Automation, Aug. 2016, pp. 42 & 45.
"Medication Tray Management" Pharmacy Purchasing & Products, State of Pharmacy Automation, Aug. 2019, pp. 34-35.
Mehrjerdi, Yahia Zare, "RFID-Enabled Healthcare Systems: Risk-Benefit Analysis", International Journal of Pharmaceutical and Healthcare Marketing, 2010, vol. 4, No. 3, pp. 282-300.
Meiller et al., "Adaptive Knowledge-Based System for Health Care Applications with RFID-Generated Information", Decision Support Systems, vol. 51, 2011, pp. 198-207.
Mowry, Mike, "A Survey of RFID in the Medical Industry: With Emphasis on Applications to Surgery and Surgical Devices", MAE188, Introduction to RFID, Dr. Rajit Gadh, UCLA, Jun. 9, 2008, pp. 22.
"New RFID Medical Cabinets Deployed at 50 Hospitals", RFID Journal, Sep. 17, 2007, pp. 2. <https://www.rfidjournal.com/articles/view?6823>.
New et al., "Utilize ADC Transaction Data to Detect Diversion", Oct. 2017, vol. 14, No. 10, pp. 3, as retrieved from https://www.pppmag.com/article/2119/.
O'Connor, Mary Catherine, "Drug Distributor Uses RFID to Vend Meds", RFID Journal, May 23, 2006, pp. 2. <https://www.rfidjournal.com/articles/view?2363/2>.
O'Connor, Mary Catherine, "GlaxoSmithKline Tests RFID on HIV Drug", RFID Journal, Mar. 24, 2006, pp. 2. <https://www.rfidjournal.com/articles/view?2219/>.
O'Connor, Mary Catherine, "Interrogators Start to Evolve", RFID Journal, Jun. 1, 2006, pp. 3. <http://www.rfidjournal.com/purchase-access?type=Article&id=2398&r=%2Farticles%2Fview%3F2398>.
O'Connor, Mary Catherine, "Johnson & Johnson Finds Value in Multiple RFID Apps", RFID Journal, Apr. 23, 2008, pp. 2. <http://www.rfidjournal.com/articles/pdf?4046>.
O'Connor, Mary Catherine, "McKesson Starts RFID Pilot for Viagra", RFID Journal, Feb. 17, 2005, pp. 2. <http://www.rfidjournal.com/articles/view?2157>.
O'Connor, Mary Catherine, "Pfizer Using RFID to Fight Fake Viagra", RFID Journal, Jun. 6, 2006, pp. 2. <http://www.rfidjournal.com/articles/pdf?2075>.
O'Connor, Mary Catherine, "To Keep Drugs from Expiring, Hospital Tests Intelliguard System", RFID Journal, Jan. 12, 2011, pp. 3. <http://www.rfidjournal.com/articles/view?8123>.
"ODIN Innovation Lab: EasyTunnel RFID", as posted Jul. 13, 2009, archived via archive.org <https://web.archive.org/web/20200316173502/https://www.youtube.com/watch?v=0rQhT4slQnw>, 1 page.
"ODIN RFID HQ Tour 2009", as posted Mar. 19, 2009, archived via archive.org <https://web.archive.org/web/20200316180429/https://www.youtube.com/watch?v=4Y4XIIDOB_Y>, 1 page.
O'Driscoll et al., "RFID: An Ideal Technology for Ubiquitous Computing?" Dublin Institute of Technology School of Electronic and Communications Conference Papers, Jan. 1, 2008, pp. 1-17.
Pace et al., "Distributed Ambulatory Research in Therapeutics Network (DARTNet): Summary Report", Effective Health Care Research Reports, No. 14, Agency for Healthcare Research and Quality, Jul. 2009, pp. 41.
Pappu, Ph.D. et al., "RFID in Hospitals: Issues and Solutions" Consortium for the Accelerated Deployment of RFID in Distribution, Sep. 2004, pp. 1-12.
Parida et al., "Application of RFID Technology for In-House Drug Management System", 15th International Conference on Network-Based Information Systems, 2012, pp. 577-581.

(56) References Cited

OTHER PUBLICATIONS

"RFID Medical Cabinets Evaluated in New Benchmark", RFID Journal, Sep. 12, 2007, pp. 2. <http://www.rfidjournal.com/articles/view?6819>.
Roberti, Mark, "RFID Basics for Health Care", RFID in Health Care, Produced by RFID Journal, Sep. 17, 2009, The Westin Waltham-Boston, Waltham, MA, pp. 33.
Saygin, C., "Adaptive Inventory Management Using RFID Data", The International Journal of Advanced Manufacturing Technology, 2007, vol. 32, pp. 1045-1051.
Singh et al., "Versatility of Radio Frequency Identification (RFID) Tags in the Pharmaceutical Industry", Instrumentation Science and Technology, vol. 36, pp. 656-663, 2008.
Summerfield, et al. "Evaluation of Medication Kit Processing Time Using Radio Frequency Identification (RFID) Technology", Innovations in Pharmacy, 2015, vol. 6, No. 2, Article 199, 7 Pages.
Swedberg, Claire, "North Carolina Hospital Identifies Recalled Drugs Via RFID", RFID Journal, http://www.rfidjournal.com/articles/view?10913, Aug. 14, 2013, 4 Pages.
Swedberg, Claire, "Tennessee Hospital Tracks High-Value Items", RFID Journal, Aug. 5, 2009, pp. 2. <http://www.rfidjournal.com/articles/view?5106>.
Swedberg, Claire, "Zimmer Ohio to Use RFID to Manage Orthopedic Products", RFID Journal, May 12, 2010, pp. 3. <https://www.rfidjournal.com/articles/pdf?7588>.
Tsai et al., "iMAT: Intelligent Medication Administration Tools" (Jul. 1, 2010), retrieved Aug. 21, 2017, 8 pages, available at http://ieeexplore.ieee.org/document/5556551/.
Tsai et al., "Smart Medication Dispenser: Design, Architecture and Implementation" (Sep. 27, 2010), retrieved Aug. 21, 2017, 12 pages, available at http://ieeexplore.ieee.org/document/5585838/.
Tzeng et al., "Evaluating the Business Value of RFID: Evidence from Five Case Studies," International Journal of Production Economics, 2008, vol. 112, pp. 601-613.
"UPM Raflatac UHF EPC Gen2 RFID in ODIN Solution at Johnson-Johnson DePuyIn-Q-Tel", as posted Jun. 10, 2009, archived via archive.org <https://web.archive.org/web/20200316174347/https://www.youtube.com/watch?v=JWGyR8Bgfl8>, 1 page.
"Vizient, Inc. Awards Kit Check Contract for Pharmacy Kit Medication Inventory Tracking and Replenishment", Press Release, http://www.prweb.com/releases/2016/09/prweb13691526.htm, Sep. 19, 2016, 3 Pages.
Wang et al., "Applying RFID Technology to Develop a Distant Medical Care Service Platform," International Journal of Electronic Business Management, 2010, vol. 8, No. 2, pp. 161-170.
Wang et al., "RFID Applications in Hospitals: A Case Study on a Demonstration RFID Project in a Taiwan Hospital", Proceedings of the 39th Hawaii International Conference on System Sciences, 2006, pp. 1-10.
Wasserman, Elizabeth, "Purdue Pharma to Run Pedigree Pilot", RFID Journal, May 31, 2005, pp. 2. <http://www.rfidjournal.com/articles/view?1626>.
Complaint, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Dec. 1, 2017, 45 pages.
Exhibit L; Fagron Academy, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Dec. 1, 2017, 2 pages.
Defendant's Answer, Affirmative Defenses and Counterclaims to Plaintiff's Complaint, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 2, 2018, 43 pages.
Plaintiff's Answer to Defendant's Counterclaims, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 19, 2018, 14 pages.

Plaintiff Kit Check, Inc.'s Motion to Strike Insufficient Defenses, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Jan. 19, 2018, 8 pages.
Defendant's First Amended Answer, Affirmative Defenses and Counterclaims to Plaintiff's Complaint, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 43 pages.
Defendant's Memorandum in Opposition to Plaintiff Kit Check, Inc.'s Motion to Strike Insufficient Defenses, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 6 pages.
Plaintiff's Answer to Defendant's First Amended Counterclaims, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Feb. 21, 2018, 14 pages.
Plaintiff Kit Check, Inc.'s Reply in Support of its Motion to Strike Insufficient Defenses, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 21, 2018, 6 pages.
Defendant Health Care Logistics, Inc.'s Motion for Judgment on the Pleadings Pursuant to Fed. R. Civ. P. 12(C), *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 31 pages.
Exhibit A; U.S. Pat. No. 8,990,099, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 12 pages.
Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 13, 2018, 9 pages.
Defendant Health Care Logistics, Inc's Invalidity Contentions Pursuant to Local Patent Rule 103.4, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 18, 2018, 25 pages.
Exhibit 1; Initial Invalidity Claim Chart for U.S. Pat. No. 8,990,099, *Kit Check, Inc.* v. *Health Care Logistics, Inc.*, Case No. 2:17-cv-01041-ALM-CMV (S.D. Ohio), Jun. 18, 2018, 51 pages.
Exhibit 2; Initial Invalidity Claim Chart for U.S. Pat. No. 9,058,413, *Kit Check, Inc.* v. *Health Care Logistics, Inc.*, Case No. 2:17-cv-01041-ALM-CMV (S.D. Ohio), Jun. 18, 2018, 94 pages.
Exhibit 3; Initial Invalidity Claim Chart for U.S. Pat. No. 9,058,412, *Kit Check, Inc.* v. *Health Care Logistics, Inc.*, Case No. 2:17-cv-01041-ALM-CMV (S.D. Ohio), Jun. 18, 2018, 83 pages.
Exhibit 4; Initial Invalidity Claim Chart for U.S. Pat. No. 9,734,294, *Kit Check, Inc.* v. *Health Care Logistics, Inc.*, Case No. 2:17-cv-01041-ALM-CMV (S.D. Ohio), Jun. 18, 2018, 58 pages.
Exhibit 5; Initial Invalidity Claim Chart for U.S. Pat. No. 9,805,169, *Kit Check, Inc.* v. *Health Care Logistics, Inc.*, Case No. 2:17-cv-01041-ALM-CMV (S.D. Ohio), Jun. 18, 2018, 251 pages.
Exhibit 6; Initial Invalidity Claim Chart for U.S. Pat. No. 9,037,479, *Kit Check, Inc.* v. *Health Care Logistics, Inc.*, Case No. 2:17-cv-01041-ALM-CMV (S.D. Ohio), Jun. 18, 2018, 43 pages.
Exhibit 7; Initial Invalidity Claim Chart for U.S. Pat. No. 9,367,665, *Kit Check, Inc.* v. *Health Care Logistics, Inc.*, Case No. 2:17-cv-01041-ALM-CMV (S.D. Ohio), Jun. 18, 2018, 109 pages.
Plaintiff Kit Check, Inc.'s Memorandum in Opposition to Defendant Health Care Logistics, Inc.'s Motion for Judgment on the Pleadings, *Kit Check, Inc.* v. *Health Care Logistics, Inc.* (involving U.S. Pat.

(56) References Cited

OTHER PUBLICATIONS

Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 35 pages.
Exhibit 1; Non-Final Office Action for U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Jun. 29, 2018, 11 pages.
Exhibit 2; Notice of Allowance for U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Jun. 29, 2018, 15 pages.
Exhibit 3; Non-Final Office Action for U.S. Pat. No. 9,367,665, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 12 pages.
Exhibit 4; Response to Non-Final Office Action for U.S. Pat. No. 9,367,665, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 18 pages.
Defendant Health Care Logistics, Inc.'s Reply in Support of Motion for Judgment on the Pleadings Pursuant To Fed. R. Civ. P. 12(C), *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 22 pages.
Exhibit A, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 43 pages.
Exhibit B; Plaintiff Kit Check, Inc.'s Disclosure of Asserted Claims and Infringement Contentions under Local Patent Rule 103.2, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 11 pages.
Plaintiff Kit Check, Inc.'s Motion to Strike Portions of Defendants' Reply or, in the Alternative, Motion for Leave to File a Sur-Reply, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 6 pages.
Exhibit A; Plaintiff Kit Check, Inc.'s Sur-Reply in Opposition to Defendant's Motion for Judgment on the Pleadings, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 5 pages.
Defendant Health Care Logistics, Inc.'s Memorandum In Opposition to Plaintiff Kit Check, Inc.'s Motion to Strike Portions of Defendant's Reply or, in the Alternative, Motion for Leave to File a Sur-Reply, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 31, 2018, 6 pages.
Plaintiff Kit Check, Inc.'s Reply in Support of its Motion to Strike Portions of Defendant's Reply or, in the Alternative, Motion for Leave to File a Sur-Reply, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 14, 2018, 7 pages.
Joint Claim Construction and Prehearing Statement, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 20, 2018, 21 pages.
Plaintiff Kit Check, Inc.'s Opening Claim Construction Brief, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 50 pages.
Exhibit 1; Disputed Claim Terms Chart, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 4 pages.
Declaration of Jeffrey Fischer, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Nov. 16, 2018, 24 pages.
Defendant Health Care Logistics, Inc.'s Opening Claim Construction Brief, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Nov. 16, 2018, 32 pages.
Exhibit 1002; File History of U.S. Pat. No. 9,367,665, *Health Care Logistics, Inc. v. Kit Check, Inc.*, Case No. PGR2019-00022, Nov. 30, 2018, 256 pages.
Exhibit 1003; Expert Declaration, *Health Care Logistics, Inc. v. Kit Check, Inc.*, Case No. PGR2019-00022, Nov. 30, 2018, 9 pages.
Exhibit 1013; Claim Construction Brief (Defendant), *Health Care Logistics, Inc. v. Kit Check, Inc.*, Case No. PGR2019-00022, Nov. 30, 2018, 32pages.
Exhibit 1014; Claim Construction Brief (Plaintiff), *Health Care Logistics, Inc. v. Kit Check, Inc.*, Case No. PGR2019-00022, Nov. 30, 2018, 50 pages.
Petition for Inter Partes Review of U.S. Pat. No. 8,990,099, *Health Care Logistics, Inc. v. Kit Check, Inc.*, Case No. IPR2019-00376, Nov. 30, 2018, 42 pages.
Exhibit 1002; File History of U.S. Pat. No. 8,990,099, *Health Care Logistics, Inc. v. Kit Check, Inc.*, Case No. IPR2019-00376, Nov. 30, 2018, 557 pages.
Exhibit 1003; Expert Declaration, *Health Care Logistics, Inc. v. Kit Check, Inc.*, Case No. IPR2019-00376, Nov. 30, 2018, 9 pages.
Exhibit 1010; Claim Construction Brief (Defendant), *Health Care Logistics, Inc. v. Kit Check, Inc.*, Case No. IPR2019-00376, Nov. 30, 2018, 32 pages.
Exhibit 1011; Claim Construction Brief (Plaintiff), *Health Care Logistics, Inc. v. Kit Check, Inc.*, Case No. IPR2019-00376, Nov. 30, 2018, 50 pages.
Petition for Inter Partes Review of U.S. Pat. No. 9,058,412, *Health Care Logistics, Inc. v. Kit Check, Inc.*, Case No. IPR2019-00385, Nov. 30, 2018, 75 pages.
Exhibit 1002; File History of U.S. Pat. No. 9,058,412, *Health Care Logistics, Inc. v. Kit Check, Inc.*, Case No. IPR2019-00385, Nov. 30, 2018, 75 pages.
Exhibit 1003; Expert Declaration, *Health Care Logistics, Inc. v. Kit Check, Inc.*, Case No. IPR2019-00385, Nov. 30, 2018, 9 pages.
Exhibit 1013; Claim Construction Brief (Defendant), *Health Care Logistics, Inc. v. Kit Check, Inc.*, Case No. IPR2019-00385, Nov. 30, 2018, 32 pages.
Exhibit 1014; Claim Construction Brief (Plaintiff), *Health Care Logistics, Inc. v. Kit Check, Inc.*, Case No. IPR2019-00385, Nov. 30, 2018, 50 pages.
Petition for Inter Partes Review of U.S. Pat. No. 9,058,413, *Health Care Logistics, Inc. v. Kit Check, Inc.*, Case No. IPR2019-00387, Dec. 1, 2018, 73 pages.
Exhibit 1002; File History of U.S. Pat. No. 9,058,413, *Health Care Logistics, Inc. v. Kit Check, Inc.*, Case No. IPR2019-00387, Dec. 1, 2018, 549 pages.
Exhibit 1003; Expert Declaration, *Health Care Logistics, Inc. v. Kit Check, Inc.*, Case No. IPR2019-00387, Dec. 1, 2018, 9 pages.
Exhibit 1009; Children's Hospital Boston Joins Others Using RFID to Track Implantables, *Health Care Logistics, Inc. v. Kit Check, Inc.*, Case No. IPR2019-00387, Dec. 1, 2018, 3 pages.
Exhibit 1012; The "Orange Book", *Health Care Logistics, Inc. v. Kit Check, Inc.*, Case No. IPR2019-00387, Dec. 1, 2018, 1103 pages.

(56) References Cited

OTHER PUBLICATIONS

Exhibit 1013; Claim Construction Brief (Defendant), *Health Care Logistics, Inc.* v. *Kit Check, Inc.*, Case No. IPR2019-00387, Dec. 1, 2018, 32 pages.
Exhibit 1014; Claim Construction Brief (Plaintiff), *Health Care Logistics, Inc.* v. *Kit Check, Inc.*, Case No. IPR2019-00387, Dec. 1, 2018, 50 pages.
Petition for Inter Partes Review of U.S. Pat. No. 9,805,169, *Health Care Logistics, Inc.* v. *Kit Check, Inc.*, Case No. IPR2019-00388, Dec. 1, 2018, 76 pages.
Exhibit 1002; File History of U.S. Pat. No. 9,805,169, *Health Care Logistics, Inc.* v. *Kit Check, Inc.*, Case No. IPR2019-00388, Dec. 1, 2018, 286 pages.
Exhibit 1003; Expert Declaration, *Health Care Logistics, Inc.* v. *Kit Check, Inc.*, Case No. IPR2019-00388, Dec. 1, 2018, 9 pages.
Exhibit 1009; Claim Construction Brief (Defendant), *Health Care Logistics, Inc.* v. *Kit Check, Inc.*, Case No. IPR2019-00388, Dec. 1, 2018, 32 pages.
Exhibit 1010; Claim Construction Brief (Plaintiff), *Health Care Logistics, Inc.* v. *Kit Check, Inc.*, Case No. IPR2019-00388, Dec. 1, 2018, 50 pages.
Petition for Inter Partes Review of U.S. Pat. No. 9,367,665, *Health Care Logistics, Inc.* v. *Kit Check, Inc.*, Case No. IPR2019-00394, Dec. 3, 2018, 69 pages.
Exhibit 1002; File History of U.S. Pat. No. 9,367,665, *Health Care Logistics, Inc.* v. *Kit Check, Inc.*, Case No. IPR2019-00394, Dec. 3, 2018, 256 pages.
Exhibit 1003; Expert Declaration, *Health Care Logistics, Inc.* v. *Kit Check, Inc.*, Case No. IPR2019-00394, Dec. 3, 2018, 9 pages.
Exhibit 1013; Claim Construction Brief (Defendant), *Health Care Logistics, Inc.* v. *Kit Check, Inc.*, Case No. IPR2019-00394, Dec. 3, 2018, 32 pages.
Exhibit 1014; Claim Construction Brief (Plaintiff), *Health Care Logistics, Inc.* v. *Kit Check, Inc.*, Case No. IPR2019-00394, Dec. 3, 2018, 50 pages.
Plaintiff Kit Check, Inc.'s Notice of Filing Deposition Transcript of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805, 169), Case No. 2:17-cv-01041-ALM-CMV (S.D. Ohio), Jan. 3, 2019, 3 pages.
Exhibit A; Deposition of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 86 pages.
Plaintiff Kit Check, Inc.'s Responsive Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 23 pages.
Exhibit A, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 43 pages.
Exhibit B; Deposition of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Defendant Health Care Logistics, Inc.'s Response to Plaintiff Kit Check, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Plaintiff Kit Check, Inc.'s Memorandum in Opposition to Defendant Health Care Logistics, Inc.'s Motion for Stay, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 21 pages.
Exhibit 1; Defendant Health Care Logistics, Inc.'s Invalidity Contentions Pursuant to Local Patent Rule 103.4, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 26 pages.
Defendant Health Care Logistics, Inc.'s Reply in Support of Motion for Stay, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 25, 2019, 10 pages.
Patent Owner's Preliminary Response, *Health Care Logistics, Inc.* v. *Kit Check, Inc.*, Case No. IPR2019-00376, U.S. Pat. No. 8,990,099, Mar. 8, 2019, 26 pages.
Patent Owner's Preliminary Response, *Health Care Logistics, Inc.* v. *Kit Check, Inc.*, Case No. IPR2019-00385, U.S. Pat. No. 9,058,412 B2, Mar. 8, 2019, 28 pages.
Patent Owner's Preliminary Response, *Health Care Logistics, Inc.* v. *Kit Check, Inc.*, Case No. IPR2019-00387, U.S. Pat. No. 9,058,413 B2, Mar. 13, 2019, 28 pages.
Patent Owner's Preliminary Response, *Health Care Logistics, Inc.* v. *Kit Check, Inc.*, Case No. IPR2019-00388, U.S. Pat. No. 9,805,169 B2, Mar. 13, 2019, 25 pages.
Patent Owner's Preliminary Response, *Health Care Logistics, Inc.* v. *Kit Check, Inc.*, Case No. IPR2019-00394, U.S. Pat. No. 9,367,668 B2, Mar. 13, 2019, 28 pages.
Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Mar. 14, 2019, 17 pages.
Joint Stipulation of Partial Dismissal Without Prejudice, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Apr. 16, 2019, 2 pages.
Transcript of Markman Hearing Proceedings, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 6, 2019, 74 pages.
Decision Denying Institution of Inter Partes Review 35 U.S.C. § 314, *Health Care Logistics, Inc.* v. *Kit Check, Inc.*, Case No. IPR2019-00385, U.S. Pat. No. 9,058,412 B2, Jun. 3, 2019, 28 pages.
Decision Denying Institution of Inter Partes Review 35 U.S.C. § 314, *Health Care Logistics, Inc.* v. *Kit Check, Inc.*, Case No. IPR2019-00385, U.S. Pat. No. 9,805,169 B2, Jun. 3, 2019, 20 pages.
Decision Denying Institution of Inter Partes Review 35 U.S.C. § 314, *Health Care Logistics, Inc.* v. *Kit Check, Inc.*, Case No. IPR2019-00376, U.S. Pat. No. 8,990,099 B2, Jun. 4, 2019, 18 pages.
Decision Denying Institution of Inter Partes Review 35 U.S.C. § 314, *Health Care Logistics, Inc.* v. *Kit Check, Inc.*, Case No. IPR2019-00387, U.S. Pat. No. 9,058,413 B2, Jun. 7, 2019, 26 pages.
Decision Denying Institution of Inter Partes Review 35 U.S.C. § 314, *Health Care Logistics, Inc.* v. *Kit Check, Inc.*, Case No. IPR2019-00394, U.S. Pat. No. 9,367,665 B2, Jun. 11, 2019, 25 pages.
Stipulation and [Proposed] Order Granting Leave to Amend Plaintiff's Infringement Contentions and Defendant's Invalidity Contentions, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 3, 2019, 3 pages.
Defendant Health Care Logistics, Inc.'s Motion for Leave to File Second Amended Answer, Affirmative Defenses, and Counterclaims, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 17, 2019, 5 pages.
Exhibit A; Defendant's Second Amended Answer, Affirmative Defenses, and Counterclaims to Plaintiff's Complaint, *Kit Check, Inc.* v. *Health Care Logistics, Inc.* (involving U.S. Pat. Nos. 8,990,099,

(56) References Cited

OTHER PUBLICATIONS 9,037,479, 9,058,412, 9,058,413, 9,367,665, 9,734,294, and 9,805,169), Case No. 2:17-cv-01041-ALM-CMV (S.D. Ohio), Jul. 17, 2019, 49 pages.

Request for Ex Parte Reexamination Under 35 U.S.C. 302-307 and 37 C.F.R. 1.510, U.S. Pat. No. 8,990,099 B2, U.S. Appl. No. 13/554,342, filed Jul. 25, 2019 in 80 pages.

Request for Ex Parte Reexamination Under 35 U.S.C. 302-307 and 37 C.F.R. 1.510, U.S. Appl. No. 9,058,412 B2, U.S. Appl. No. 14/603,730, filed Jul. 26, 2019 in 118 pages.

Request for Ex Parte Reexamination Under 35 U.S.C. 302-307 and 37 C.F.R. 1.510, U.S. Pat. No. 9,058,413 B2, U.S. Appl. No. 14/603,828, filed Jul. 25, 2019 in 151 pages.

Request for Ex Parte Reexamination Under 35 U.S.C. 302-307 and 37 C.F.R. 1.510, U.S. Appl. No. 9,805,169 B2, U.S. Appl. No. 14/701,958, filed Jul. 26, 2019 in 220 pages.

Request for Ex Parte Reexamination Under 35 U.S.C. 302-307 and 37 C.F.R. 1.510, U.S. Pat. No. 9,367,665 B2, U.S. Appl. No. 14/818,113, filed Jul. 26, 2019 in 164 pages.

Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM- CMV (S.D. Ohio), Aug. 30, 2019, 26 pages.

\* cited by examiner

IDENTIFYING DISCREPANCIES BETWEEN EVENTS FROM DISPARATE SYSTEMS

CROSS-REFERENCE TO RELATED APPLICATIONS

This application is a continuation of U.S. patent application Ser. No. 17/807,689, filed Jun. 17, 2022, which is a continuation of U.S. patent application Ser. No. 16/121,155, filed Sep. 4, 2018, each of which is hereby incorporated by reference. U.S. patent application Ser. No. 16/121,155 claims priority benefit to U.S. Provisional Patent Application No. 62/554,145, filed Sep. 5, 2017, U.S. Provisional Patent Application No. 62/553,641, filed Sep. 1, 2017, and U.S. Provisional Patent Application No. 62/553,675, filed Sep. 1, 2017, the subject matter of which is hereby incorporated by reference.

BACKGROUND

Pharmaceutical items (for example, drugs, diluents, medical and surgical supplies, gauze, scissors, needles, labels, baggies, bandages, packaging, vial, syringes, and/or other items that the pharmacy is responsible for) such as medications (for example, drugs, diluents, etc., in solid or liquid form) can be difficult to track in a healthcare environment. For example, within the healthcare environment, there can be significant waste, loss, or abuse of medications. Furthermore, it can be difficult to identify equivalent pharmacy items. Furthermore, it can be difficult to communicate pharmacy item event data without communicating personal health information.

DETAILED DESCRIPTION

Pharmacy Items and Bins

Figure 1:
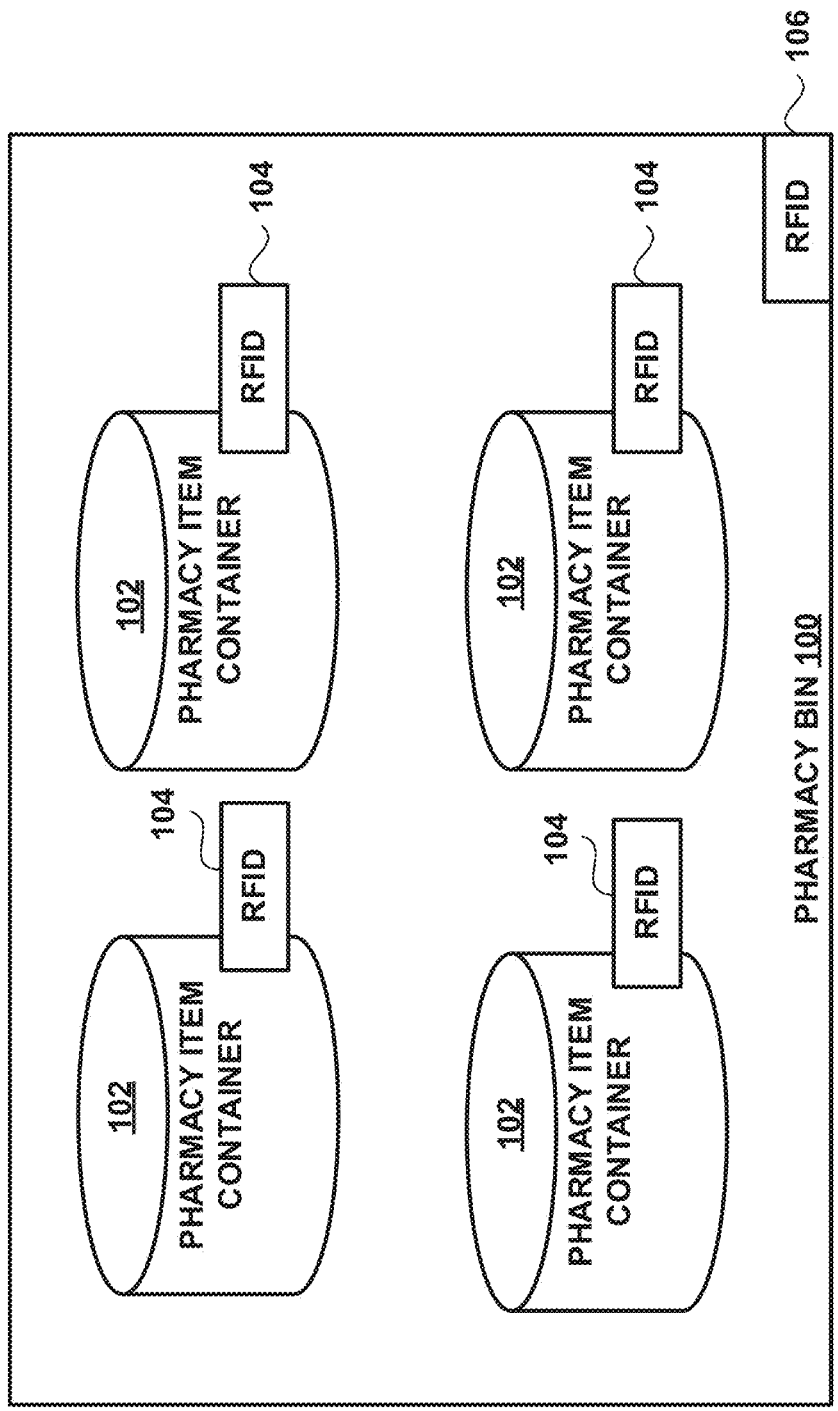
FIG. 1 is a block diagram illustrating an embodiment of a pharmacy bin with multiple pharmacy item containers placed therein, each pharmacy item container having an RFID tag attached thereto.

FIG. 1 is a block diagram illustrating an embodiment of a pharmacy bin 100 with multiple pharmacy item containers 102 placed therein, each pharmacy item container 102 having an RFID tag 104 attached thereto. The bin 100 can be made of a material, such as plastic, that reduces the likelihood of interfering or blocking radio signals emitted from an antenna. In addition, the bin 100 can have its own RFID tag 106 attached thereto.

As will be described in greater detail below, the pharmacy item containers 102 can come in any number of forms, such as, but not limited to, vials, bottles, syringes, boxes, ampoules, IV bags, baggies, or other containers configured to store a medication. Further, each pharmacy item container 102 can store or contain one more pharmacy items, such as, but not limited to, tablets, cartridges, creams, crystals, powder, fluid, film, gel, etc. For example, a bottle of Ibuprofen can store multiple Ibuprofen tablets and a vial of Propofol can store 20 mL of Propofol, etc.

In some cases, different pharmacy item containers 102 in the bin 100 can store the same or different types of pharmacy items. For example, one pharmacy item container 102 can store Propofol and another can store Oxycodone. In certain cases, the pharmacy items containers 102 can store similar pharmacy items. For example, one pharmacy item container 102 can store a generic version of a drug and another can store the branded version of the same drug or active ingredient. Similarly, different pharmacy item containers 102 can store the same drug manufactured by different companies, the same drug with different concentrations, different routes of administration, different dosage forms, and/or different package types, etc.

The RFID tags 104 can be passive, active, or battery-assisted passive. An active tag can include an on-board battery and can periodically transmit its tag information. A battery-assisted passive (BAP) can include a small battery on board and can be activated when in the presence of an RFID reader. A passive tag can be less expensive and smaller because it may not include a battery; instead, the tag can use the radio energy transmitted by the RFID reader to power the integrated circuit and generate a response.

The RFID tags 104 may either be read-only, for example, having factory-assigned tag information, such as a serial number or other data, that is used as a key into a database, or may be read/write, where object-specific data, serial number, can be written into the tag 104. Field programmable tags may be write-once, read-multiple, or "blank" tags that may be written with an electronic product code by the user, etc.

The RFID tags 104 can include an integrated circuit for storing and processing information and modulating and demodulating radio-frequency (RF) signals, and an antenna for receiving an interrogation signal from an RFID reader and transmitting the tag information. The tag information can be stored in a non-volatile memory of the integrated circuit or other memory on the RFID tag. Further, the RFID tag can include either fixed or programmable logic for processing the transmitting the tag information.

In use, an RFID reader transmits an encoded radio signal to interrogate the tag 104. The RFID tag 104 receives the message and then responds with the tag information. When the RFID tag 104 is a passive tag, the RFID tag 104 can use the radio signal received from the RFID reader to energize the tag 104. The tag information may be a unique tag serial number or may be product-related information such as a stock number, lot or batch number, production date, or other specific information stored on the RFID tag 104. In cases where tags have individual serial numbers, the RFID system can discriminate among several tags that might be within the range of the RFID reader and read them simultaneously. The RFID reader can communicate the tag information to an information processing system, which can further process the tag information. As will be described in greater detail below, an information processing system can use the tag information to identify a bin, the pharmacy items in the bin, determine equivalences, or update item locations, among other things.

Figure 2A:
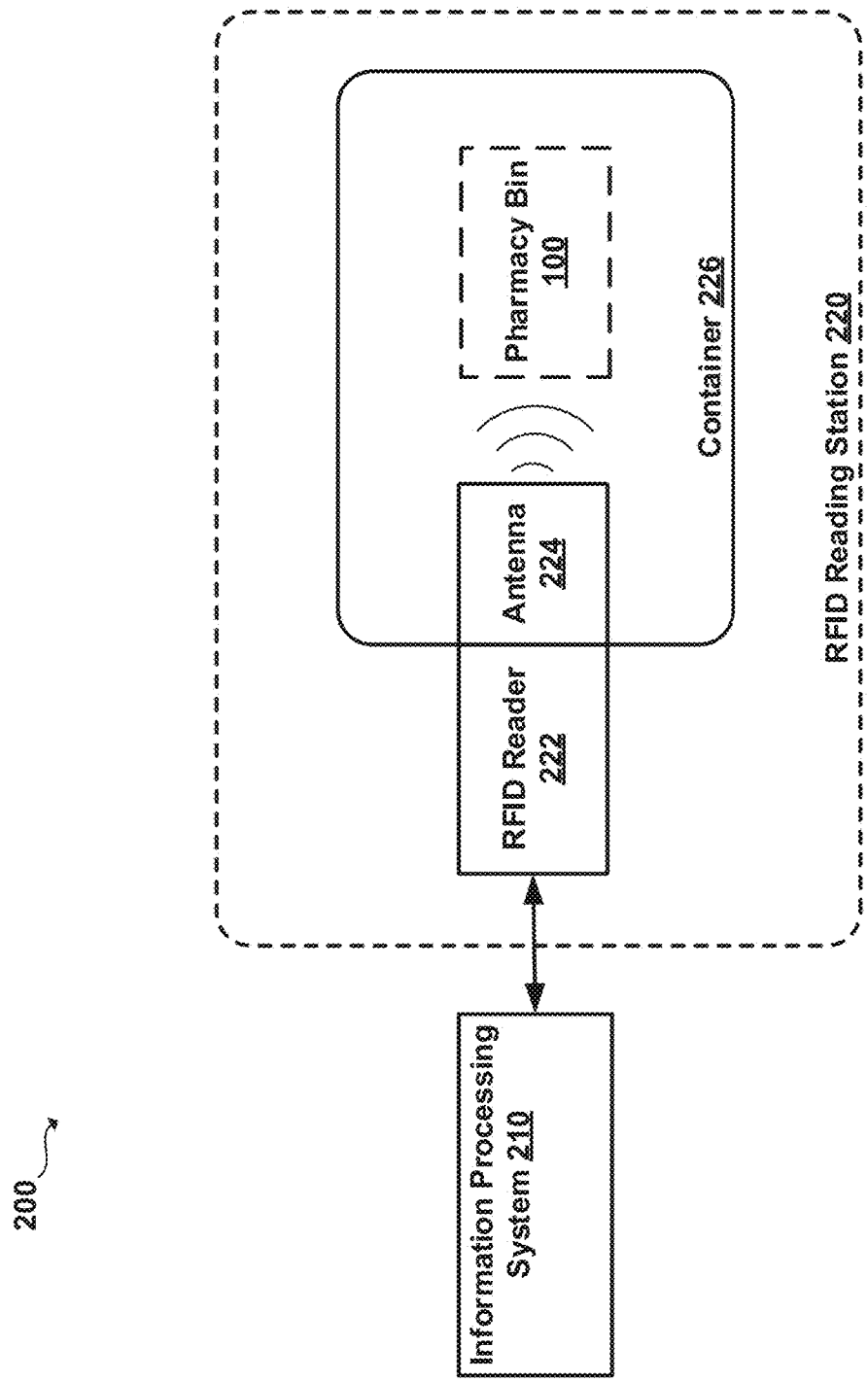
FIG. 2A is a block diagram illustrating an embodiment of an RFID reading and processing system.

FIG. 2A is a block diagram illustrating an embodiment of an RFID reading and processing system 200. The system 200 includes an information processing system 210 in communication with an RFID reading station 220 that includes an RFID reader 222 and a container 226 for placing a pharmacy bin 100 or pharmacy item container 102.

The information processing system 210 can be implemented in a variety of ways and can include one or more computers, servers, virtual machines, or the like. In some embodiments, the information processing system 210 can be included as part of the RFID reading station 220 or RFID reader 222. In certain embodiments, the information processing system 210 communicates with the RFID reading station 220 via one or more networks, such as a local or wide area network. In some cases, the information processing system can be implemented using a local computing device, such as a processor or computer located in the same room as the RFID reading station 220, or on a remote computing device, such as a server that communicates with the local computing device via a local or wide area network.

The local computing device can include a computer application that receives tag information from the RFID reader and communicates with a remote computing device via a wide area network, such as the Internet. The remote computing device can be made up of one or more computing devices, such as one or more servers, data stores, or virtual machines, and can store bin information such as the types of bins used in a pharmacy environment. The remote computing device can also store records that include information regarding individual bins and pharmacy items. In some cases, the information processing system 210 can receive information from multiple RFID reading stations 220 located in a variety of locations.

Using the tag information received from an RFID reading station 220, the information processing system 210 can identify equivalent pharmacy items in a bin 100 or in the container 226 and update bin data, as will be described in greater detail below.

In addition to storing the current or most recent information regarding the bins 100, the information processing system 210 may also store a virtual history for each bin 100. Such a virtual history can include, for example, a record of each transaction involving the bin 100 since the time it was created. Such transactions may include, for example, scans, database queries, updates such as restocking or removal of items, and so on. The virtual history can be output in the form of a report in response to a user request. In addition, the virtual history can be used to gather data or statistics that may be useful for planning future tasks such as bin 100 updates, item restocking, and so on.

Although FIG. 2A shows the RFID reading station 220 and the information processing system 210 as separate features, they are not required to be physically or functionally separate. For instance, information processing features can be included as part of the RFID reading station 220, such as the RFID reader 222. In general, the physical and functional implementation of information processing system 210 can be partitioned between various forms of hardware, software, firmware, etc.

With continued reference to the embodiment illustrated in FIG. 2A, the RFID reading station 220 can include the RFID reader 222 and the container 226. The RFID reader 222 can include a controller, such as a microprocessor or microcontroller, and an antenna 224. At least a portion of the antenna 224 can be located within the container 226 that is designed to receive the bin 100 during a read operation.

The RFID reader 222 can control the antenna 224 to communicate with RFID tags 104 associated with items of bin 100, as well as any RFID tag 106 associated with the bin 100 itself. In addition, the RFID reader 222 can receive and process communications received by the antenna 224 from the bin 100. Although RFID reader 222 is shown outside of container 226, it could alternatively be included within the container 226. Moreover, although the antenna is shown as being a part of the RFID reader 222, it will be understood that they could be separated into different components.

In a typical read operation, the RFID reader 222 controls the antenna 224 to interrogate any RFID tags within the container 226. Specifically, the RFID reader 222 causes the antenna 224 to emit a radio signal within the container 226. In response to the interrogation, the RFID tags communicate information to RFID reader 222 via antenna 224. In some cases, such as where the RFID tag is a passive RFID tag, the radio energy from the radio signal can further be used to energize the tag and enable it to emit a radio signal that includes the tag information. In certain cases, such as where the RFID tag is an active RFID tag, the RFID tag can include its own battery but can respond to the RFID reader 222 with its tag information. The tag information can include an ID or other information stored in memory on the RFID tag.

The communicated tag information can be associated with corresponding information stored in a database, such as national drug code (NDC) identifiers, lot numbers, and expiration dates for individual items, and a bin identifier for the bin 100 as a whole. The RFID reader 222 can communicate the received tag information to information processing system 210 for storage and/or further processing.

Dynamic RFID Tag Scanning

As described herein, the RFID reader 222 can control the antenna 224 to interrogate RFID tags within the container 226. In a typical read operation, however, prior to the interrogation, the RFID reader 222 is not aware of the presence of the RFID tags within the container 226. Rather, the RFID reader 222 and/or information processing system 210 can determine that a particular RFID tag is located within the container 226 based on the tag information received after the tag RFID has been interrogated. Often, the RFID reader 222 can "search" for RFID tags by transmitting an encoded radio signal for a predetermined period of time (for example, 2-4 seconds), and can determine which, if any, RFID tags are located within the container 226 based on received tag information.

However, in some cases, the predetermined period of time over which the RFID reader 222 searches for RFID tags is not of a sufficient duration to interrogate or energize each of the RFID tags present within the bin 100. As a non-limiting example, the bin 100 can include one or more RFID tags that are at least partially blocked or occluded from the interrogation (for example, by one or more items in the bin 100). Accordingly, the one or more RFID tags that are at least partially blocked or occluded may take longer (for example, longer than the predetermined period of time over which the RFID searches for tags) to register or receive the encoded radio signal from the RFID reader 222. As a result, although a particular RFID tag may be within a bin 100 or within a container 226, in some cases the RFID reader 222 and/or the information processing system 210 may not receive tag information from that particular RFID tag, and therefore may not determine that the particular RFID tag is within the bin 100 or the container to 226.

To address these and other problems, the RFID reader 222 can be configured to interrogate the pharmacy bin 100 for an increased period of time, which can be of a sufficient duration so as to acquire information from each RFID tag within the bin 100. In some embodiments, to improve the likelihood that each RFID tag within the bin is interrogated, the period of time over which the RFID reader 222 searches for RFID tags can be increased. For example, in some cases, the period of time can be increased to a longer predetermined period of time (for example, 20 seconds).

Alternatively, the period of time over which the RFID reader 222 searches for RFID tags can be dynamic rather than fixed or predetermined. For example, rather than a fixed duration of time over which the RFID scanner 222 interrogates or searches for RFID tags, the RFID scanner 222 can continue to scan for at least a predetermined time after each time it registers a new RFID tag. If the predetermined time period expires before a new RFID tag is registered, then the RFID scanner 222 can end the scan. However, if a new RFID tag is registered before the expiration of the predetermined time period, then the RFID scanner 222 can reset the predetermined time period and can continue to scan for RFID tags.

In general, if the bin 100 includes a plurality of RFID tags, then, due to a variety of factors (non-limiting examples: distance from the RFID reader 222, type of RFID tag, etc.), the RFID reader 222 can receive tag information from the various RFID tags at different time intervals. Furthermore, during the period over which the RFID reader 222 searches for RFID tags, the same tag may transmit tag information to the RFID reader multiple times. Accordingly, if multiple RFID are within the bin 100, when the RFID reader 222 interrogates the bin, the RFID reader can receive a plurality of messages from the RFID tags at various times, and at least some of those messages can be duplicate messages. In some cases, the RFID system can discriminate amongst the tag information to identify pharmacy items in the bin 100, and can identify and/or ignore duplicate messages, such as those messages from an RFID tag that have been processed and determined to be within the bin 100. If a new RFID tag is registered before the expiration of the predetermined time period, then the RFID scanner 222 can continue to scan and can restart a timer corresponding to the predetermined time period. If the time corresponding to the predetermined time period expires before a new RFID tag is registered, then the RFID scanner 222 can end the scan. Using this dynamic method of scanning, the system can ensure that all or most of the RFID tags within the bin 100 are given enough time to receive the radio signal received from the RFID reader and energize. This can be the case even if one or more RFID tags are blocked or occluded by other items in the bin 100.

Example Dynamic RFID Tag Scanning Routine

Figure 2B:
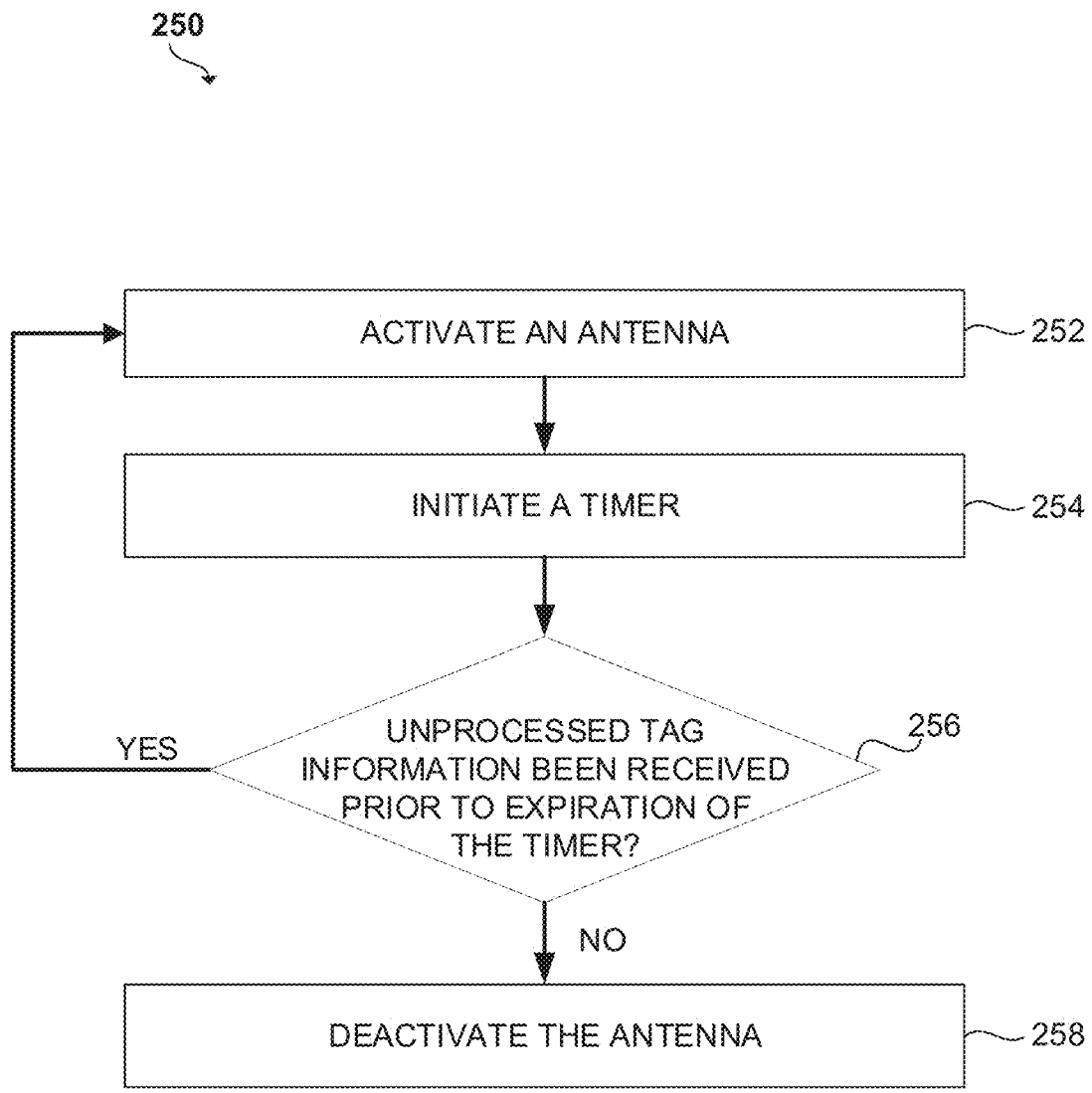
FIG. 2B is a flow diagram illustrative of an embodiment of a routine implemented by a system for dynamically scanning RFID tags.

FIG. 2B is a flow diagram illustrative of an embodiment of a routine 250 implemented by a system (such as system 200 of FIG. 2A) for dynamically scanning RFID tags. One skilled in the relevant art will appreciate that the elements outlined for routine 250 can be implemented by one or more computing devices or components that are associated with the system 200, such as the information processing system 210 or the RFID reader 222. Accordingly, routine 250 has been logically associated as being generally performed by the system 200. However, the following illustrative embodiment should not be construed as limiting. Furthermore, it will be understood that the various blocks described herein with reference to FIG. 2B can be implemented in a variety of orders. For example, the system 200 can implement some blocks concurrently or change the order as desired. Furthermore, it will be understood that fewer, more, or different blocks can be used as part of the routine 250. For example, in some embodiments, one or more of blocks 252, 254, 256, or 258 are not implemented. However, it will be understood that any of the blocks (and more or different blocks) can be implemented as part of routine 250.

At block 252, the system 200 activates an antenna 224 to search for RFID tags. For example, the system 200 can control or cause the antenna 224 to emit a radio signal. In some cases, as described herein, the antenna 224 can emit the radio signal within the container 226 to interrogate any RFID tags associated with items of the bin 100, as well as any RFID tag 106 associated with the bin 100 itself.

At block 254, the system 200 initiates (or re-initiates) a timer. In some cases, once initiated (or re-initiated), the timer can be configured to expire after a predetermined period of time has passed since initiation (or re-initiation). The counter can be a countdown timer, count up timer, or other timer. Further, the predetermined period of time can be any of various periods of time such as but not limited to less than a second, a few seconds, 5 seconds, 10 seconds, 15 seconds, 20 seconds, 30 seconds, etc. (+/−a few seconds). In some cases, the predetermined period of time can be configurable or selectable by a user. Alternatively, the predetermined period of time can be fixed.

As described above, prior to interrogation of the RFID tags, the system 200 is not aware of which, if any, RFID tags reside within the container 226. Instead, the system 200 can utilize the radio signal emitted from the antenna 224 to cause an RFID tag to transmit its tag information to the system 200. The system 200 can process the tag information to identify a bin, the pharmacy items in the bin, determine equivalences, or update item locations, among other things.

In some cases, a particular RFID tag can respond more than once to the radio signal(s) emitted by the antenna 224. For example, as the antenna 224 emits a radio signal over a period of time, the particular RFID tag may receive the radio signal multiple times and, as a result, sends its reply multiple times. In some cases, the system 200 can discriminate amongst the tag information to identify RFID tags that correspond to new or unprocessed RFID tags. For example, based on the tag information, the system 200 can identify and/or ignore duplicate messages, such as those messages (or tag information) that have already been processed. Further, in certain embodiments, the system 200 can instruct an RFID tag that has already responded to not respond further.

At block 256, the system 200 can determine whether unprocessed tag information has been received prior to the expiration of the timer. As a non-limiting example, new tag information can include tag information that has not been previous processed by the system 200, for example, since the time of the initial activation of the antenna (block 252). For example, as described above, a system 200 can receive tag information from an RFID tag multiple times. When the system 200 first receives the tag information, the system has not yet processed that tag information. Accordingly, that tag information can be identified as unprocessed, and the system 200 can process that tag information to identify a bin, the pharmacy items in the bin, determine equivalences, or update item locations, among other things. In contrast, when the system 200 receives that same tag information again (for example, via a duplicate message), the system has already processed that tag information, as described above. Accordingly, the duplicate tag information can be identified as processed tag information.

Referring to block 256, if new tag information has been received prior to the expiration of the timer that was initiated or re-initiated at block 254, then the system 200 can return to block 254 and re-initiate the timer. Moreover, the system 200 can continue to cause the antenna 224 to emit the radio signal such that it continues to search for RFID tags. However, if no new tag information has been received prior to the expiration of the timer, then the system 200 proceeds to block 258. At block 258, the system deactivates the antenna 224 such that it stops searching for RFID tags. In this way, the system can dynamically adjust the amount of time for which the antenna is activated. For example, if no tag information is received after five seconds and the timer is set for five seconds, then after ten seconds the system 200 can deactivate the antenna. With continued reference to the example, if no tag information is received after seven seconds, then the system 200 can deactivate the antenna after twelve seconds.

It will be understood that the various blocks described herein can be performed in a different sequence, can be added, merged, or left out altogether, and that the routine 250 can implement one or more of the blocks concurrently and/or change the order, as desired. For example, the routine 250 can concurrently activate the antenna (block 252) and initiate a timer (block 254). Alternatively, the routine 250 can initiate the timer (block 254) before activating the antenna (block 252).

Furthermore, it will be understood that fewer, more, or different blocks can be used as part of the routine for dynamically scanning RFID tags. As a non-limiting example, in some embodiments, the predetermined period of time can be adjusted (for example, extended or shortened) when or if the timer is re-initiated. For example, each time the system 200 returns to block 254 and re-initiates the timer, the predetermined period of time (e.g., the time that the system 200 will wait before proceeding to block 258 to deactivate the antenna) can be reduced, such as by one or more seconds. Alternatively, each time the system 200 returns to block 254 and re-initiates the timer, the predetermined period of time can be increased, such as by one or more seconds.

Example RFID Reading and Processing System

Figure 2C:
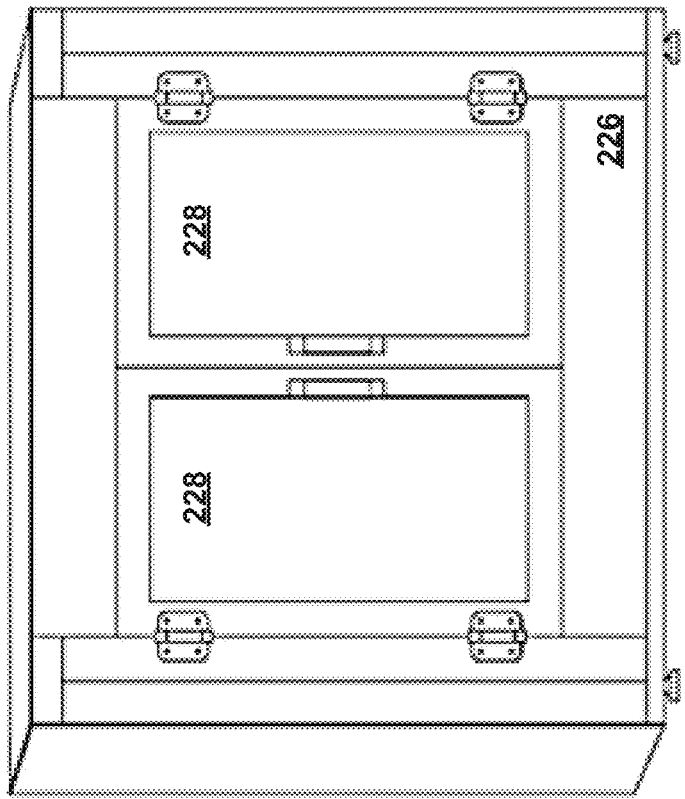
FIG. 2C is a schematic diagram illustrating an embodiment of the container with a pharmacy bin placed therein.
Figure 2C:
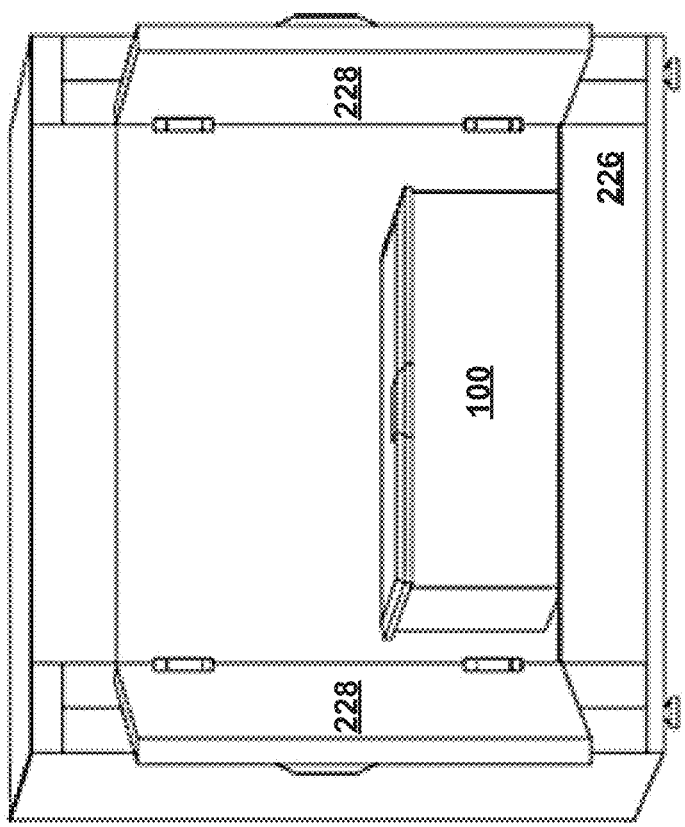

FIG. 2C is a schematic diagram illustrating an embodiment of the container 226 with a pharmacy bin 100 placed therein. In the illustrated embodiment of FIG. 2B, the container 226 comprises an enclosed space for receiving bin 100. The left side of FIG. 2B shows container 226 with doors 228 opened to receive bin 100, and the right side of FIG. 2B shows container 226 with doors 228 closed to perform a read operation. The use of an enclosed space allows RFID tags to be read without interference from objects in the surrounding environment, thereby avoiding false positives from RFID tags on items located in the pharmacy area. In some cases, container 226 can include electromagnetic shielding material, such as a metal, to provide electromagnetic shielding. For example, the entire container 226 can be made of electromagnetic shielding material. In addition or alternatively, the container 226 can include one or more layers of electromagnetic shielding material and/or one or more layers of non-electromagnetic shielding, such as plastic.

In some embodiments, the RFID reading station 220 or container 226 is restricted to receiving only one bin at a time. This restriction may be imposed in a variety of ways, for instance, by configuring an enclosure to accommodate only one bin or interrogating bin tags prior to scanning to ensure that no more than one bin tag is present. In certain embodiments, RFID reading station 220 may be specifically configured to allow concurrent scanning of multiple bins. For example, two bins can be placed in RFID reading station 220 or container 226 and scanned concurrently, or the RFID reading station 220 can include multiple containers 226 that include different pharmacy bins 100. In some cases, the system can analyze the data from the multiple bins separately.

Pharmacy Item Equivalence

Figure 3:
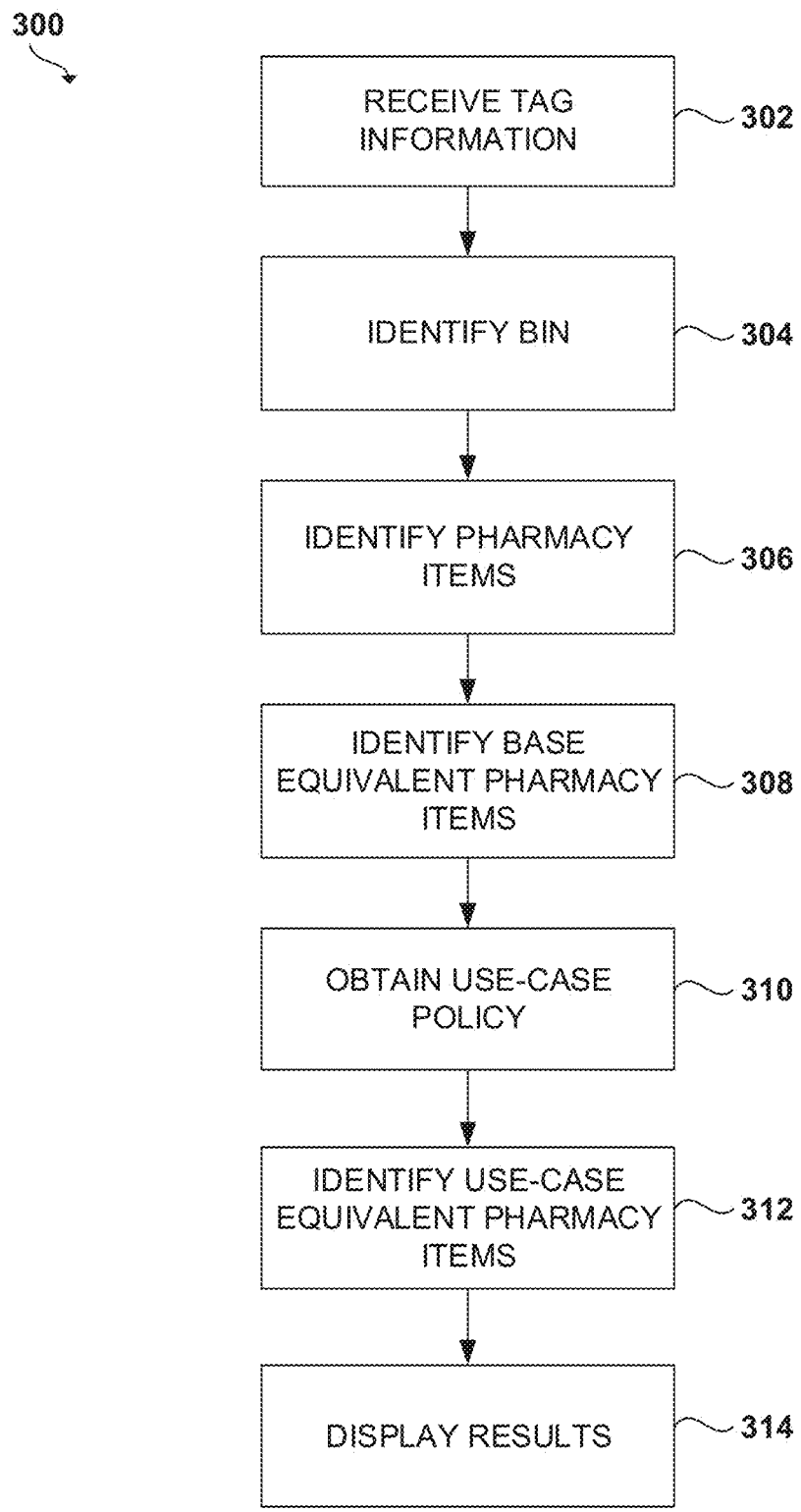
FIG. 3 is a flow diagram illustrative of an embodiment of a routine implemented by a system for determining equivalence between pharmacy items.

FIG. 3 is a flow diagram illustrative of an embodiment of a routine 300 implemented by a system (such as system 200 of FIG. 2A) for determining equivalence between pharmacy items. One skilled in the relevant art will appreciate that the elements outlined for routine 300 can be implemented by one or more computing devices or components that are associated with the system 200, such as the information processing system 210 or the RFID reader 222. In addition or alternatively, routine 300 can be implemented by one or more systems, such as the dispensing system 404, patient information system 406, administration system 408, or billing system 410 of FIG. 4. Accordingly, routine 300 has been logically associated as being generally performed by the system 200. However, the following illustrative embodiment should not be construed as limiting. Furthermore, it will be understood that the various blocks described herein with reference to FIG. 3 can be implemented in a variety of orders. For example, the system 200 can implement some blocks concurrently or change the order as desired. Furthermore, it will be understood that fewer, more, or different blocks can be used as part of the routine 300. For example, in some embodiments, one or more of blocks 302, 304, 306, 308, 310, 312, 314 are not implemented. However, it will be understood that any of the blocks (and more or different blocks) can be implemented as part of routine 300.

At block 302, the system 200 receives tag information from RFID tags. As described herein, tag information can include a unique tag serial number or product-related information, such as a stock number, lot or batch number, production date, or other specific information stored on the RFID tag(s) 104 or 106. In some embodiments, the receipt of tag information can be in response to an antenna 224 interrogating the RFID tag(s) 104 or 106 by emitting radio signals within the container 226. For example, the system 200 can cause the antenna 224 to emit a radio signal that activates the RFID tag(s) 104 or 106 and causes the RFID tag(s) 104 to respond with the tag information, or an indication thereof.

At block 304, the system 200 identifies a pharmacy bin 100 based at least in part on the received tag information. For example, as described herein, at least one RFID tag can be associated with the pharmacy bin 100 (non-limiting example: FIG. 1 illustrates the RFID tag 106 attached to the pharmacy bin 100). The system 200 can use the tag information from the associated RFID tag (for example, the RFID tag 106) to identify the pharmacy bin 100. For example, the tag information can include an identifier that corresponds to bin data stored in a database (non-limiting examples of bin data: data relating to types of pharmacy items that are to be included in the pharmacy bin 100, data relating to parameters for determining item equivalence, or data relating to a bin history (for example, items that were in the bin when last interrogated, items that were previously in the bin and later removed, etc.)). In some embodiments, the tag information can include the bin data.

At block 306, the system 200 identifies the pharmacy items present within the RFID tag reading station 220, within the container 226, and/or within the pharmacy bin 100. For example, as described herein, the tag information from the various RFID tags can include identifiers that correspond to pharmacy item data stored in a database. The system can use the identifiers to lookup the pharmacy item data and identify which, if any, pharmacy items are within the RFID tag reading station 220, within the container 226, and/or within the pharmacy bin 100.

The pharmacy item data can include various characteristics of the pharmacy item, as described herein, or can include other information, such as, but not limited to, the number of times a pharmacy item (or its RFID tag) has been scanned, the previous location(s) of the pharmacy item, users that have interacted with or used the pharmacy item or RFID tag, and/or the bin(s) with which the pharmacy item has been, or is, associated, expiration date, etc.

At block 308, the system 200 identifies base equivalent pharmacy items. In some cases, the system can identify the base equivalent pharmacy items by comparing one or more of various characteristics of the pharmacy items, such as but not limited to, product identifier, name(s), manufacturer, concentration, per-unit concentration, schedule, fill amount, package type, package size, route of administration, dosage form, etc.

The product identifier can refer to a unique identifier for the pharmacy item, such as, but not limited to a universal product identifier (UPI), national drug code (NDC), etc. The name can refer to the brand or generic name of a pharmacy item, or an active ingredient of a drug. The manufacturer can refer to the entity that manufactures the pharmacy item. If the pharmacy item is a drug, the manufacturer can refer to the drug manufacturer. The concentration can refer to the concentration of the pharmacy item, such as 20 mg/mL for a drug. The per-unit concentration can refer to the concentration by unit. For example, a drug with a concentration of 20 mg/20 mL would have a per-unit concentration of 1 mg/1 mL. The schedule for a pharmacy item can refer to the FDA schedule for drugs (e.g., Schedule 1-5).

The package size can refer to the size of the package or capacity for a package. For example, the package size for a vial could be expressed in the amount of mL that the vial can hold and the package size for pills could be expressed in the number pills that the container could hold, etc. The fill amount can refer to the amount of a pharmacy item in a pharmacy item container. For example, if a package size is 30 mL, but only 20 mL is in the pharmacy item container, then the fill amount can be 20 mL.

The package type for a pharmacy item can refer to how the pharmacy item is packaged, such as, but not limited to, ampule, atomizer, bag, blister pack, bottle (for example, plastic, glass, pump, spray, etc.), dropper, box, can, cup, cartridge, case, container (for example, plastic, glass, pump, etc.), inhaler, jar, pack, package, packet, pen, pouch, roll, syringe (for example, plastic, glass, etc.), strip, tube, tray, vial (for example, dispensing, multi-dose, bulk, single-dose, single-use, etc.), etc.

The route of administration can refer to the method in which the pharmacy item is administered to a patient, including, but not limited to, epcutaneous, epidural, gastrostomy, inhalational, intraarterial, intraarticular, intracardiac, intracerebral, intradermal, intramuscular, intraocular, intravesical, intravenous, nasal, oral, rectal, subcutaneous, sublingual and buccal, transdermal, transmucosal, etc.

The dosage form can refer to can refer to the form of the pharmacy items, including, but not limited to, aerosol, balm, capsule, cream, crystals, dermal patch, drops, ear drops, eye drops, gel, inhaler, intradermal, intramuscular, intraosseous, intraperitoneal, intravenous, liquid solution, liquid suspension, lotion, nebulizer, ointment, pastes, pill, powder/talc, skin patch, subcutaneous, suppository, tablet, vaporizer, etc.

In some embodiments, the system can determine that pharmacy items are base equivalent if the following characteristics match: route of administration, dosage form, and per-unit concentration, and/or if the following characteristics are comparable or similar: name (e.g., generic or brand or active ingredient correspond to each other) and package type. For example, the system can identify some package types as comparable (e.g., vial and ampule) and some package types are not comparable (e.g., vial and tabs). In certain embodiments, the system 200 can be size agnostic in determining base equivalence. For example, the system can determine that a vial of 10 mL of Propofol is base equivalent to a vial of 30 mL of Propofol.

At block 310, the system 200 obtains a use-case policy. In some cases, the system 200 can obtain the use-case policy based on the identified bin and/or based on results of the base equivalent pharmacy items. For example, the bin data can identify a specific use-case policy for the bin and/or the system can determine a use-case policy based on the similarity between the base equivalent pharmacy items. In certain embodiments, the system can prompt a user to enter or select the use-case policy. The use-case policy can correspond to a particular use case for the pharmacy items, such as but not limited to, storage in a bin, pharmacy kit creation, etc.

At block 312, the system 200 identifies use-case equivalent pharmacy items. In certain embodiments, the system uses the characteristics of the base equivalent pharmacy items and the use-case policy to identify use-case equivalent pharmacy items. In some case, the system can use more characteristics to determine the use-case equivalence than were used for the base equivalence. For example, in addition to having the same per-unit concentration, to identify pharmacy items as use-case equivalent, the system can require that the pharmacy items have the same concentration. In certain cases, the system can use preservative/no-preservative to determine use-case equivalence, but not to determine base equivalence. As a non-limiting example, one use-case policy can indicate that to be equivalent, pharmacy items must have the same concentration, package size, package type, and name. Another use-case policy can indicate that to be equivalent, all characteristics of the pharmacy items must be the same (e.g., same identifier, manufacturer, name, package size, package type, preservative/non-preservative, etc.). Accordingly, using the use-case policy, the system can identify pharmacy items that are use-case equivalent. Use-case policies can also or alternatively use package size vs. fill amount, package size, etc. to determine use-case equivalent pharmacy items.

At block 314, the system 200 causes a display to display the results. In some cases, the results can include an identification of some or all base equivalent pharmacy items that were scanned and/or use-case equivalent pharmacy items for one or more use cases. Further, the system 200 can identify the pharmacy items in the bin that were neither base equivalent nor use-case equivalent.

It will be understood that the various blocks described herein can be performed in a different sequence, can be added, merged, or left out altogether, and that the routine 300 can implement one or more of the blocks concurrently and/or change the order, as desired. For example, the routine 300 can concurrently identify the bin and identify the pharmacy items. Alternatively, the routine 300 can identify the pharmacy items (block 306) before identifying the bin (block 304). Similarly, the routine 300 can obtain a use-case policy (block 310) prior to identifying base equivalent pharmacy items (block 308), and routine 300 can identify base equivalent pharmacy items (block 308) and use-case equivalent pharmacy items (block 312) concurrently or in any order. In addition, the routine 300 can display results (block 314) at any point throughout the routine 300.

Furthermore, it will be understood that fewer, more, or different blocks can be used as part of the routine 300 to identify equivalent pharmacy items (or use-case equivalent pharmacy items). For example, in some embodiments, blocks 312 and 314 can be omitted such that the routine 300 identifies base equivalent pharmacy items without determining use-case equivalent pharmacy items. In addition or alternatively, block 308 can be omitted such that the routine 300 identifies use-case equivalent pharmacy items without identifying base equivalent pharmacy items.

Furthermore, in some embodiments, block 304 can be removed such that the information processing system does not identify the bin. In such embodiments, the information processing system can identify equivalence based at least in part on the pharmacy items found or identified within the RFID tag reading station. For example, a number of pharmacy items can be placed in the RFID tag reading station. After interrogation, the information processing system can identify which, if any, of the pharmacy items are equivalent to each other. In some cases, the routine 300 can identify different groups of pharmacy items that are equivalent. For example, the information processing system can identify a single group of equivalent pharmacy items and identify all other pharmacy items as not equivalent.

In certain embodiments, the routine 300 can determine different levels of equivalence. For example, a first level of equivalence can be based on an active ingredient in the drug, a second level of equivalence can be based on the active ingredient and concentration, and a third level can be based on the active ingredient, concentration, and one or more additional parameters, such as package type, volume, route of administration, etc. In certain cases, the different levels of equivalence can be used by the system to determine base equivalence and/or use-case equivalence. For example, in some cases, the system may determine a base equivalent based on a single level of equivalence, such as the first level of equivalence, while the system may determine the use-case equivalence based on multiple levels of equivalence, such as the first and second level, the second and third level, or the first and third levels of equivalence. Alternatively, in some cases, the system may determine a base equivalent based on multiple levels of equivalence and/or the use-case equivalence based on a single level of equivalence.

Health Care Data Across Different Systems

Medical service providers often use different systems located at various care sites to generate or monitor health care data (non-limiting examples: data related to events that occur in relation to a system, including event parameters such as drug identifiers, action identifiers, timing identifiers, patient identifiers, location identifiers, or the like). Being able to accurately associate (non-limiting examples: share, combine, match, relate, link, or the like) the events from the different systems can be important in effective health care management. However, as described herein, associating events can be complicated when patients receive care in multiple settings or when organizations and providers use different systems to share records electronically. Even within a single healthcare organization, the wide range of systems for clinical and administrative services can create obstacles to associating the events.

In general, a particular system can assign its own identifiers to each patient, provider, or pharmacy item whose data it maintains. However, among other things, a lack of uniformity in the management of data across the systems makes it challenging for a computing device to associate the health care data across multiple systems. For example, while individuals may use subjective criteria to associate events, the system 200 can utilize objective criteria to associate events, and it can be challenging to accurately associate events using objective criteria when the data is not uniformly managed. As a non-limiting example, use of a first system to track a dispensing event (non-limiting example: the dispensing of a medication) and a second, different system to track an administration event (non-limiting example: the administration of the medication) can make it difficult to associate events, even though these events may be associated with the same patient, same drug, same provider, etc. Furthermore, the different systems can increase the challenge in identifying waste, identifying missing medications, or identify duplicate items or entries, which can increase the costs for the medical service providers or can lead to fraud or drug abuse, among other things.

To further complicate medication tracking, the different systems may store different information about the patient or pharmacy item that may overlap but is not identical. Thus, for example, it can be difficult to determine whether an administered medication or a discarded medication corresponds to a dispensed medication.

Efforts to address these and other difficulties that arise from the use of different systems to generate or monitor health care data are further complicated by the need to protect patient privacy and security. For example, the communication of protected health information (PHI) (non-limiting examples: demographic information, medical histories, test and laboratory results, mental health conditions, insurance information, and other data that a healthcare professional collects to identify an individual and determine appropriate care) is highly regulated. Thus, it can be difficult to associate events or other data between the different systems without communicating PHI.

Figure 4:
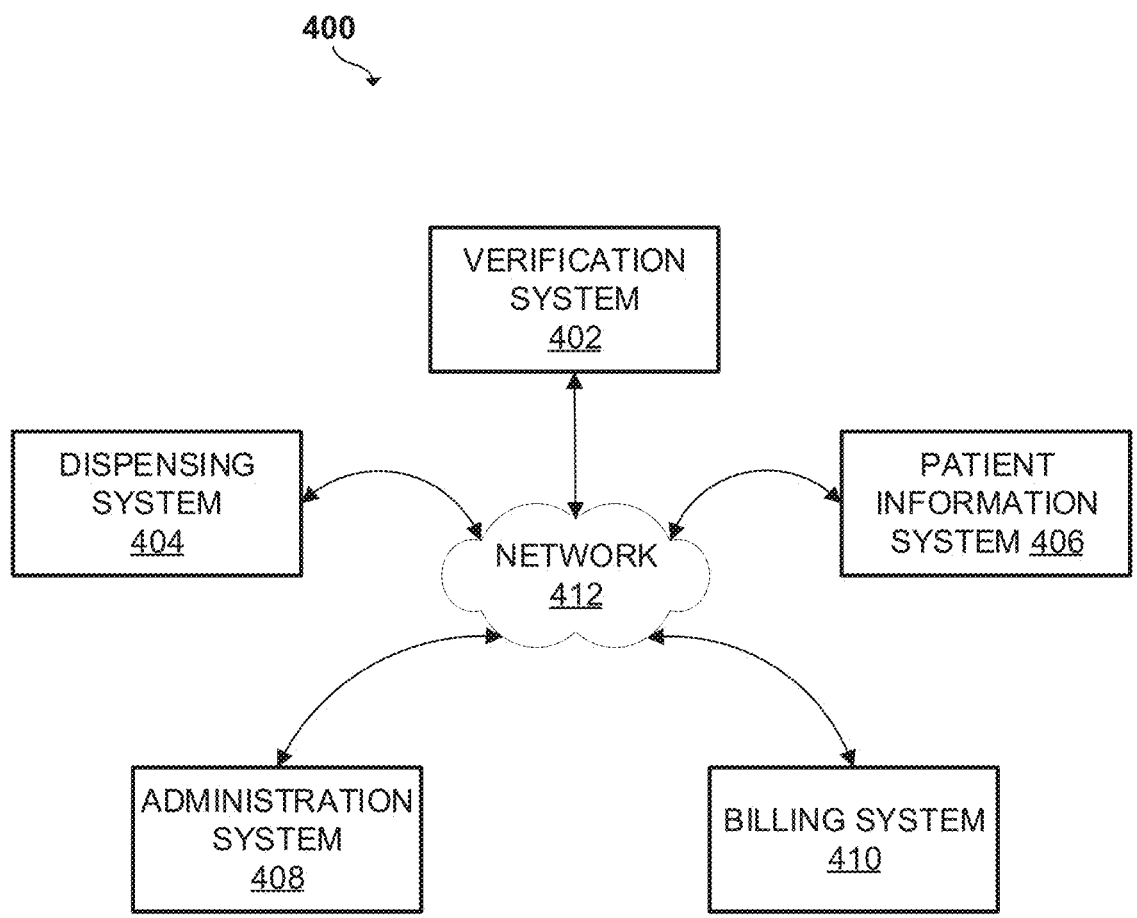
FIG. 4 is a block diagram illustrating an embodiment of a verification environment for associating information across multiple health care systems.

FIG. 4 is a block diagram illustrating an embodiment of a verification environment 400 for associating information across multiple health care systems. In some cases, the association is HIPAA-compliant. In the illustrated embodiment, the verification environment 400 includes a verification system 402, a dispensing system 404, a patient information system 406, an administration system 408, and a billing system 410, each communicably connected via network 412.

The dispensing system 404 can be implemented in a variety of ways and can include one or more computers, servers, virtual machines, or the like. In certain embodiments, the dispensing system 404 communicates with other systems (for example, the verification system 402, patient information system 406, administration system 408, or billing system 410) via one or more networks 412, such as a local or wide area network. In some cases, the dispensing system 404 can be implemented using a local computing device, such as a processor or computer, or on a remote computing device, such as a server that communicates with a local computing device via a local or wide area network.

The dispensing system 404 can be configured include one or more processing devices or data stores for controlling or tracking the dispensing, wasting, returning, or transferring of drugs. In some cases, dispensing system 404 is configured to store, dispense, or receive medications while controlling or tracking drug distribution. Example non-limiting embodiments of the dispensing system 404 include one or more of various drug dispensing cabinets (non-limiting example: an automated dispensing medication cabinet (ADCs)), carousels, kits, pick pickers, box pickers, or the like.

The dispensing system 404 can be configured to store drugs (such as, but not limited to, tablets, cartridges, creams, crystals, powder, fluid, film, gel, etc.) for dispensing. For example, the dispensing system 404 can include a computerized drug storage device or cabinet and can be configured to dispense precise amounts of a particular drug or determined drug equivalent. In some cases, the dispensing system 404 can dispense a drug in response to a request from a user. For example, a user can request to receive a particular amount of a drug from a drug dispensing cabinet or other dispensing location, and the drug dispensing cabinet or other dispensing location can dispense the drug.

The dispensing system 404 can identify, track, or communicate dispensing data. For example, the dispensing system 404 can identify, track, or communicate dispensing event parameters such as, but not limited to, a drug identifier of the dispensed drug (non-limiting examples: drug name, drug quantity, drug concentration, package size, or other drug identifying information), an action identifier (non-limiting example: in indication of the dispensing event), a timing identifier (non-limiting examples: a time or date associated with the dispensing event), a patient (or the intended recipient of the drug) identifier (non-limiting examples: patient name, birth date, height, weight, social security number, or other patient information), provider identifier (non-limiting examples: nurse, doctor, or provider name, or other provider information indicative of the user(s) that requested or received the drug), or a location identifier (non-limiting examples: a care area associated with the provider or the patient, a location of the dispensing event, etc.).

In a typical scenario, the amount of drug dispensed from the dispensing system 404 is the same amount of the drug that is administered to the patient. However, in some circumstances (non-limiting examples: the user requested too much of the drug to be dispensed, the dispensing system dispensed too much of the drug, the patient's requirements changed, or the like), the amount of the drug that is dispensed is not equal to the amount of the drug that is administered. In other words, there is a portion of the drug that remains or is leftover after the drug was administered to the patient. In circumstances such as these, this remaining portion of the drug should be properly disposed of or returned.

As such, in some implementations, the dispensing system 404 (or another system such as a waste system or a return system) can be configured to receive drugs (such as, but not limited to, tablets, cartridges, creams, crystals, powder, fluid, film, gel, etc.) for discarding or returning. For example, the dispensing system 404 can include a computerized drug storage device or cabinet and can be configured to receive and track precise amounts of a particular drug to be disposed of or returned for re-use. In some cases, the dispensing system 404 can receive a drug in response to a request from a user. For example, a user can request to dispose of or return a particular amount of a drug into a bin or other location, and the bin can receive and/or store the drug.

In some cases, the dispensing system 404 can identify, track, or communicate waste and/or return event data. For example, the dispensing system 404 can identify, track, or communicate waste event parameters and/or return event parameters such as, but not limited to: a drug identifier of the wasted/returned drug (non-limiting examples: drug name, drug quantity, drug concentration, package size, or other drug identifying information), an action identifier (non-limiting example: in indication of the waste/return event), a timing identifier (non-limiting examples: a time or date associated with the waste/return event), a patient (or the intended recipient of the drug) identifier (non-limiting examples: patient name, birth date, height, weight, social security number, or other patient information), provider identifier (non-limiting examples: nurse, doctor, or provider name, or other provider information indicative of the user(s) that returned/wasted the drug), or a location identifier (non-limiting examples: a care area associated with the provider or the patient, a location of the waste/return event, etc.). In some cases, to return or dispose of a drug, a provider may need someone to witness him/her performing the wasting or returning. Accordingly, in some cases, the waste and/or return event parameters can include a witness identifier. In some cases, the witness identifier can be included in or with the provider identifier.

In some cases, the dispensing system 404 can collect or track information associated with pharmacy items in a pharmacy kit that is checked out from a pharmacy. Similarly, the dispensing system 404 can collect or track information associated with a drug when the drug is returned to a pharmacy or cabinet, wasted, or transferred between persons, etc.

Additional or alternative non-limiting examples of dispensing or tracking systems are described in U.S. Pub. No. 2015/0142469, filed Jan. 23, 2015, entitled "Management of Pharmacy Kits," and U.S. Pub. No. 2017/0212993, filed Feb. 7, 2017, entitled "Medication Tracking," each of which is hereby incorporated herein by reference in its entirety. Furthermore, although only one dispensing system 404 is shown in FIG. 4, it will be understood that the environment 400 can include multiple dispensing system. Moreover, in some cases, the dispensing system 404 can be separated into multiple distinct systems, such as a waste management system configured to store and track wasted or disposed drugs, a return management system configured to store and track returned drugs, and/or a different system for track and dispensing drugs.

The administration system 408 can be implemented in a variety of ways and can include one or more computers, servers, virtual machines, or the like. In certain embodiments, the administration system 408 communicates with other systems (for example, the verification system 402, dispensing system 404, patient information system 406, or billing system 410) via one or more networks 412, such as a local or wide area network. In some cases, the administration system 408 can be implemented using a local computing device, such as a processor or computer, or on a remote computing device, such as a server that communicates with a local computing device via a local or wide area network.

The administration system 408 can include one or more processing devices or data stores for controlling or tracking the administration of drugs to a patient. For example, as described herein, one or more drugs can be dispensed from a dispensing system, and at least some of the dispensed drug can be administered to a patient. The administration system 408 can identify, track, or communicate administration event data. For example, the administration system 408 can identify, track, or communicate administration event parameters such as, but not limited to: a drug identifier of the administered drug (non-limiting examples: drug name, drug quantity, drug concentration, package size, or other drug identifying information), an action identifier (non-limiting example: in indication of the administration event), a timing identifier (non-limiting examples: a time or date associated with the administration event), a patient (or the recipient of the drug) identifier (non-limiting examples: patient name, birth date, height, weight, social security number, or other patient information), provider identifier (non-limiting examples: nurse, doctor, or provider name, or other provider information indicative of the user(s) that administered the drug), or a location identifier (non-limiting examples: a care area associated with the provider or the patient, a location of the administration event, etc.).

In some cases, the administration system 408 can automatically track or identify the amount of the drug that was administered to the patient. In addition or alternatively, the administration system 408 can receive an input (for example, from the user that administered the drug or from a user that watched the administration) that identifies the drug, amount administered, the user that administered the drug, or the like.

In some implementations, the one or more processing devices or data stores of the administration system 408 can be configured to store electronic medical records (EMRs). One non-limiting example of an EMR system is described in U.S. Pat. No. 5,924,074, incorporated herein by reference. In addition or alternatively, the one or more processing devices or data stores of the administration system 408 can be configured for storing information related to admissions, discharges, transfers, etc. of patients. For example, the administration system 408 can be configured to store information or identifiers corresponding to one or more patients such as, but not limited to, name, birth date, height, weight, medical history, health issues, allergies, prescriptions, treatments, drug administrations, social security number, admissions, discharges, transfers, etc.

The patient information system 406 can be implemented in a variety of ways and can include one or more computers, servers, virtual machines, or the like. In certain embodiments, the patient information system 406 communicates with other systems (for example, the verification system 402, dispensing system 404, administration system 408, or billing system 410) via one or more networks 412, such as a local or wide area network. In some cases, the patient information system 406 can be implemented using a local computing device, such as a processor or computer, or on a remote computing device, such as a server that communicates with a local computing device via a local or wide area network.

The patient information system 406 can include one or more processing devices or data stores for storing or tracking patient information. For example, the patient information system 406 can be configured to store information related to admissions, discharges, transfers, etc. of patients such as, but not limited to, patient name, birth date, height, weight, medical history, health issues, allergies, prescriptions, treatments, drug administrations, social security number, admissions, discharges, transfers, etc. In addition or alternatively, the patient information system 406 can be configured to store EMRs. Example non-limiting embodiments of an EMR system are described in U.S. Pat. No. 5,924,074, filed Sep. 27, 1996, entitled "Electronic Medical Records System," which is hereby incorporated herein by reference in its entirety.

The billing system 410 can be implemented in a variety of ways and can include one or more computers, servers, virtual machines, or the like. In certain embodiments, the billing system 410 communicates with other systems (for example, the verification system 402, dispensing system 404, patient information system 406, or administration system 408) via one or more networks 412, such as a local or wide area network. In some cases, the billing system 410 can be implemented using a local computing device, such as a processor or computer, or on a remote computing device, such as a server that communicates with a local computing device via a local or wide area network.

The billing system 410 can include one or more processing devices or data stores for storing information related to the billing for the use of the medications. For example, the billing system 410 can be configured to store patient information related to admissions, discharges, transfers, or drug administration, such as, but not limited to, patient name or other identifier, prescriptions, treatments, drug administrations, admissions, discharges, or transfers.

The verification system 402 can include one or more processing devices or data stores and can be configured to associate information (such as date related to events) between or from one or more of the dispensing system 404, the patient information system 406, the administration system 408, and/or the billing system 410. For example, the verification system 402 can be communicatively coupled with one or more of the dispensing, patient information, administration, or billing systems 404-410 via one or more networks 412. In some implementations, the one or more networks 412 correspond to a local area network (LAN) or wide area network (WAN).

The verification system 402 can be configured to share, combine, aggregate, match, relate, or link data associated with one or more of the different systems 404, 406, 408, or 410. For example, as described herein, each of the systems 402, 404, 406, 408, or 410 can be communicatively coupled via a network 412, and the verification system 402 can receive events or other data corresponding to one or more of the systems 404, 406, 408, or 410 via the network 412. In addition or alternatively, in certain embodiments, the verification system 402 can receive data associated with one or more systems 404, 406, 408, or 410 via an intermediary, such as a portable memory device, CD, etc.

The verification system 402 can be configured to associate (non-limiting examples: share, combine, aggregate, match, relate, or link) any of the various systems' data as described herein. For example, the verification system 402 can be configured to associate one or more sets of events (non-limiting examples: dispensing events, administrating events, waste events, return events, billing events) from the various systems. In some cases, each event associated with a system can include plurality of event parameters including, but not limited to, a drug identifier, an action identifier, a timing identifier, a patient identifier, a provider identifier or a location identifier. In addition or alternatively, verification system 402 can be configured to associate EMRs, patient identifying information, user identifying information (for example, the user that dispense, administered, or discarded a drug), or the like.

As described herein, for example with respect to FIGS. 1-2B, in some cases, the verification system 402 can be configured to identify equivalent drugs between one or more of the dispensing system 404, the patient information system 406, the administration system 408, or the billing system 410. Furthermore, as described herein, for example with respect to FIG. 9, in some cases, the verification system 402 can be used to identify pharmacy item discrepancies between one or more of the dispensing system 404, the patient information system 406, the administration system 408, or the billing system 410.

It will be understood that the verification system 402 can be implemented in a variety of ways. For example, the verification system 402 can include, but is not limited to, one or more processors, computers, servers, virtual machines, or the like. In addition or alternatively, the verification system 402 can include one or more of a local computing device (such as a processor or computer located in the same room as the dispensing system 404 and/or the administration system 408) or on a remote computing device (such as a server that communicates with the dispensing system 404 and/or the administration system 408 via a local or wide area network). In some embodiments, the verification system 402 can be included as part of the dispensing system 404, patient information system 406, administration system 408, or billing system 410.

Although only one system of each type is shown in FIG. 4, it will be understood that the environment 400 can include multiple systems of each type, such as multiple dispensing systems 404, patient information systems 406, administration systems 408, or billing systems 410, each of which can be communicatively coupled to each other and/or with the verification system 402 via one or more networks 412.

Pharmacy Item Tracking

Figure 5:
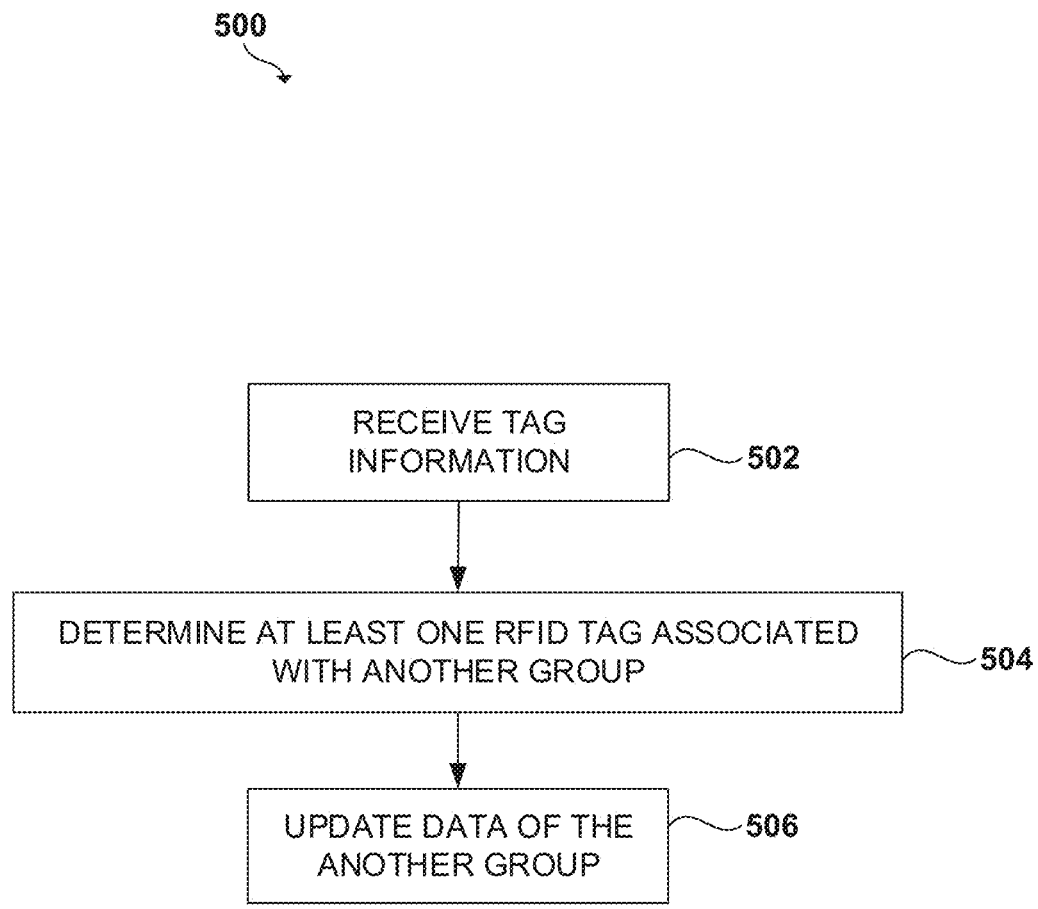
FIG. 5 is a flow diagram illustrative of an embodiment of a routine for tracking pharmacy items.

FIG. 5 is a flow diagram illustrative of an embodiment of a routine 500 for tracking pharmacy items. One skilled in the relevant art will appreciate that the elements outlined for routine 500 can be implemented by a system, such as the RFID reading and processing system 200, verification system 402, dispensing system 404, patient information system 406, administration system 408, or billing system 410, or one or more computing devices or components or a system, such as the information processing system 210 and/or the RFID reader 222. For simplicity, the routine 500 has been logically associated as being generally performed by the system 200. However, the following illustrative embodiment should not be construed as limiting. Furthermore, it will be understood that the various blocks described herein with reference to FIG. 5 can be implemented in a variety of orders. For example, the system 200 can implement some blocks concurrently or change the order as desired. Furthermore, it will be understood that fewer, more, or different blocks can be used as part of the routine 500. For example, in some embodiments, one or more of blocks 502, 504, or 506 are not implemented. However, it will be understood that any of the blocks (and more or different blocks) can be implemented as part of routine 500.

At block 502, the system 200 receives tag information from RFID tags. In some embodiments the receipt of tag information can be in response to the antenna 224 emitting radio signals within the container 226, as described in greater detail herein. For example, the system 200 can cause the antenna 224 to emit a radio signal that activates the RFID tags and causes them to respond with the tag information.

At block 504, the system 200 determines that at least one pharmacy item is associated with a different group of pharmacy items and/or in a different bin. As described herein, in some cases, the tag information from the various RFID tags can include IDs that correspond to pharmacy item data stored in a database. The system can use the IDs to lookup the pharmacy item data and identify the pharmacy items that are present in the bin. In certain embodiments, the tag information can include the pharmacy item data.

In some cases, as described above, the pharmacy item data can include historical information regarding the corresponding pharmacy item. For example, the pharmacy item data can indicate the number of times the pharmacy item (or its RFID tag) has been scanned, the previous locations of the pharmacy item, and/or the bin(s) with which the pharmacy item has been, or is, associated. The system can use the historical information to determine whether a pharmacy item is associated with a different location and/or a different bin.

At block 506, the system 200 can update the pharmacy item data so that the pharmacy item is associated with a current location or bin. For example, if the pharmacy item data indicates that the pharmacy item is associated with an RFID reading station at a different location, the system 200 can update the pharmacy item data to indicate that the pharmacy item is no longer located at the other location and/or that the pharmacy item is located at a new location. Similarly, if the pharmacy item data indicates that the pharmacy item is associated with a different bin, the system 200 can update the pharmacy item data to indicate that the pharmacy item is no longer associate or located in the different bin and/or that the pharmacy item is located in or associated with a new bin.

It will be understood that the various blocks described herein with respect to routine 500 can be performed in a different sequence, can be added, merged, or left out altogether, and that the routine 500 can implement one or more of the blocks concurrently and/or change the order, as desired. Furthermore, it will be understood that fewer, more, or different blocks can be used as part of the routine 500 to track pharmacy items. For example, in some embodiments, block 506 can be omitted such that the routine 500 identifies at least one RFID tag associated with another group, but does not update data of the another group. Rather, the routine 500 can cause a display to display an indication to move the identified RFID tag to the bin or group to which is associated.

Pharmacy Item Tracking Between Systems

Figure 6:
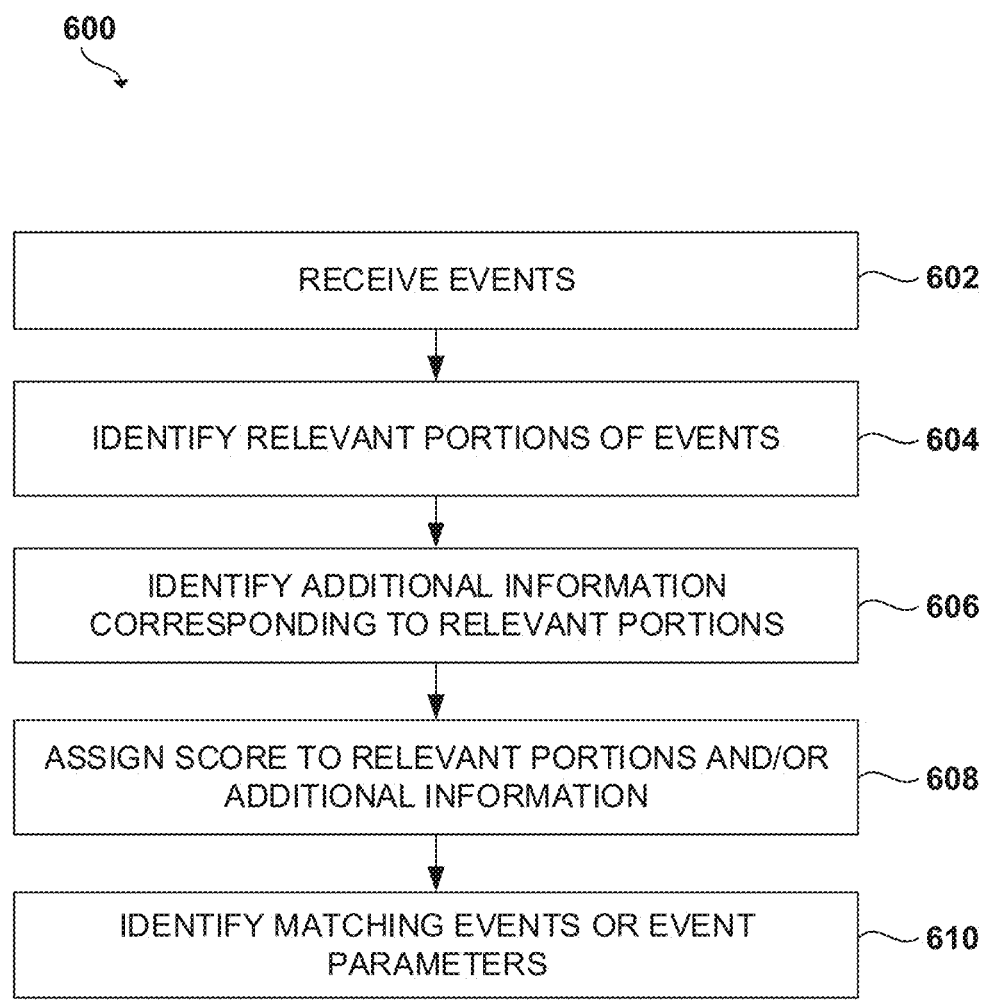
FIG. 6 is a flow diagram illustrative of an embodiment of a routine to identify matching events from different systems of an environment.

FIG. 6 is a flow diagram illustrative of an embodiment of a routine 600 to identify matching events from different systems of an environment, such as environment 400. One skilled in the relevant art will appreciate that the elements outlined for routine 600 can be implemented using any one or any combination of the systems in the environment 400, such as the verification system 402, dispensing system 404, patient information system 406, administration system 408, or billing system 410. For simplicity, the routine 600 has been logically associated as being generally performed by the verification system 402. However, the following illustrative embodiment should not be construed as limiting. Furthermore, it will be understood that the various blocks described herein with reference to FIG. 6 can be implemented in a variety of orders. For example, the system 406 can implement some blocks concurrently or change the order as desired. Furthermore, it will be understood that fewer, more, or different blocks can be used as part of the routine 600. For example, in some embodiments, one or more of blocks 602, 604, 606, 608, or 610 are not implemented. However, it will be understood that any of the blocks (and more or different blocks) can be implemented as part of routine 600.

At block 602, the verification system 402 receives sets of events from one or more systems, such as the dispensing system 404, patient information system 406, administration system 408, and/or billing system 410. Each event of the set of events can include a plurality of event parameters, such as a drug identifier, an action identifier, a timing identifier, a patient identifier, a provider identifier or a location identifier, as described herein. The events can correspond to data entries in the different systems, such as drug dispensing or administration entries, an electronic medical record entry, billing information for a drug, or the like.

At block 604, the verification system 402 identifies relevant portions of the events to be used for mapping between systems. For example, in some cases, the relevant portions can include one or more event parameters, such as a drug identifier, an action identifier, a timing identifier, a patient identifier, a provider identifier or a location identifier, or a combination thereof. However, it will be understood that other portions of the event can be used.

At block 606, the verification system 402 identifies additional information corresponding to the relevant portions or event parameters. For example, if the event parameter is a drug name, the verification system 402 can identify other names for the drug (for example, generic or brand name(s), active ingredient, etc.), substitutes for the drug, medical descriptions of the drug (for example, description of drug in a dictionary encyclopedia, drug reference document, etc.). As another example, if the relevant portion is a provider name, the verification system 402 can identify a care area (non-limiting examples: ER, OR, ICU, etc.) associated with the provider.

At block 608, the verification system 402 assigns a score or numeric value to the identified relevant portions and/or the additional information. For example, in some cases, the score assigned to the relevant portions and/or the additional information can be based at least in part on the relevant portion's (or the additional information's) similarity to the terms found in a training or normalization database. For example, when a relevant portion is similar to or matches a word in the normalization database, that relevant portion can be assigned a relatively higher or better score. Similarly, when the additional information is similar to or matches a word in the normalization database, that additional information can be assigned a relatively higher or better score. In contrast, relevant portions and/or the additional information that are dissimilar to the words found in the normalization database can be assigned lower values.

As a non-limiting example, and continuing with the example above, if the relevant portion is a drug name, the verification system 402 can assign a score to the name of the drug identified in the relevant portion based on its comparison to the normalization database. Furthermore, the verification system 402 can assign a score to the additional information (e.g., other names for the drug), and/or to a description of the drug found in the event. In some cases, the verification system 402 can assign a score to each separate word in the description or to multiple words in the description (for example, not assign a score to "the" "or"), such as medically related terms in the description.

At block 610, the verification system 402 identifies matching events or event parameters based on the scores assigned to the relevant portions and/or the additional information. The matched events or event parameters can correspond to event parameters identified in a normalization database, normalized event parameters, or events from other systems. For example, using the score assigned to the relevant portions and/or the additional information, the verification system 402 can build or generate an identifier for the relevant portions. In some cases, the identifier can include the score for the relevant portions and the score for each piece of additional information that relates to the relevant portions. The generated identifier for a relevant portion of an event from one system can be compared to the generated identifiers for relevant portions and/or additional information of events from a different system or from a normalization database. The identifiers that are most similar can be identified as a match. This process can be repeated for the relevant portions of each event from the system until all of the relevant portions of the events from one system are mapped or matched with the relevant portions of events from a different system, or are normalized with a normalized event parameter. For example, the process can continue until all drug names from one system are mapped to or match the drug names in a second system or are normalized or mapped to a normalized drug name (or event parameter).

It will be understood that the various blocks described herein with respect to routine 600 can be performed in a different sequence, can be added, merged, or left out altogether, and that the routine 600 can implement one or more of the blocks concurrently and/or change the order, as desired. For example, in some cases, the verification system 402 can review the relevant portions and remove duplicates. In some cases, the events, score, relevant portions, additional information, or the like can be stored in a data store for later retrieval. Furthermore, in some embodiments, block 606 can be omitted such that routine 600 does not identify additional information corresponding to the relevant portions. Accordingly, the routine 600 can assign a score to the relevant portions and can identify the related events based off the assigned score and/or the relevant portions.

As described herein, in some cases, to normalize an event, the system can map or match data received from a first system to normalized data in a normalization database. Accordingly, when a match is identified, the system can replace the event parameter with the normalized event parameter or include the normalized event parameter as part of a normalized event.

Event Tracking Between Systems

Figure 7:
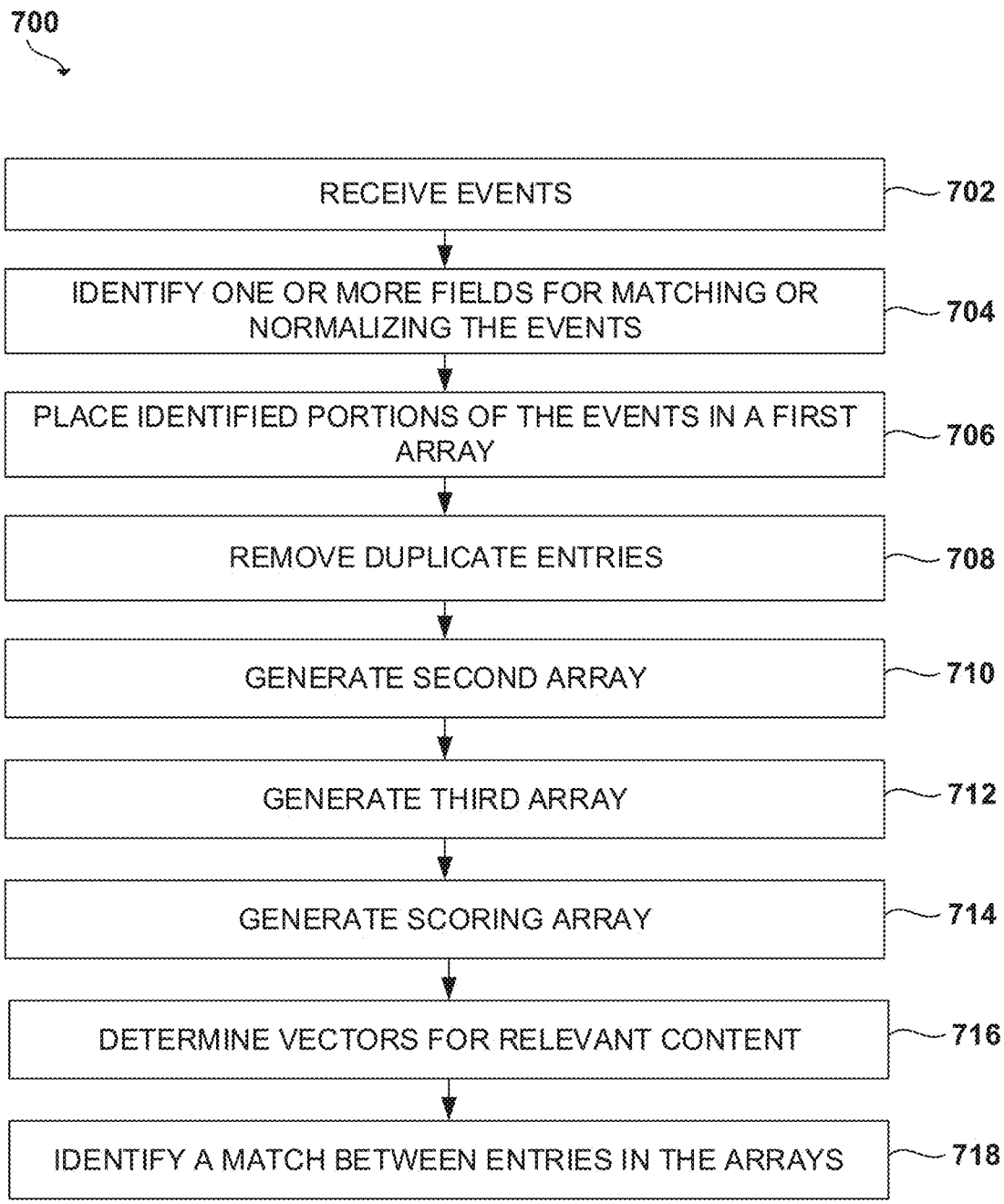
FIG. 7 is a flow diagram illustrative of an embodiment of a routine to match events from the systems of an environment.

FIG. 7 is a flow diagram illustrative of an embodiment of a routine 700 to match events from the systems of an environment, such as environment 400. One skilled in the relevant art will appreciate that the elements outlined for routine 700 can be implemented using any one or any combination of the systems in the environment 400, such as the verification system 402, dispensing system 404, patient information system 406, administration system 408, or billing system 410. For simplicity, the routine 700 has been logically associated as being generally performed by the verification system 402. However, the following illustrative embodiment should not be construed as limiting. Furthermore, it will be understood that the various blocks described herein with reference to FIG. 7 can be implemented in a variety of orders. For example, the system 406 can implement some blocks concurrently or change the order as desired. Furthermore, it will be understood that fewer, more, or different blocks can be used as part of the routine 700. For example, in some embodiments, one or more of blocks 702-718 are not implemented. However, it will be understood that any of the blocks (and more or different blocks) can be implemented as part of routine 700.

At block 702, similar to block 602 of FIG. 6, the verification system 402 receives one or more events from one or more systems. The events can be received via a network 412 or via an alternate medium, such as a portable electronic storage device.

At block 704, the verification system 402 identifies one or more fields for matching or normalizing the events. For example, each event can include a plurality of event parameters, such as a drug identifier, an action identifier, a timing identifier, a patient identifier, a provider identifier or a location identifier, and/or other data. Based on the systems with data to be matched or the content of a normalized field, the system can determine which of the fields of the received event are to be retained and which are to be discarded. For example, in some cases, the system can remove the fields, event parameters, or other data that is not to be used to match events or does not correspond to content of a normalized event. In some cases, rather than removing data from events, the verification system 402 can disregard the information when it matches events between the systems or normalizes the event.

At block 706, the verification system 402 places the identified portions of the events from one system into a first array (for example, array 1 of system 1 or A1S1). The identified portions of events from another system can be placed in a second, different array (for example, A1S2).

In some cases, the different systems may have recorded the same event, and thus one or more of the arrays can have the same or similar information. Accordingly, at block 708, the verification system 402 removes duplicate entries from the arrays. For example, the verification system 402 can compare the first and second array to check for similarities. If the verification system 402 determines that the first and second arrays satisfy a threshold similarity level, then the system can remove or ignore one of the entries as a duplicate. In some cases, the threshold similarity levels can include one or more matching or substantially similar event parameters. For example, if the first and second arrays each include entries having a same drug identifier, patient identifier, time identifier, and action identifier, then the verification system 402 can classify the entries as duplicates and can ignore or more one of the duplicate entries.

At block 710, for A1S1, the verification system 402 generates a second array (A2S1) that includes one or more synonyms or alternate names or spelling for one or more entries in the A1S1. For example, if A1S1 includes an entry "ibuprofen," the second array can include entries for "Advil," "NeoProfen," "Caldolor," "Motrin IB," "isobutylphenylpropionic acid," etc. The verification system 402 can include an indication that these entries relate to the "ibuprofen" entry in A1S1. In certain embodiments, each entry in A2S1 is related to one entry in A1S1, however, an entry in A1S1 can be related to multiple entries in A2S1.

At block 712, for A1S1, the verification system 402 generates a third array (A3S1) that includes additional information for one or more entries in A1S1. With continued reference to the "ibuprofen" entry above, A3S1 can include entries for "nonsteroidal," "anti-inflammatory," "treatment" "pain," "fever," etc. Similar to A2S1, each entry in A3S1 can be related to one entry in A1S1, however, an entry in A1S1 can be related to multiple entries in A3S1. The additional information can correspond to information obtained from additional resources, such as dictionaries, encyclopedias, drug reference documents, etc. In certain cases, when multiple resources are used, A3S1 can include duplicates of some entries. For example, if two resources include the term "nonsteroidal," "anti-inflammatory," for "ibuprofen," A3S1 can include an entry for each resource that includes that term.

At block 714, for each of A1S1, A2S1, and A3S1, the verification system 402 generates a scoring array (e.g., B1S1, B2S1, B3S1) that includes a score for each entry in the respective array. With continued reference to the "ibuprofen" example, the scoring arrays can include a score for "ibuprofen," "Advil," "NeoProfen," "Caldolor," "Motrin TB," "isobutylphenylpropionic acid," "nonsteroidal," "anti-inflammatory," "treatment" "pain," "fever," etc. In some cases, the scores can be based on the similarity of the entry with an entry in a normalization database. In some embodiments, the normalization database includes a list of drugs. However, for embodiments in which other content from the messages corresponds to the relevant content used for mapping, the normalization database can include additional or different information.

At block 716, for each entry in A1S1, the verification system 402 determines a vector based on the scores in the entries of B1S1, B2S1, B3S1 that are associated with the particular entry in A1S1. With continued reference to the "ibuprofen" example, the verification system 402 can generate a vector based on the score assigned to "ibuprofen," "Advil," "NeoProfen," "Caldolor," "Motrin IB," "isobutylphenylpropionic acid," "nonsteroidal," "anti-inflammatory," "treatment" "pain," "fever," a score assigned to a subset thereof. The vector can include the score for each entry and/or a combination of the scores, such as an average, a cosine similarity, etc.

At block 718, the verification system 402 identifies a match between entries in the arrays A1S1 that correspond to system 1 with entries in the arrays A1S2 that correspond to system 2 based on the generated vectors. In some cases, to identify the match, the system compares the vector of one entry in the array A1S1 with the vector of each entry in the array A1S2. In some cases, the entries with vectors that are the most similar are considered a match. In certain embodiments, the verification system 402 uses a cosine similarity function to identify matches. For example, the cosine similarity between two vectors can be a measure that calculates the cosine of the angle between them. Accordingly, cosine similarity can generate a metric that identifies how related two vectors are by looking at the angle of the vectors. With continued reference to the "ibuprofen" example, system 2 may have an entry named "I-Prin," and the arrays related to that entry may include "ibuprofen," "Advil," "NeoProfen," "Caldolor," "Motrin IB," "isobutylphenylpropionic acid," "nonsteroidal," "anti-inflammatory," "treatment" "pain," "fever." Further, based on the similar terms in the arrays, the vector for the "I-Prin" can be similar to the vector for "ibuprofen." Based on the similarity, the verification system 402 can determine that "ibuprofen" in system 1 corresponds to "I-Prin" in system 2.

It will be understood that the various blocks described herein with respect to routine 700 can be performed in a different sequence, can be added, merged, or left out altogether, and that the routine 700 can implement one or more of the blocks concurrently and/or change the order, as desired. For example, rather than generating additional arrays (A2S1, A2S3), the verification system 402 can edit the array A1S1 or use some other data structure for storing and comparing the relevant information. Furthermore, in some cases, the messages, score, relevant portions, additional information, or the like can be stored in a data store for later retrieval.

It will be understood that fewer, more, or different blocks described herein with respect to routine 700 can be utilized to normalize events. For example, as mentioned above, in some cases, the verification system 402 can generate one or more vectors based on a similarity between an event parameter and an entry in the normalization database. Based on the vector value(s), the verification system 402 can identify an entry in the normalization database to which the event parameter corresponds (similar to matching entries in the arrays A1S1 that correspond to system 1 with entries in the arrays A1S2 that correspond to system 2 of block 718). Based on the match, the verification system 402 can replace the event parameter in the received event with the normalized event parameter or include a normalized event parameter corresponding to the event parameter from the received event in a normalized event. In some embodiments, the verification system 402 can determine a normalized event parameter for each event parameter of the received event until the event parameters are normalized, replaced with a normalized event parameter, or a complete normalized event is generated. It will be understood that in some cases, the event parameter of the received event may be the same as the normalized event parameter.

Moreover, in certain embodiments, once events from different systems are normalized, the verification system 402 can identify matches by comparing normalized event parameters of normalized events associated with different systems. In certain embodiments, the normalized events from different systems can be matched without the use of a cosine similarity or vector. For example, in certain cases, the normalized event parameters can be matched based on identical matches between the different normalized events. In this way, the normalized events can reduce the computing resources used to match disparate events between systems.

Mapping Information Between Systems

Figure 8:
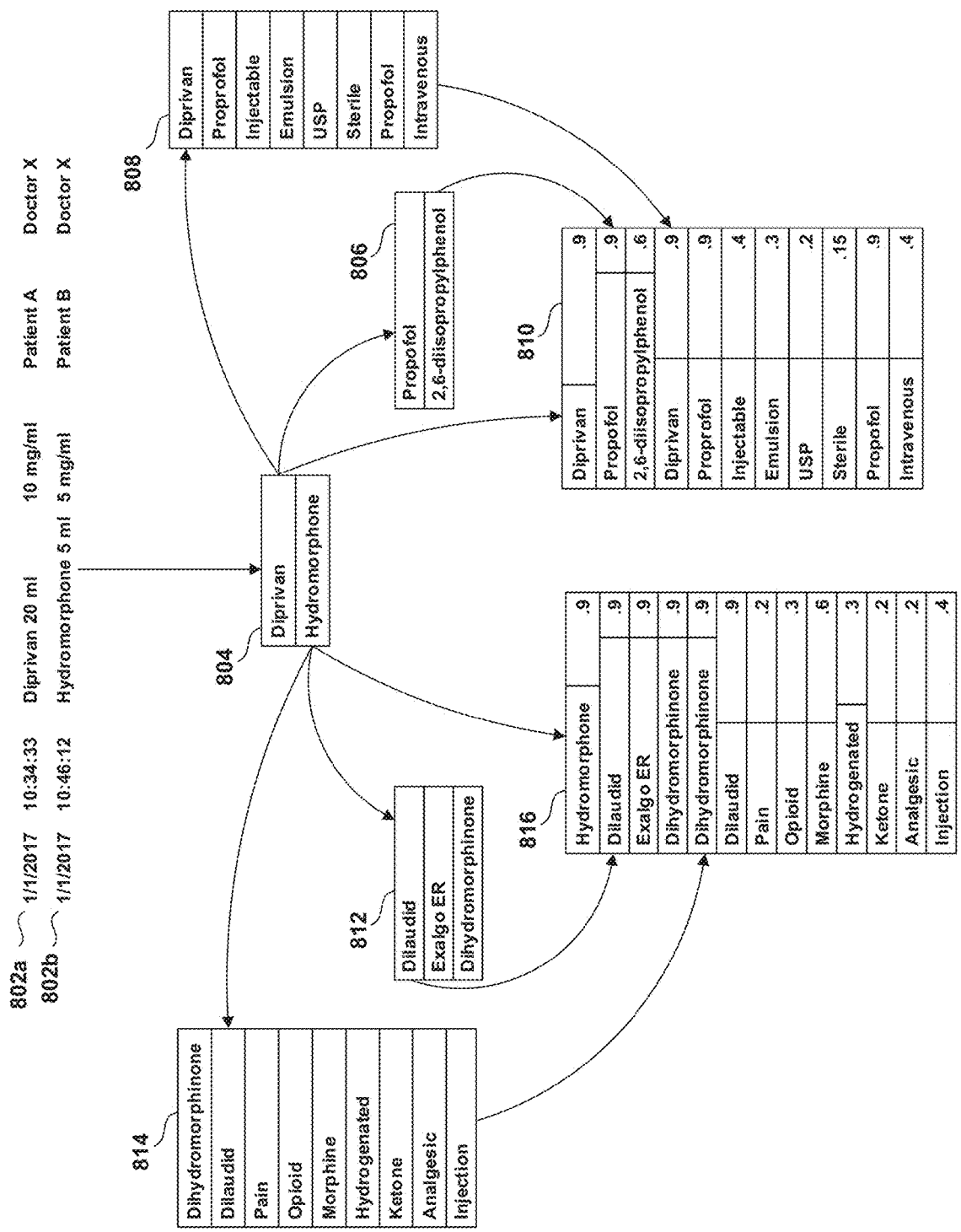
FIG. 8 is a block diagram illustrating an embodiment of different data structures that can be used to map relevant information between systems.

FIG. 8 is a block diagram illustrating an embodiment of different data structures that can be used to map relevant information between systems. With reference to FIG. 8, messages 802a and 802b can include various pieces of data related to an activity that involved Diprivan and Hydromorphone, respectively. From the messages 802a, 802b, the verification system 402 can generate the array 804 that includes the relevant field from each message, which in this case is the drug name.

Using the first entry of the array 804, the verification system 402 can generate the array 806 that includes alternate names or synonyms for Diprivan and the array 808 that includes additional information that is obtained about Diprivan from one or more sources. For example, the additional information can include other names for the drug (for example, generic or brand name(s), active ingredient, etc.), substitutes for the drug, medical descriptions of the drug (for example, description of drug in a dictionary encyclopedia, drug reference document, etc.). From the arrays 804, 806, 808, an additional array 810 can be generated that includes the first entry from array 804, the entries from each of the arrays 806, 808, and a score associated with one or more of the entries. The scores assigned to the entries can be used to compare Diprivan in system A with other drugs in other systems or the normalization database, as described in greater detail herein. For example, if another system refers to the same drug as Dipravan or Propofol, the verification system 402 can compare the scores or vectors from array 810 with a score or vector corresponding to Dipravan or Propofol from the other system to identify a match. Similarly, the verification system 402 can use the vectors or data to normalize the event parameter from system A.

Using the second entry of the array 804, the verification system 402 can generate the array 812 that includes alternate names or synonyms for Hydromorphone and the array 814 that includes additional information that is obtained about Hydromorphone from one or more sources. From the arrays 804, 812, 814, an additional array 816 can be generated that includes the second entry from the array 804, the entries from each of the arrays 812, 814, and a score associated with the entries. The scores assigned to the entries can be used to compare Hydromorphone in system A with other drugs in other systems or the normalization database, as described in greater detail herein.

Although illustrated for two messages, it will be understood that the verification system 402 can perform a similar array generation and comparison for more messages from one or more systems. Furthermore, in some cases, the verification system 402 can perform additional steps. For example, the verification system 402 can remove duplicates from the array 804 by comparing entries of the array 804 to determine if any matches exist. If a match exists, the verification system 402 can remove one or the entries of the array 804 corresponding to the match. In addition, although illustrated as various arrays 804, 806, 808, 810, 812, 814, 816, it will be understood that the verification system 402 can use fewer or more arrays for each entry. For example, all information can be included in a single array, arrays 806 and 812, arrays 808 and 814, and arrays 810 and 816 can be combined into their own arrays, respectively, or each of the arrays 806, 808, 810, 812, 814, 816 can each correspond to its own array. Furthermore, although described with respect to identifying related drugs, it will be understood that the verification system 402 can use the data structures described herein to identify other related information from different systems.

Discrepancies in Events Arrays

As described herein, medical service providers often use different systems located at various care sites to generate or monitor health care data. In some cases, one or more systems (such as the verification system 402) can be configured to associate events or other data from the different systems. The associated events can be utilized to efficiently group, relate, and/or evaluate health care data such that discrepancies or inconsistencies in the data can be identified and assessed, among other things. By associating events from the different systems, the verification system 402 can reduce the processing resources used to process or analyze health care data.

Figure 9:
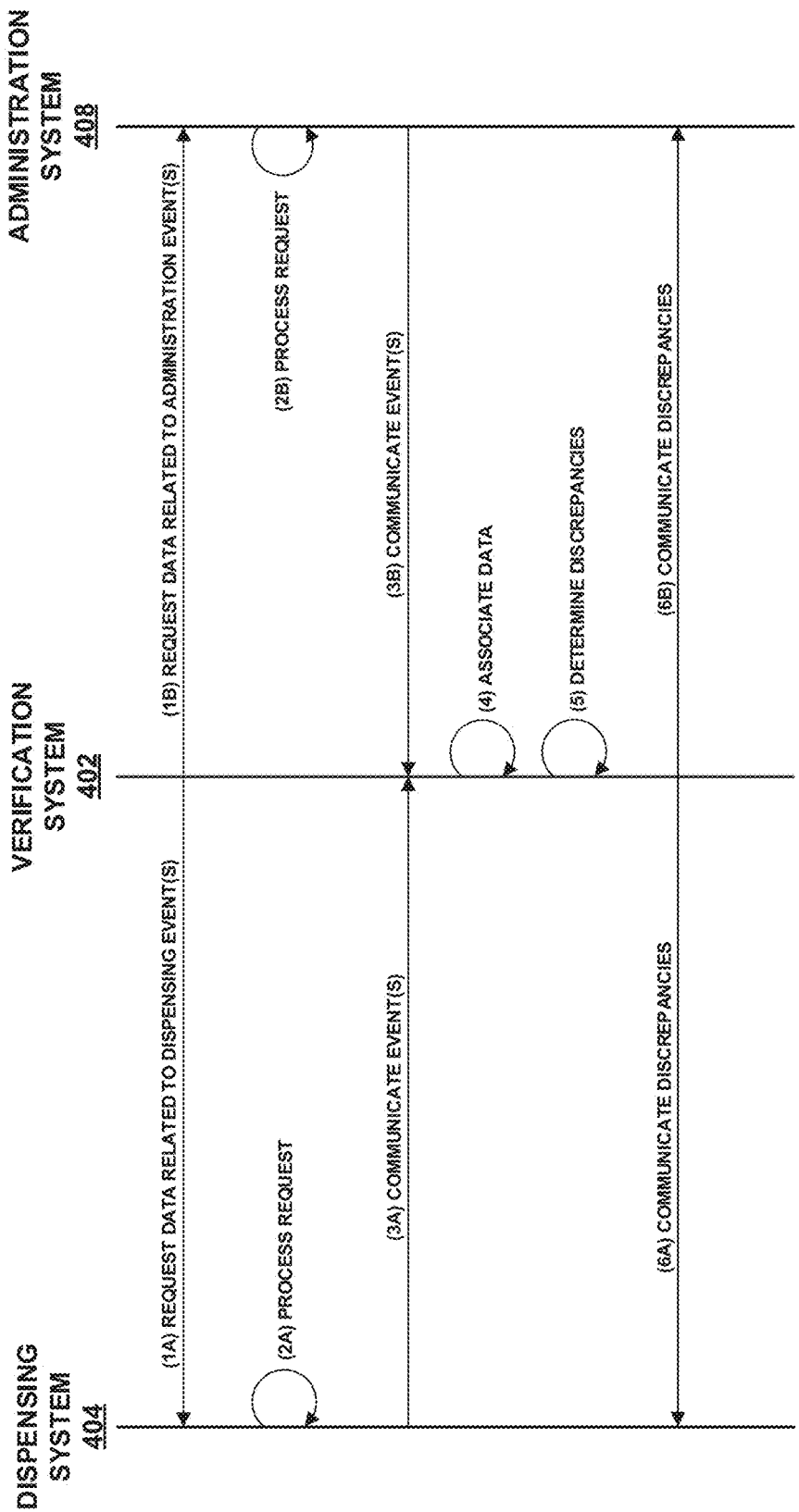
FIG. 9 is a data flow diagram illustrative of an embodiment of communications between different systems to identify discrepancies in events.

FIG. 9 is a data flow diagram illustrative of an embodiment of communications between different systems to identify discrepancies in events. One skilled in the relevant art will appreciate that the data flow outlined in FIG. 9 can be implemented using any one or any combination of the systems in the environment 400, such as the verification system 402, dispensing system 404, patient information system 406, administration system 408, or billing system 410. In this example, the data flow diagram includes communications between the verification system 402, the dispensing system 404, and the administration system 408. However, the following illustrative embodiment should not be construed as limiting.

At 1A, the verification system 402 requests data related to one or more dispensing events, which can include an instance in which the dispensing system 404 dispenses a drug or otherwise identifies that a drug was dispensed. As described herein, the data related to a dispensing event can include one or more dispensing event parameters, which can include, but are not limited to, one or more of a drug identifier, an action identifier, a timing identifier, a patient identifier, a provider identifier, a location identifier, or other information related to the dispensing event.

At 1A, the verification system 402 requests data related to one or more administration events, which can include an instance in which the administration system 408 administers a drug or otherwise identifies that a drug was administered. As described herein, the data related to an administration event can include one or more administration event parameters, which can include, but are not limited to, one or more of a drug identifier, an action identifier, a timing identifier, a patient identifier, a provider identifier, a location identifier, or other information related to the administration event.

It will be understood that the administration event data and/or dispensing event data can be collected using an RFID reading station (for example, RFID reading station 220) or via some other mechanism, such as a doctor or system user entering the information into the dispensing system 404 and/or administration system 408. Furthermore, dispensing events and administration events, as well as waste events and return events, can generally be referred to as events.

At 2A and 2B, the dispensing system 404 and the administration system 408 process the request. At 3A and 3B, the dispensing system 404 and/or the administration system 408 communicate the events to the verification system 402.

At 4, the verification system 402 associates the events. In some cases, the dispensing events and the administration events can be in different formats. Accordingly, as part of associating the data, the verification system 402 can format the events into a common or normalized format. For example, the verification system 402 can format each event from the different systems into an array and have an identifier assigned to each field in the array. In some cases, events received from the different systems can be referred to as pre-processed events and events that have been formatted or normalized can be referred to as processed events or normalized events. For example, the identifiers can correspond to the event parameters associated with each event, such as one or more of a drug identifier, an action identifier, a timing identifier, a patient identifier, a provider identifier or a location identifier.

As part of normalizing the data, the system can associate parameters of the pre-processed event to a normalized parameter. For example, a drug identifier in a pre-processed event may not match a normalized version of that event parameter. As such, when generating the normalized parameter, the system can use the normalized parameter in place of the corresponding parameter from the pre-processed event.

In some embodiments, the verification system 402 can generate a vector for the parameters of a pre-processed event. The verification system 402 can then use the vectors to identify a corresponding normalized parameter. In some embodiments, any one or any combination of the following can be used to generate a vector: brand name, generic name, concentration, package description, etc. Furthermore, in certain embodiments, the verification system 402 can normalize each event parameter of the pre-processed events. In some cases, the verification system 402 can concurrently generate normalized events. Accordingly, normalized events corresponding to events from different systems can be generated concurrently. For example, in some cases, the verification system 402 can utilize one or more processors to generate the normalized events in parallel, which can allow the system to efficiently identify discrepancies or potential abuse.

In some cases, to associate the data, the verification system 402 can compare the contents of the different arrays to identify related events. In some cases, two or more events (or normalized events) are related if the two or more events have certain matching event parameters. For example, in some cases, events are related if the events have matching patient, drug, and/or location identifiers. In addition or alternatively, in some cases, events that have timing identifiers that satisfy a timing threshold can be related. As a non-limiting example, a dispensing event can correspond to an instance in which morphine was dispensed at 12:00 PM, to be administered to Patient A, and an administration event can correspond to an instance in which morphine was administered at 12:14 PM to Patient A. In some cases, because the patient (Patient A) and drug (morphine) match, and because the time entries satisfy a timing threshold range of each other (for example, 1 hour), the events can be identified as related events. It will be understood, however, that events can be related in various ways, and the previous example should not be construed as limiting.

In some embodiments, the verification system 402 can generate a vector for each entry in an array. The verification system 402 can then compare the vectors to identify events that are related, or as mentioned, to normalize the events. In some embodiments, the verification system 402 can use any one or any combination of the following to generate the vector: brand name, generic name, concentration, and package description. In some cases, events that correspond to vectors that most closely match can be related to each other. In comparing contents of the different arrays or vectors, the verification system 402 can rely on a normalization database, matching table, or algorithm. For example, to identify related drugs, the verification system 402 can rely on a normalization database, such as the one described in greater detail above with reference to FIGS. 6-8.

Furthermore, as described above, the verification system 402 can compare time entries to identify related events. For example, the verification system 402 can identify events that have one or more matching event parameters and that are closest in time as related events. Alternatively, the verification system 402 can determine that events are not related if the difference in time between events does not satisfy a timing threshold. For example, successive events that would otherwise be related can be unrelated if they are more than a timing threshold (for example, more than ten minutes, thirty minutes, or one hour) apart from each other. As another example, two or more events that are otherwise related events may be unrelated if the first event (for example, the first in time) of the otherwise related events and the last event (for example, last in time) of otherwise related events are more than a timing threshold (for example, one or two hours) apart from each other. Further, in some cases, the verification system 402 can use sequence rules to identify related events. For example, the verification system 402 can determine that a dispensing event is not related to an administration event, a return event, or a waste event that precedes it. Additional rules and fuzzy logic can be used to identify related events.

From those related events, the verification system 402 can create or generate a plurality of event arrays. For example, each set of related events can be aggregated to form a different event array such that a single event array corresponds to a single set of related events. In some cases, each event array can include only those events that are related to each other (as described above). Further, in some cases, no events are included in more than one event array. As a non-limiting example, a particular event array can include events that have a matching patient identifier, drug identifier, and location identifier. In some cases, events having matching patient identifiers, drug identifiers, and location identifiers can be split into multiple event arrays based at least in part on their timing identifiers.

In some cases, the verification system 402 can concurrently generate the event arrays. Accordingly, discrepancies associated with one patient can be determined in parallel with discrepancies in another patient. For example, in some cases, the verification system 402 can utilize one or more processors to generate the event arrays in parallel, which can allow the system to efficiently identify discrepancies or potential abuse.

At 5, the verification system 402 reconciles events and determines discrepancies. For example, the verification system 402 can close out transactions that have complete documentation (e.g., those combinations of events that satisfy one or more rules applied thereto). To reconcile events and determine discrepancies, the verification system 402 can compare the data from the event arrays. If portions of the event array correspond to each other, then the verification system 402 can reconcile those portions. For example, for a particular event array, an entry may indicate that a 20 mL vial of Propofol was dispensed and another, later-in-time entry can indicate that a 20 mL of Propofol was administered to a patient. In some cases, the verification system 402 can reconcile those portions of data that resolve with each other (for example, where the amount dispensed equals the amount administered plus amount discarded).

If one or more of the events of an event array do not reconcile with other events of the event array (for example, an amount dispensed does not equal an amount administered plus an amount wasted/returned), then the verification system 402 can determine that those events are discrepancies. For example, for a particular event array, an entry may indicate that a 20 mL vial of Propofol was dispensed and a related entry from the administration system 408 can indicate that a 15 mL of Propofol was administered to a patient. Accordingly, the verification system 402 can determine that 5 mL of Propofol is missing. Because 5 mL of Propofol is unaccounted for, the verification system 402 does not close out those entries. Instead, the verification system 402 can determine that there is a discrepancy of 5 mL. However, if a subsequent entry is added to the event array that indicates that 5 mL of Propofol was discarded, then the verification system 402 can reconcile those entries. Comparing these entries and resolving any discrepancies can aid in preventing errors or abuse. Accordingly, by reconciling those entries in which the entire amount of the drug is accounted for. Further, by determining those instances in which a discrepancy exists, the verification system 402 can identify potential drug diverters, as described in more detail below. It will be understood that the verification system 402 can apply a variety of rules to the event arrays to determine discrepancies as described herein.

At 6A and 6B, the verification system 402 communicates discrepancies to the dispensing system 404 and/or the administration system 408. In some cases, when a discrepancy is identified, the verification system 402 can alert a user. For example, the communication to the different systems can include an indication that there is a discrepancy for a particular entry. Users of the different systems can use the indication to identify the person that was in possession of the drug corresponding to the discrepancy. In this way, the verification system 402 can help identify missing drugs and prevent waste, fraud, and abuse. In addition, the notification from the verification system 402 can cause the dispensing system 404 or the administration system 408 to correct a detected error, etc.

It will be understood that some of the data flow actions can occur in a different order or be omitted altogether. For example, the verification system 402 can request and/or receive the administration data and/or dispensing data at different times, or the administration system 408 and dispensing system 404 can automatically report the relevant data without a specific request from the verification system 402, or a user may upload the data from the administration system 408 and dispensing system 404 to the verification system 402. Further, multiple data requests to one system may correspond to a single request of another system. For example, the verification system 402 may make multiple requests for data from the administration system 408 to match up with data from the dispensing system 404 received after one request.

Further, fewer, more or different actions can be taken by the verification system 402. For example, the verification system 402 can display the discrepancies to a user. In addition, although illustrated as requesting/receiving information from two systems, it will be understood that the verification system 402 can interact with any number of systems that include event data. For example, the verification system 402 can receive relevant information about a pharmacy item, patient, or activity from medical devices, waste systems, billing systems, scheduling systems, or from multiple administration systems 408 or dispensing systems 404, or inventory systems. In such embodiments, the verification system 402 can process the data from the various systems to identify matching events from the different systems and track the location, use, and billing of the pharmacy items over time.

In some cases, any of steps 1-4 can occur automatically, without user interaction. For example, in some cases, the event arrays are generated automatically and stored as data structures. Furthermore, any of steps 5 or 6 can occur automatically or can be performed in response to or based on a user's request. For example, a user can request information, and in real-time, the system can parse all the relevant data in a time window to identify and report discrepancies.

Obfuscating Personal Health Information

As mentioned herein, it can be difficult to communicate meaningful information about events (for example, the dispensing of medication, the administration of medication, etc.) without communicating personal health information (PHI). However, the communication of PHI is heavily regulated.

Figure 10:
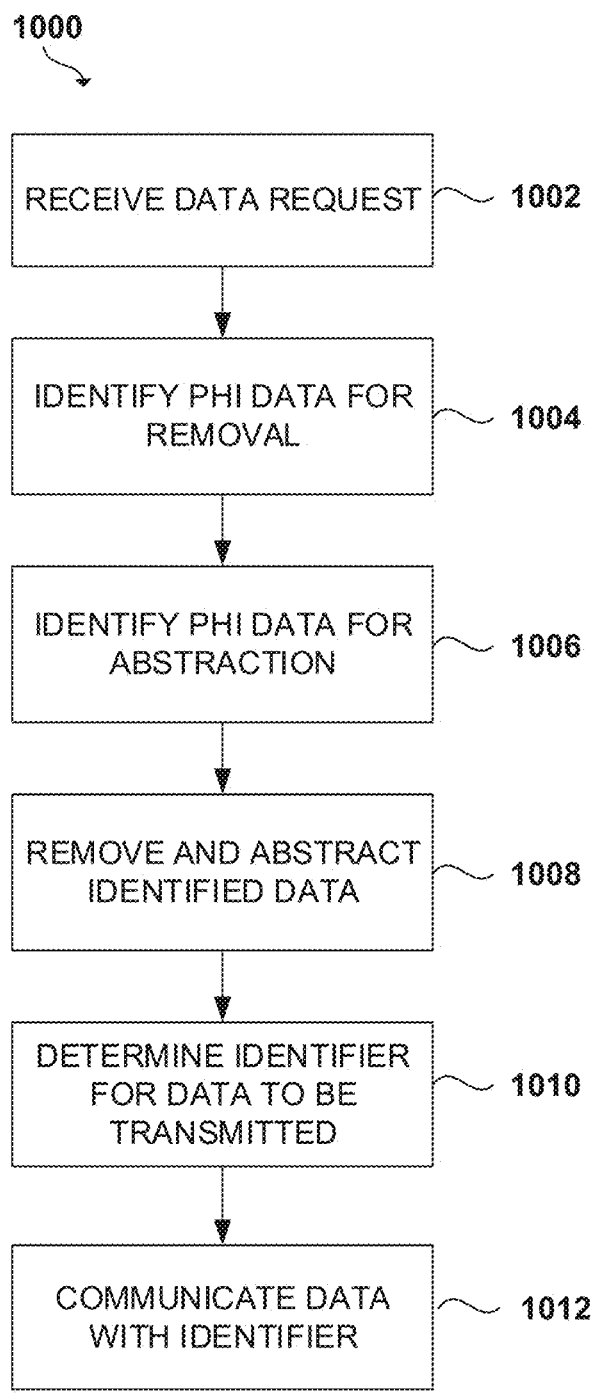
FIG. 10 is a flow diagram illustrative of an embodiment of a routine to communicate event data information between systems with personal health information (PHI) obfuscated.

FIG. 10 is a flow diagram illustrative of an embodiment of a routine 1000 to communicate event data information between systems with the PHI obfuscated. One skilled in the relevant art will appreciate that the elements outlined for routine 1000 can be implemented using any one or any combination of the systems in the environment 400, such as the verification system 402, dispensing system 404, patient information system 406, administration system 408, or billing system 410. For simplicity, the routine 1000 has been logically associated as being implemented by a system.

However, the following illustrative embodiment should not be construed as limiting. Furthermore, it will be understood that the various blocks described herein with reference to FIG. 10 can be implemented in a variety of orders. For example, some blocks can be implemented concurrently or the order can be changed, as desired. Furthermore, it will be understood that fewer, more, or different blocks can be used as part of the routine 1000. For example, in some embodiments, one or more of blocks 1002-1012 are not implemented. However, it will be understood that any of the blocks (and more or different blocks) can be implemented as part of routine 1000.

At block 1002, the system receives a request for data that includes PHI. For example, the request for data can be similar to the request received by the dispensing system 404 at 1A of the flow diagram of FIG. 9 or the request received by the administration system 408 at 1B of the flow diagram of FIG. 9.

At block 1004, the system identifies PHI data for removal. In some cases, the system can identify PHI data that may not be used or required to respond to the request. For example, the system can identify that the patient's name, social security number, gender, or the like is not required.

At block 1006, the system identifies PHI data for abstraction. For example, in some cases, some of the PHI data can be able to be abstracted to a range or otherwise adjusted or changed. For example, the system can identify numbers that can be converted into a range, such as a weight (for example, 175 lbs.) to a weight range (range, 160-180 lbs.). As another example, the system can identify other information, such as time, that can be adjusted by a set amount. For example, if a medication was administered at 12:05 PM, it can be adjusted to 5:45 AM. In some cases, all systems that obfuscate PHI can adjust related information (for example, the time) by the same amount to ensure consistency of the obfuscation.

At block 1008, the system removes the PHI data identified for removal and abstracts or changes the PHI data identified for abstraction. In some cases, when multiple systems are communicating PHI data, each of the systems can be configured to remove and abstract the PHI data in the same way for consistency purposes. Alternatively, in some cases, one or more of the systems can abstract the PHI data in a different way, and a centralized or receiving system (for example, the verification system 402) can be configured to associate the data from the different systems despite the different abstraction techniques.

In some cases, some of the data is neither removed nor abstracted. For example, the system can leave intact a user name (e.g., person performing the action, such as the nurse or doctor), user identifier, user role (doctor, nurse, etc.), medication name, concentration identifiers, count (number of packages used), amount, transaction type (e.g., dispense, waste, return, administration, etc.) location, time, patient name, patient identifier, etc.

At block 1010, the system determines an obfuscated identifier for the data to be transmitted. In some embodiments, the obfuscated identifier can be randomly assigned. In certain embodiments, the obfuscated identifier can be determined based on the PHI data to be transmitted, such as a hash of the PHI data, or based on an identifier in the PHI data, such as the name of the patient or patient ID.

In some cases, when different systems are determining the obfuscated identifier, they can determine the obfuscated identifier in the same way such that when the system that receives the data from other systems, it can match the data. For example, a patient information system 406 and dispensing system 404 that have the same patient ID can transform or obfuscate the patient ID in the same way such that the obfuscated identifier received by a verification system 402 from both the patient information system 406 and dispensing system 404 are the same. In this way, the verification system 402 can more easily match the data but remains unable to identify to whom the data corresponds.

In some cases, when different systems are determining the obfuscated identifier, each system determines the obfuscated identifier in a different way. As a result, it can be difficult for the system to match the data between the different systems. Thus, in some cases, the systems can also communicate an indication of how the data was obfuscated. For example, a patient information system 406 and dispensing system 404 that have the same patient ID can transform or obfuscate the patient ID in a different way, but can each communicate an indication of how the data was obfuscated. In some cases, the communication of the indication of how the data was obfuscated can be encrypted or otherwise secure. In this way, the verification system 402 can determine how each system obfuscated the data was obfuscated, but, in some cases, the data remains unable to identify to whom the data corresponds.

At block 1012, the system communicates the data with the obfuscated identifier. In this way, the receiving system can perform various analytics or processing on the data without the PHI. In some cases, when the receiving system completes the processing it can return its information along with the obfuscated identifier. In this way, the system can identify to which record the data from the other system corresponds and can update any records as desired.

It will be understood that the various blocks described herein with respect to routine 1000 can be performed in a different sequence, can be added, merged, or left out altogether, and that the routine 1000 can implement one or more of the blocks concurrently and/or change the order, as desired. Furthermore, it will be understood that fewer, more, or different blocks can be used as part of the routine 1000 to communicate event data information between systems with the PHI obfuscated. For example, in some embodiments, the system can perform block 1004 without or before receiving a data request. Furthermore, in some embodiments, the system can encrypt the data along with the obfuscated identifier to further reduce the likelihood of the PHI data being discovered.

Event Arrays

Figure 11:
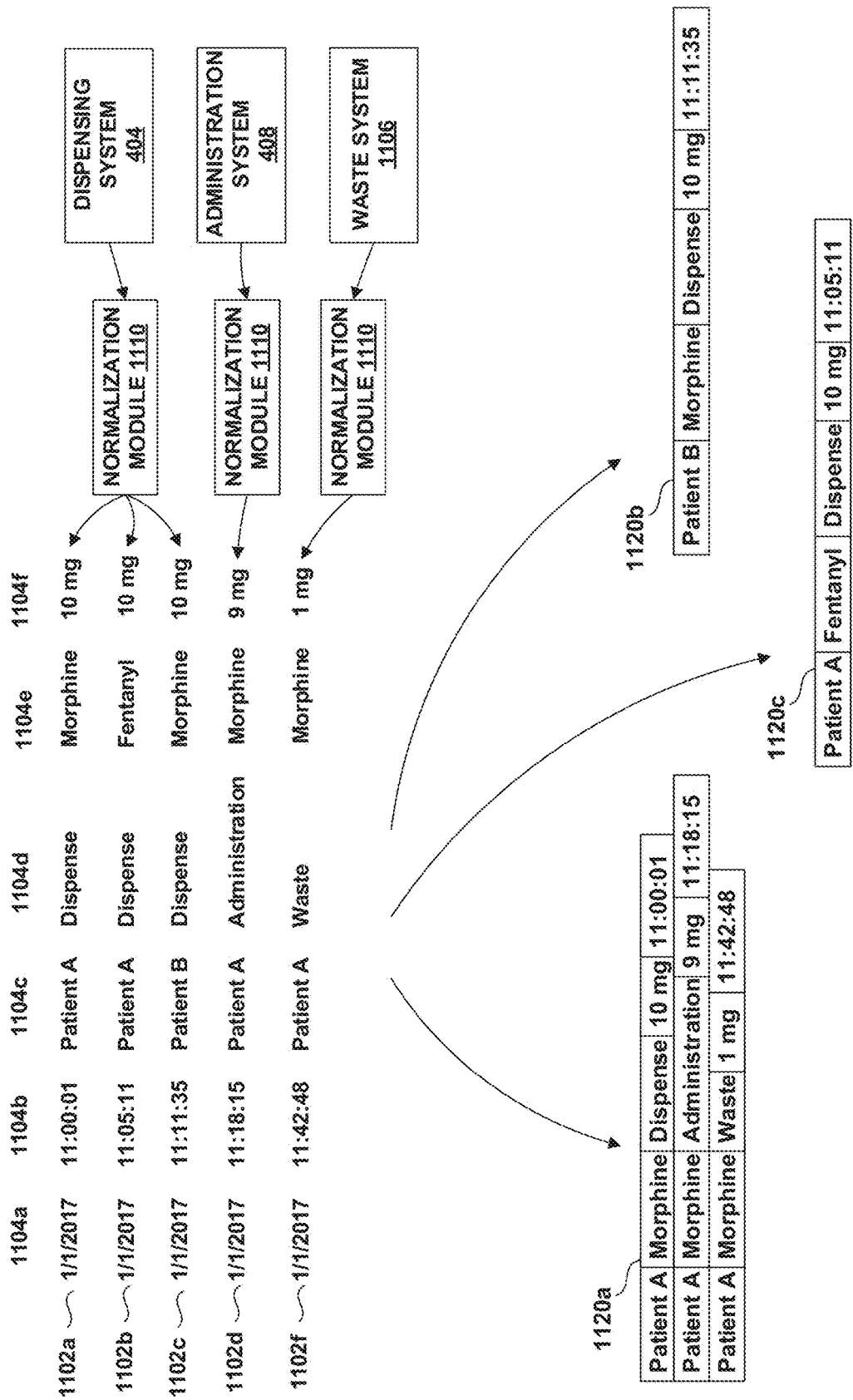
FIG. 11 is a block diagram illustrating an embodiment of generation of example events arrays.

FIG. 11 is a block diagram illustrating an embodiment of generation of example events arrays. With reference to FIG. 11, the events 1102a, 1102b, 1102c, 1102d, and 1102f can be normalized events and can each include a plurality of event parameters including, but not limited to, a first timing identifier 1104a, a second timing identifier 1104b, a patient identifier 1104c, an action identifier 1104d, a first drug identifier 1104e, and a second drug identifier 1104f. From the events 1102a, 1102b, 1102c, 1102d, and 1102f, the verification system 402 can generate the event arrays 1120a, 1120b, and 1120c.

As described herein, the verification system 402 can receive events from a plurality of systems. In the illustrated embodiment, the plurality of systems includes a dispensing system 404, an administration system 408, and a waste system 1106. However, the verification system 402 can receive events from fewer or more systems, as described herein.

Furthermore, as described herein, in some cases, the events received from the different systems 404, 408, and 1106 are not compatible with each other. For example, the events from one system can be in a different format than another system. Accordingly, in some cases, the verification system 402 can normalize the events to format the events such that they are in the same or a common format. For example, as illustrated, the verification system 402 can include a normalization module 1110 that transforms the pre-processed events to processed or normalized events. As described herein, the verification system 402 can use a variety of techniques to normalize the events, including matching data from one system to normalized data or data from a normalization database, generating vectors of event parameters, and/or using cosine similarity to identify a normalized parameter to which the event parameter corresponds.

In some cases, the verification system 402 can store the normalized events in a data store. For example, in some cases, as described herein, the verification system 402 will wait a predetermined period of time before generating the event arrays from the stored events. As such, the verification system 402 can aggregate and store the events until the verification system 402 is ready to process them to generate the event arrays.

Using one or more of the event parameters 1104a-1104f, the verification system 402 can identify which, if any, of the events 1102a, 1102b, 1102c, 1102d, and 1102f are related. For example, as described herein, the verification system 402 can identify that events are related based on a determination that the events include matching patient identifiers 1104c, matching drug identifiers 1104e, and/or satisfy a timing threshold. With reference to the illustrated example of FIG. 11, the verification system 402 can determine that events 1102a, 1102d, and 1102f are related. In addition, the verification system 402 can determine that events 1102b and 1102c are each unrelated to any other events.

Using the events and/or the event parameters, the verification system 402 generates the event arrays 1120a, 1120b, and 1120c based at least in part on the identified related events. For example, as illustrated, event array 1120a include related events 1102a, 1102d, and 1102f. In some cases, the event arrays 1120a, 1120b, and 1120c can be generated via a two-step process. For example, as part of a first step in the generation of an event array, the verification system 402 can identify a set of normalized events that includes at least one matching event parameter and/or can generate a first event array that includes the identified set of normalized events. For example, in some cases, a first event array is generated that includes events with matching patient identifiers 1104c and drug identifiers 1104e. As part of a second step in the generation of an event array, the verification system 402 can generate a second event array from the first event array. For example, to generate the second event array, the verification system 402 can identify, from the set of normalized events of the first array, those events that occurred within a particular window of time from the one or more of the events of the set of normalized events. For example, one or more second event arrays can be generated from the first event array, where each second event array includes events that satisfy a timing threshold and that include matching patient identifiers 1104c and drug identifiers 1104e. With reference to the illustrated embodiment, the event arrays 1120a, 1120b, and 1120c can correspond to second event arrays that satisfy a timing threshold and include matching patient identifiers 1104c and drug identifiers 1104e. Although described as a two-step process to generate an event array, it will be understood that more or fewer steps can be utilized. For example, the steps can be combined into a signal step. For example, the verification system 402 can generate an event array by identifying a set of normalized events that include at least one matching parameter and are within a particular window of time. Furthermore, in some cases, the process for generating an event array can be different.

Although illustrated for five events, it will be understood that the verification system 402 can perform a similar event aggregation and event array generation for more events from one or more systems. For example, the verification system 402 can concurrently generate normalized events and perform a similar event aggregation and/or event array generation on thousands or millions of events. In some cases, by generating normalized events and then aggregating normalized events into event arrays, the system can significantly reduce the processing time to generate event arrays. Furthermore, in some cases, the verification system 402 can perform additional steps. For example, the verification system 402 can remove duplicates from the events 1102a-1102 by comparing event parameters of the events to determine if any matches exist. If a match exists, the verification system 402 can remove one or the events corresponding to the match. In addition, although illustrated as various event parameters 1104a-114f are shown, it will be understood that the events can include fewer or more event parameters.

Furthermore, with respect to generation of the event arrays 1120a-1120c, it will be understood that these event arrays can be generated concurrently by the verification system 402. In some cases, as described herein, the verification system 402 can wait a predetermined period of time before generating the event arrays 1120a-1120c using the events (or normalized events) in the data store. For example, as illustrated, while event array 1120a may satisfy one or more rules (e.g., dispense amount equals administration and waste amounts), event arrays 1120b and 1120c may not. That is, in the illustrated example, event arrays 1120b and 1120c each include a dispense event, but there is no corresponding administration, waste, or return event. In some cases, to increase the likelihood that the verification system 402 has received all of the related events for an event array, the verification system 402 can wait a predetermined period of time after a time stamp associated with an event to generate an event array.

For example, event 1102f has a timing identifier 1104b of 11:42:48. Accordingly, in some cases, the system can wait a predetermined period of time (for example, 1 hour) before generating the event array 1120a. In some cases, the verification system 402 can query the systems at or around 12:42:48 to increase the likelihood that is has received the relevant events.

In some cases, the predetermined period of time over which the system waits to generate the summary can correspond to a timing identifier of one or more events that are determined to be related events. For example, as described above, events 1102a, 1102d, and 1102f are related events. In some cases, the system can wait a predetermined period of time after the time stamp of the first event of the related events (in this case, event 1102a) before generating the event array for that event. In some cases, the system can wait a predetermined period of time after the time stamp of the last event of the related events (in this case, event 11020 before generating the event array that includes for that event.

It will be understood that although the verification system 402 can concurrently generate the event arrays, as described above, in some cases, the generation of one or more event arrays can be paused or put on hold until the system waits the predetermined period of time corresponding to that event or group of related events. Thus, although the system waits to generate an event array for some events, it can proceed to generate event arrays for other events that satisfy the timing threshold has been satisfied.

Event Tracking and Diversion Detection

Pharmacies, hospitals, and other medical facilities are continuously confronting the increasing challenge of theft of controlled substances, also referred to as drug diversion. Drug diversion can occur anywhere in the distribution, administration, and documentation chain. While medical facilities are under pressure to account for and control losses, those who divert or steal drugs (generally referred to as diverters) can be difficult to detect. Accordingly, medical facilities need better tools to identify and prevent drug diversion, while remaining compliant with privacy related regulations.

As described herein, a system, such as verification system 402, can associate data between various systems (including but not limited to the dispensing system 404, the patient information system 406, the administration system 408, or the billing system 410), reconcile events, and identify discrepancies between events. By reconciling or closing out transactions that have complete documentation of the drug, and identifying discrepancies, the system can focus on specific events (for example, those associated with the discrepancies) to help to minimize risk of future diversions.

Figure 12:
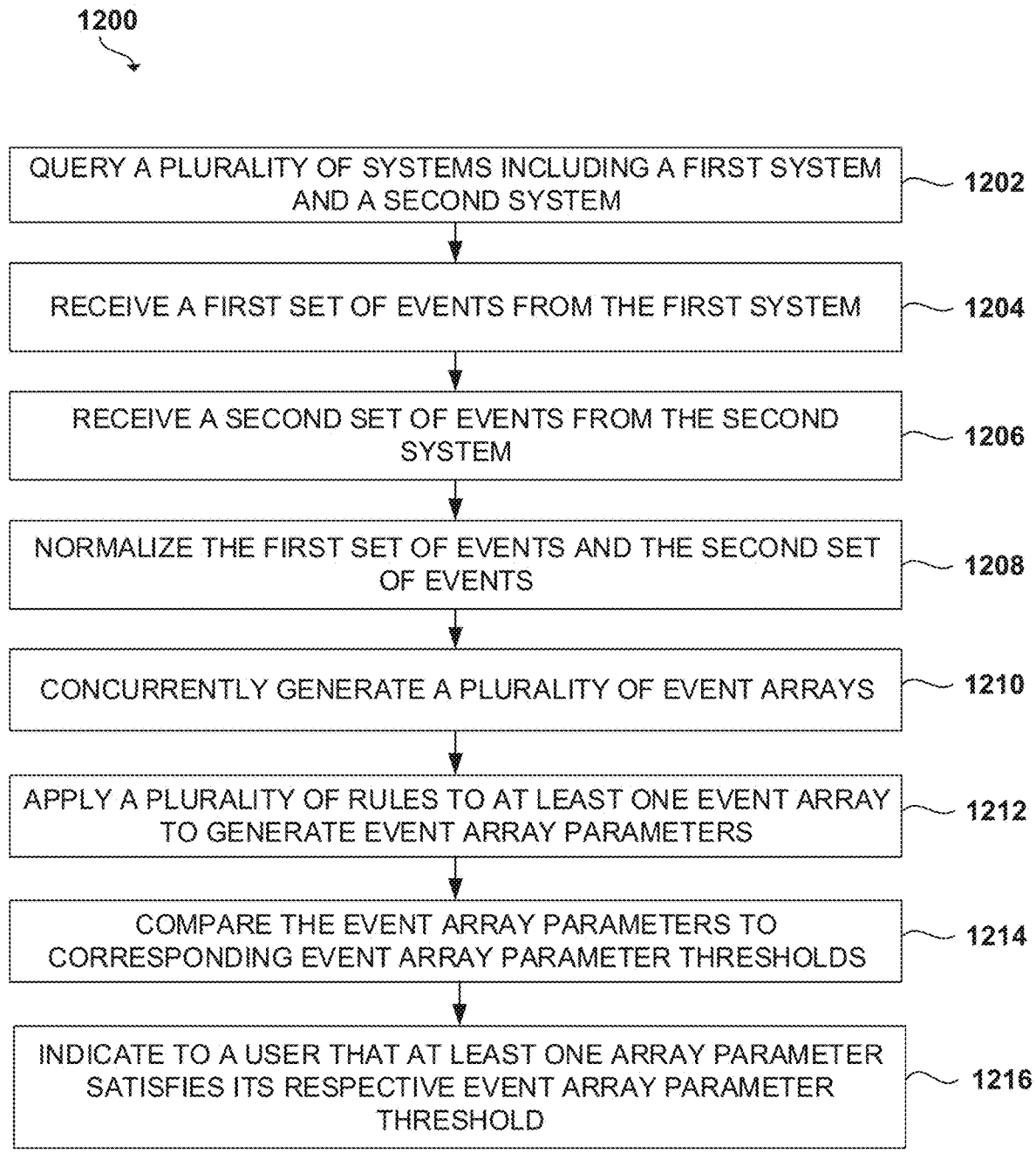
FIG. 12 is a flow diagram illustrative of an embodiment of a routine to determine event discrepancies between disparate systems.

FIG. 12 is a flow diagram illustrative of an embodiment of a routine 1200 to determine event discrepancies between disparate systems. One skilled in the relevant art will appreciate that the elements outlined for routine 1200 can be implemented using any one or any combination of the systems in the environment 400, such as the verification system 402, dispensing system 404, patient information system 406, administration system 408, or billing system 410. For simplicity, the routine 1000 has been logically associated as being implemented by the verification system 402. However, the following illustrative embodiment should not be construed as limiting. Furthermore, it will be understood that the various blocks described herein with reference to FIG. 12 can be implemented in a variety of orders. For example, some blocks can be implemented concurrently or the order can be changed, as desired. Furthermore, it will be understood that fewer, more, or different blocks can be used as part of the routine 1200. For example, in some embodiments, one or more of blocks 1202-1216 are not implemented. However, it will be understood that any of the blocks (and more or different blocks) can be implemented as part of routine 1200.

At block 1202, the verification system 402 queries a plurality of systems for data related to one or more events. The plurality of systems can include at least a first system and a second system, and one or both of the first system or the second system can include one or more of the dispensing system 404, the patient information system 406, the administration system 408, or billing system 410, as described herein.

To query the systems, the verification system 402 can transmit one or more requests for the data via a network, such as network 412 of FIG. 4. For example, the verification system 402 can send a request that requests a system to update the verification system 402 with the particular system's data that is related to one or more events. In addition or alternatively, the request can include a request for data related to one or more events that occurred within a particular time window, such as within the past hour, day, or week, or with in a particular time or date range.

In some cases, the verification system 402 can query the systems based at least in part on a user command. For example, a user can submit a request for the data (non-limiting examples: by opening a web browser or application, by interacting with a graphical user interface), and responsive to the request by user, the verification system 402 can query the systems. In addition or alternatively, the verification system 402 can query the plurality of systems automatically, such as at one or more time intervals. For example, the verification system 402 can query the systems one or more times a second or every few seconds. In addition or alternatively, the verification system 402 can query the systems hourly, daily, weekly, monthly, or the like. In some cases, the interval at which the verification system 402 queries the systems can be configurable by a user. Moreover, in some cases, the verification system 402 can query one or more of the systems at different times or simultaneously. Furthermore, as described in more detail below, in some cases, one or more systems can provide data to the verification system 402 without receiving a request from the verification system 402. For example, the one or more systems can be configured to send the data to the verification system 402 at one or more time intervals, and the verification system 402 can passively receive the data.

At block 1204, the verification system 402 receives a first set of events from the first system. The first set of events can include data related to one or more events including, but not limited to, a dispensing event, an administration event, a waste event, or a return event. For example, each event of the first set of events can include a plurality of event parameters. The event parameters include a combination of one or more of an action identifier (non-limiting examples: identifying the event as a dispensing event, an administration event, a waste event, or a return event), drug data (drug name, drug quantity, drug concentration, package size, or other drug identifying information), a patient identifier, a time identifier, a care area identifier, a provider identifier (for example, name of the caregiver, nurse, or doctor performing the event), a witness identifier (non-limiting example: a name of a witness of the event), or the like.

At block 1206, the verification system 402 receives a second set of events from a second system. As described above with respect to the first set of events, the second set of events can include data related to one or more events including, but not limited to, a dispensing event, an administration event, a waste event, or a return event. Furthermore, each event of the second set of events can include a plurality of event parameters, as described above with respect to block 1204.

In some cases, the second set of events received at block 1206 are different from and are not compatible with the first set of events received at block 1204. For example, although the events of the first and second sets of events can each include event parameters, the first and second sets of events, or the event parameters, can be different from and/or incompatible with each other. For example, the first and second sets of events can be stored in or provided by the systems as different file types or different versions of a similar file type. In some cases, the first and second sets of events can be stored in the same or a similar file type, yet the event parameters associated with each of the sets of events are different and/or are stored or sorted in a different order.

Although the routine 1200 includes the verification system 402 receiving sets of events from the first and second systems, the verification system 402 can additionally or alternatively receive sets of events from other systems.

At block 1208, the verification system 402 normalizes the first set of events and the second set of events. For example, to normalize the first set of events and the second set of events (and any other sets of events), the verification system 402 can convert the sets of events into processed events or normalized events as described herein.

In some cases, as part of the normalization of the first set of events and the second set of events, the verification system 402 can aggregate the events such that some or all of the normalized events of the first set of events and the second set of events are collected or combined into an array. Moreover, as described herein, in some cases, the verification system 402 can remove duplicate events from the aggregated events.

At block 1210, the verification system 402 concurrently generates a plurality of event arrays. For example, in some cases, the verification system 402 can utilize a plurality of processors to generate the event arrays in parallel. As described herein, the verification system 402 can compare the contents of the different events to identify and/or group related events. As a non-limiting example, in certain cases, the verification system 402 can determine that events are related if the events are associated with the same patient identifier, drug identifier, location identifier, and/or satisfy a timing threshold. Each set of related events can be aggregated to form an event array (first or second event array as described herein), such that a single event array corresponds to a single set of related events. In some cases, each event array can include (only) those events that are related to each other (as described above). Further, in some cases, no events are included in more than one event array. However, in certain cases, events can be included in multiple arrays. For example, an event can be included in a first event array based on its patient identifier and drug identifier and can be included in a second event array based on its patient identifier, drug identifier, and timing identifier.

At block 1212, the verification system 402 can apply at least one rule to the event array to generate one or more event array parameters. For example, the rule can include one or more instructions that specifies or indicates how to generate an event array parameter from the event array. In general, a rule can include an instruction for extracting a value (e.g., an event array parameter) from or determining a value associated with the at least one event array. In some cases, the applied rule can include one or one of a sequence rule, dispensing rule, omission rule, timing rule, drug quantity rule, location rule, witness rule, or behavior rule, described in more detail below, or other rule as the case may be.

At block 1214, the verification system 402 compares the event array parameter to one or more corresponding event array parameter thresholds. As described in more detail below, an event array parameter threshold can come in many forms, and can be based at least in part on the applied.

In some cases, the event array parameter threshold can correspond to a binary output, such as yes or no, true or false, 1 or 0, high or low, etc. As a non-limiting example, the event array parameter threshold can be "yes." Accordingly, in some embodiments, if the event array parameter corresponds to "yes," then the system can determine that the event array parameter satisfies the event array parameter threshold, and if the event array parameter is "no," then the system can determine that the event array parameter does not satisfy the event array parameter threshold, or vice versa.

In some cases, the event array parameter threshold can correspond to a string or list. In cases such as these, if the event array parameter includes a string or list that matches (or substantially matches) the string or list of the event array parameter threshold, then the system can determine that the event array parameter satisfies the event array parameter threshold. In contrast, if the event array parameter does not include a string or list that matches the string or list of the event array parameter threshold, then the system can determine that the event array parameter does not satisfy the event array parameter threshold.

As another example, the event array parameter threshold can correspond to a value. As a non-limiting example, the event array parameter threshold can be 30. Accordingly, in some cases, if the event array parameter is greater than or equal to 30, then the system can determine that the event array parameter satisfies the event array parameter threshold. Alternatively, in some cases, if the event array parameter is less than or equal to then the system can determine that the event array parameter satisfies the event array parameter threshold.

The verification system 402 can determine event array parameter thresholds using a variety of techniques. For example, in some cases, the verification system 402 can determine the event array parameter thresholds based at least in part on a set of event arrays. The set of event arrays can be selected based on a window of time, similarity between event parameters (e.g., position or user ID, etc.) Accordingly, what is considered normal (for example, satisfies a threshold) from one set of event arrays can be abnormal (or fails to satisfy a threshold) in another.

In some cases, the verification system 402 can determine an average (non-limiting examples: average time between events of the event arrays, average or most common sequence of events in the event arrays, common events in event arrays, etc.) for the set of event arrays and determine the event array parameter threshold based on a deviation from the average (non-limiting example: standard deviation, difference, etc.

At block 1216, the verification system 402 can cause an indication to the user that at least one event array parameter satisfies its respective event array parameter threshold and/ or an indication that at least one array parameter does not satisfy its respective event array parameter threshold. For example, as described herein at least with respect to FIG. 13, in some cases, the system can display a graphical user interface that displays the indication.

It will be understood that the various blocks described herein with respect to routine 1200 can be performed in a different sequence, can be added, merged, or left out altogether, and that the routine 1200 can implement one or more of the blocks concurrently and/or change the order, as desired. Furthermore, it will be understood that fewer, more, or different blocks can be used as part of the routine 1200 to determine event discrepancies between disparate systems.

For example, the verification system 402 can receive the first set of events and/or the second set of events without querying systems for the data. For example, in some cases, one or more systems can be configured to transmit the events to the verification system 402 at predetermined intervals. Furthermore, in some embodiments, the verification system 402 can sort the plurality of normalized events based on one or more of the events parameters associated with an event. For example, the verification system 402 can sort the plurality of normalized events based on the timing identifier. Furthermore, as described in more detail below, in some embodiments, the verification system 402 can generate and/or display a score based on the comparison of the event array parameter and the event array parameter thresholds.

Rules and Event Array Parameters

As described herein, the verification system 402 can apply one or more rules to the event arrays. Based on the rules applied to the event arrays, the verification system 402 can generate one or more event array parameters. The event array parameters can be compared with event array parameter thresholds. Based on the comparison, the verification system 402 can indicate a potential misuse or abnormality.

In some cases, the verification system 402 can generate the event array parameter for each event array. For example, the verification system 402 can generate one event array parameter for each event array by applying a sequence rule and another event array parameter for each event array by applying an omission rule.

In certain cases, the verification system 402 generates an event array parameter for a combination of event arrays, such as a group of event arrays associated with the same user. For example, the verification system 402 can generate an event array parameter for a group of event arrays associated with a particular user by applying a timing rule to the event arrays associated with the user. As a specific example, the verification system 402 can generate an average time between events of event arrays associated with the user.

Event Array Parameter Thresholds

For each rule applied to one or more event arrays, the verification system 402 can determine or use an event array parameter threshold. The event array parameter thresholds can be static or dynamically determined by the verification system 402. For example, in some cases, the difference between an amount dispensed and the combination of the amount administered, wasted, and returned is to be zero. Thus, in certain circumstances, the verification system 402 can use zero as the event array parameter threshold when analyzing event arrays using a dispensing rule.

In cases where the event array parameter threshold is dynamic, the verification system 402 can determine the event array parameter threshold using a variety of techniques. For example, in some cases, the verification system 402 can determine an event array parameter threshold based at least in part on a set of event arrays. The set of event arrays can be selected based on a window of time, similarity between event parameters (e.g., position or user ID, etc.), etc. Thus, the event array parameter thresholds can vary from one set of event arrays to another.

In some cases, the verification system 402 can determine an average (non-limiting examples: average time between events of the event arrays, average or most common sequence of events in the event arrays, common events in event arrays, average number of event arrays for users with a discrepancy or that do not satisfy an event array parameter threshold associated with an omission or dispensing rule, etc.) for the set of event arrays and determine the event array parameter threshold based on a deviation from the average (non-limiting example: standard deviation, difference, etc.

Rule Thresholds

As described herein, the system can apply one or more rules to an individual event array to determine whether the event array satisfies an event array parameter threshold. Similarly, in some embodiments, the verification system 402 can use multiple event arrays to determine whether a user satisfies a rule threshold. In some cases, the satisfaction of an event array threshold by a single event array can indicate misuse. In certain cases, it is multiple event arrays satisfying multiple event array thresholds that indicate misuse. Accordingly, the verification system 402 can aggregate event arrays associated with a user to determine the likelihood of misuse. In certain cases, the verification system 402 can use a rule threshold to determine the likelihood of misuse.

In some cases, the rule threshold can be based on a set of data. For example, the verification system 402 can analyze a set of data to determine an average number of event arrays that satisfy different event array parameter thresholds. Based on the determined average, the verification system 402 can determine the rule threshold. For example, the rule threshold can be determined by identifying a deviation from the average, such as a difference from the average or a standard deviation from the average.

The system can determine a threshold for each of the rules applied to the event arrays. For example, the system can determine a sequence rule threshold, a dispensing rule threshold, omission rule threshold, timing rule threshold, drug quantity rule threshold, location rule threshold, witness rule threshold, or behavior rule threshold. Based on the rule thresholds, the verification system 402 can identify one or more abnormalities associated with a particular user.

Sequence Rules

In some cases, one or more sequence rules can be applied to some or all event arrays to generate one or more event array sequence parameters. A sequence rule can include instructions to identify various event sequences corresponding to the event array(s). The application of the sequence rule (for example, the result of performing the instructions) can result in an event array sequence parameter.

In general, each event array, regardless of the number of events within the event array, can be associated with an overall sequence. As a non-limiting example, an event array can include three events, and, from earliest in time to latest in time, the events can include a dispensing event, administration event, and a waste event. Here, the overall sequence of the event array can include a list, a string, or other indication of the order of the events: that is, dispense-administration-waste. Accordingly, in cases in which the sequence rule includes instructions to identify the overall sequence of events, the event array sequence parameter can include a list, a string, or other indication of the order of the events.

In many instances, in addition to the overall sequence, multiple other sequence identifiers can be extracted from a particular event array. For example, a sequence rule can include instructions to identify a first event in the sequence of events. Accordingly, in this case, the resulting event array sequence parameter can include an indication of a dispense event. Similarly, a sequence rule can include instructions to identify a last event in the event array. Accordingly, in this case, the resulting event array parameter can include an indication of a waste event.

In addition or alternatively, a sequence rule can include instructions to identify whether a particular type of event follows or precedes another particular type of event. In instances such as these, the event array sequence parameter can be a selection of a binary response (non-limiting examples: yes/no, true/false, I/O, high/low, etc.). For example, a sequence rule can include instructions to identify whether an administration event immediately follows (or is the next event in the sequence) a dispense event. In this case, the resulting event array sequence parameter can include an indication of "yes," since the administration event is the next event following the dispense event. It will be understood that similar sequence rules can be applied to the event array(s) to generate various event array parameters. Further it will be understood that the event array sequence parameter can include various data, which can depend on the applied rule.

In some cases, an event array sequence parameter can be compared to one or more event array sequence thresholds to determine whether the event array sequence parameter satisfies the respective event array sequence threshold. In some cases, if the event array sequence parameter satisfies the event array sequence threshold, then the particular sequence of events taken by a provider can be considered normal, usual, acceptable, or the like. In contrast, in some cases, if the event array sequence parameter does not satisfy the event array sequence threshold, then the particular sequence of events taken by a provider can be considered abnormal, unusual, unacceptable, or the like.

As described herein, the event array sequence thresholds can come in many forms and can be based at least in part on the applied sequence rule. For example, if the event array parameter includes a binary output, as described above, then the event array parameter threshold can also include a binary output. For example, if the sequence rule includes instructions to identify whether an administration event immediately follows a dispense event, then the event array sequence threshold can be "yes." Accordingly, in this example, if the event array sequence parameter is "yes" then the event array parameter satisfies the event array parameter threshold. However, in this example, if the event array parameter is "no" then the event array parameter does not satisfy the event array parameter threshold.

As another example, the event array parameter threshold can include a string, a list, or other indication of the sequence of events. In cases such as these, the event array parameter can satisfy the event array parameter threshold if the event array parameter matches (e.g., includes the same a string, a list, or other indication of the sequence of events) the event array parameter threshold. In contrast, in some cases, the event array parameter does not satisfy the event array parameter threshold if the event array parameter does not match the event array parameter threshold.

In some cases the event array sequence threshold can correspond to a probability of a particular sequence occurring. For example, the verification system 402 can build, populate, or obtain a variable-length Markov model, which describes the probabilities of different sequences of actions occurring (for example, for a given medication), based on a set of data. For example, the system 402 can determine the probability of a first event in a sequence being a dispense event in a set of data, and the event sequence threshold can correspond to that probability. As another example, the system can determine how likely it is that a waste event is preceded by a dispensing event and/or an administration event. In some cases, the event array sequence thresholds can be generated using a set of event arrays, such as those event arrays associated with a particular provider, all providers, or a subset of providers, such as providers with a similar access level.

As a non-limiting example, probability data may indicate that a dispensing event is the first event in a sequence 88% of the time, and an administration event is the first event in a sequence only 11.5% of the time. Furthermore, the probability data may indicate that, following a dispense event as a first event, in 99.2% of cases, the next event is an administration event. If the sequence rule includes an instruction to identify whether a dispense event is the first event, and, if so, whether an administration event is the second event, then the event array parameter can include a binary indication, such as yes or no. Based on probability, if the dispense event is the first event, then an administration event can be expected to be the second event. Accordingly, in this case, the event array parameter can satisfy the event array parameter threshold if the event array parameter is yes. Otherwise, in some cases, the event array parameter does not satisfy the event array parameter threshold. Accordingly, in some cases, the sequence rules and/or the resulting event array parameters can be indicative of whether an individual deviated from the norm or was unusual as compared to others.

As described herein, in addition, to determining whether an individual event array satisfies the event array sequence threshold, the verification system 402 can track the number of event arrays associated with a user that do or do not satisfy the event array sequence threshold. This number can be compared with a sequence rule threshold to determine whether the provider satisfies a sequence rule threshold.

The verification system 402 can determine the sequence rule threshold based on individual event array sequence parameters of the event arrays of a set of data. For example, the verification system 402 can determine an average number of event arrays that satisfy the event array sequence threshold for individual users. A deviation or different from the average can then be used as the sequence rule threshold. If the average number of event arrays for a particular user satisfies the event array sequence threshold, the verification system 402 can identify the user as an abnormal user or otherwise indicate that the user does not satisfy the sequence rule threshold.

Dispensing Rules

In some cases, one or more dispensing rules can be applied to some or all event arrays to generate one or more event array dispensing parameters. In some embodiments, a dispensing rule can include instructions to identify whether one type of event follows another type of event, such as whether an administration event follows each dispensing event in the event array. The application of the dispensing rule (for example, the result of performing the instructions) can result in an event array dispensing parameter.

As a non-limiting example, an event array can include two events. From earliest in time to latest in time, the event array can include a dispensing event and a waste event (but no administration event). Accordingly, in this case, the event array dispensing parameter can include a binary output of "no." However, if the event array included a third event which corresponded to administration, then the event array dispensing parameter can include a binary output of "yes."

In some cases, the event array dispensing parameter can be compared to one or more event array dispensing thresholds to determine whether the event array parameter satisfies the respective event array dispensing threshold. In some cases, if the event array dispensing satisfies the event array dispensing threshold, then the event can be considered normal, usual, acceptable, or the like. In contrast, in some cases, if the event array dispensing parameter does not satisfy the event array dispensing threshold, then the event can be considered abnormal, unusual, unacceptable, or the like.

As described herein, the event array dispensing thresholds can come in many forms and can be based at least in part on the applied rule. For example, if the event array parameter includes a binary output, as described above, then the event array dispensing threshold can also include a binary output. For example, if the dispensing rule includes instructions to identify whether an administration event follows each dispensing event in the event array, then the event array parameter threshold can be "yes." Accordingly, if the event array parameter is "yes" then the event array parameter satisfies the event array parameter threshold. However, if the event array parameter is "no" then the event array parameter does not satisfy the event array parameter threshold.

As described above, in some cases, it can be unusual to dispense the drug without administering that drug to the patient. Accordingly, if the event array parameter does not satisfy the event array parameter threshold, then the system can identify the event array, or the provider as being associated with abnormal behavior, which may be the result of drug misuse.

As described herein, in addition, to determining whether an individual event array satisfies the event array dispensing threshold, the verification system 402 can track the number of event arrays associated with a user that do or do not satisfy the event array dispensing threshold. This number can be compared with a dispensing rule threshold to determine whether the provider satisfies a dispensing rule threshold.

The verification system 402 can determine dispensing rule threshold based on individual event array dispensing parameters of the event arrays of a set of data. For example, the verification system 402 can determine an average number of event arrays that satisfy the event array dispensing threshold for individual users. A deviation or different from the average can then be used as the dispensing rule threshold. If the average number of event arrays for a particular user satisfies the event array dispensing threshold, the verification system 402 can identify the user as an abnormal user or otherwise indicate that the user does not satisfy the dispensing rule threshold.

Omission Rules

In some cases, one or more omission rules can be applied to some or all event arrays to generate one or more event array parameters. An omission rule can include instructions to identify whether the following equation is satisfied:

$$\text{Dispensed Amount} = \text{Administered Amount} + \text{Wasted Amount} + \text{Returned Amount} \quad \text{(Equation 1)}$$

where, when considering all events of a particular event array, "dispensed" is the total amount of a particular medication that was dispensed (for example, from the dispensing system 404) for a particular patient, "administered" is the total amount of the particular medication that was identified as administered to the particular patient (for example, by the administration system 408), "wasted" is the total amount of the particular medication that was identified as discarded (for example, by the dispensing system 404), and "returned" is the total amount of the particular medication that was identified as returned (for example, by the dispensing system 404).

In some embodiments, the application of the omission rule (for example, the result of performing the instructions) can result in the event array parameter. As a non-limiting example, if 20 mL of Diprivan is dispensed for Patient A, but only 15 mL of Diprivan is administered to Patient A, and no Diprivan is wasted or returned, then the system can identify that Equation 1 is not satisfied because 5 mL of Diprivan is not accounted for. Accordingly, in this case, the event array parameter can include a binary output of "no." In some cases, as described herein, event arrays in which at least some of the medication is not accounted for (that is, the group of entries does not satisfy Equation 1), can be classified as discrepancies. However, if the event array included a fourth event which corresponded to a return event of 5 mL of Diprivan, then the event array parameter can include a binary output of "yes."

In some embodiments, the event array parameter and event array parameter threshold can be values. For example, the event array parameter threshold can be zero indicating that the difference between the amount dispensed and the combination of the amount administered, returned and wasted is to be zero. In certain cases, the event array parameter threshold can be non-zero, such as one or two indicating that the difference between the amount dispensed and the combination of the amount administered, returned and wasted should be less than one or two.

In some cases, the event array parameter can be compared to one or more event array parameter thresholds to determine whether the event array parameter satisfies the respective event array parameter threshold. In some cases, if the event array parameter satisfies the event array threshold, then the events taken by a provider can be considered normal, usual, acceptable, or the like. In contrast, in some cases, if the event array parameter does not satisfy the event array threshold, then the events taken by a provider can be considered abnormal, unusual, unacceptable, or the like.

As described herein, the event array parameter thresholds can come in many forms, and can be based at least in part on the applied rule. For example, if the event array parameter includes a binary output, as described above, then the event array parameter threshold can also include the binary output. For example, if the omission rule includes instructions to identify whether Equation 1 is satisfied, then the event array parameter threshold can be "yes." Accordingly, if the event array parameter is "yes" then the event array parameter satisfies the event array parameter threshold. However, if the event array parameter is "no" then the event array parameter does not satisfy the event array parameter threshold.

As described herein, in addition to determining whether an individual event array satisfies the event array omission threshold, the verification system 402 can track the number of event arrays associated with a user that do or do not satisfy the event array omission threshold. This number can be compared with an omission rule threshold to determine whether the provider satisfies an omission rule threshold.

The verification system 402 can determine the omission rule threshold based on individual event array omission parameters of the event arrays of a set of data. For example, the verification system 402 can determine an average number of event arrays that satisfy the event array omission threshold for individual users. A deviation or difference from the average can then be used as the omission rule threshold. If the average number of event arrays for a particular user satisfies the event array omission threshold, the verification system 402 can identify the user as an abnormal user or otherwise indicate that the user does not satisfy the omission rule threshold. For example, for a set of data, if the average number of event arrays for each user that satisfy the event array omission threshold is three with an event array omission threshold of ±2 from the average, and one user has six event arrays that satisfy the event array omission threshold, then the verification system 402 can determine that the user does not satisfy the omission rule threshold, and indicate the same to a user of the verification system 402.

Timing Rules

In some cases, the duration over which a user has control of or is holding onto a drug can be indicative of drug diversion or drug misuse. Accordingly, in some cases, one or more timing rules can be applied to an event array to generate an event array timing parameter. A timing rule can include instructions to identify a duration between to two or more events of an event array, and the application of the timing rule (for example, the result of performing the instructions) can result in the event array timing parameter.

As a non-limiting example, an event array can include three events: a first event that occurred at 12:00 PM, a second event that occurred at 12:10 PM, and a third event that occurred at 1:05 PM. Here, the difference in time between the first and second events, is 10 minutes, the difference in time between the first and last events, is 1 hour 5 minutes, and the difference in time between the second and third events, is 55 minutes. Accordingly, in some cases, the event array timing parameter can include a numerical value, such as an indication of the difference in time between two events. In addition or alternatively, the event array timing parameter can include a binary output, such as yes or no. For example, a timing rule can include instructions to identify whether a duration between to two or more events of an event array is greater than or less than a predetermined value.

In some cases, the event array timing parameter can be compared to one or more event array timing thresholds to determine whether the event array timing parameter satisfies the respective event array timing threshold. In some cases, if the event array timing parameter satisfies the event array threshold, then the events taken by a provider can be considered normal, usual, acceptable, or the like. In contrast, in some cases, if the event array timing parameter does not satisfy the event array threshold, then the events taken by a provider can be considered abnormal, unusual, unacceptable, or the like.

As described herein, the event array timing thresholds can come in many forms and can be based at least in part on the applied rule. For example, if the event array timing parameter includes a binary output, as described above, then the event array timing threshold can also include the binary output. For example, if the timing rule includes instructions to identify whether a duration between to two or more events of an event array is greater or less than a predetermined value, the event array timing threshold can be "yes" or "no." In some cases, if the event array timing parameter is "yes," then the event array timing parameter satisfies the event array timing threshold. Similarly, in some cases, if the event array timing parameter is "no" then the event array timing parameter does not satisfy the event array timing threshold.

As another example, the event array timing threshold can include a number, such as a number of minutes or hours. In cases such as these, in some instances, the event array timing parameter can satisfy the event array timing threshold if the event array timing parameter is greater than the event array timing threshold. Alternatively, in some instances, the event array timing parameter can satisfy the event array timing threshold if the event array timing parameter is less than the event array timing threshold. Furthermore, as described herein, the event array timing threshold can be determined based on a set of event arrays. For example, the verification system 402 can determine an average time between two events of a set of event arrays, identify the average plus or minus a certain amount (predetermined amount, standard deviation, etc.) as the event array timing threshold, and compare the time between two events of a particular event array with the determined event array timing threshold.

As described herein, in addition to determining whether an individual event array satisfies the event array timing threshold, the verification system 402 can track the number of event arrays associated with a user that do or do not satisfy the event array timing threshold. This number can be compared with a timing rule threshold to determine whether the provider satisfies a timing rule threshold.

The verification system 402 can determine the timing rule threshold based on individual event array timing parameters of the event arrays of a set of data. For example, the verification system 402 can determine an average number of event arrays that satisfy the event array timing threshold for individual users. A deviation or different from the average can then be used as the timing rule threshold. If the average number of event arrays for a particular user satisfies the event array timing threshold, the verification system 402 can identify the user as an abnormal user or otherwise indicate that the user does not satisfy the timing rule threshold. For example, for a set of data, if the average time between two events is two minutes with a standard deviation of thirty seconds (timing rule threshold of ±1 minute from average) and a user's average time between the two events is twenty seconds or five minutes, then the verification system 402 can determine that the user does not satisfy the timing rule threshold, and indicate the same to a user of the verification system 402.

Drug Quantity Rules

In some cases, the amount of a drug dispensed by a user be indicative of drug misuse. Accordingly, in some cases, one or more drug quantity rules can be applied to an event array to generate an event array quantity parameter. A drug quantity rule can include instructions to identify various drug quantities corresponding to the event array, and the result of the application of the drug quantity rule (for example, the result of performing the instructions) is the event array parameter.

As a non-limiting example, an event array can include three events: a dispensing event of 30 mg is associated with Provider A, a dispensing event of 20 mg is associated with Provider B, an administration event of 20 mg is associated with Provider A, a return event of 10 mg is associated with Provider A, and a return event of 20 mg is associated with Provider B. In some cases, a drug quantity rule includes instructions to identify the total amount of drug that is dispensed by a particular provider. In this example, the Provider A dispensed 30 mg, while Provider B dispensed 20 mg. In some cases, a drug quantity rule includes instructions to identify the total amount of drug that is administered by a particular provider. In this example, the Provider administered 20 mg, while Provider B administered 0 mg. In some cases, a drug quantity rule includes instructions to identify the total amount of drug that is wasted by a particular provider. In this example, the Provider wasted 10 mg, while Provider B wasted 20 mg. In some cases, a drug quantity rule includes instructions to identify the total amount of drug that is returned by a particular provider. In this example, the Provider returned 0 mg, while Provider B returned 0 mg. Accordingly, in some cases, the event array quantity parameter can include a number or indication of an amount of a drug.

In addition or alternatively, a drug quantity rule can include instructions to identify whether a particular administrator has used (for example, dispensed, administered, discarded or returned) a threshold amount of a drug. In instances such as these, the event array quantity parameter can be a selection of a binary response (non-limiting examples: yes/no, true/false, I/O, high/low, etc.). For example, a drug quantity rule can include instructions to identify whether a provider has dispensed at least a threshold amount (for example, 15 mg) of a particular drug. In this case, the resulting event array quantity parameter or an analysis of both Provider A and Provider B can include an indication of "yes," since each dispensed greater than 15 mg. Similarly, a drug quantity rule can include instructions to identify whether a particular administrator has not used (for example, dispensed, administered, discarded or returned) a threshold amount of drug. In instances such as these, the event array quantity parameter can be a selection of a binary response (non-limiting examples: yes/no, true/false, I/O, high/low, etc.). For example, a drug quantity rule can include instructions to identify whether a provider has not dispensed at least a threshold amount (for example, 25 mg) of a particular drug. In this case, the resulting event array quantity parameter for an analysis Provider A can include an indication of "yes" since Provider A dispensed greater than 25 mg. However, the resulting event array quantity parameter for an analysis Provider B can include an indication of "no" since Provider B did not dispense greater than 25 mg. It will be understood that similar drug quantity rules can be applied to the event array(s) to generate various event array parameters. Further it will be understood that the event array quantity parameter can include various data, which can depend on the applied rule.

In some cases, the event array quantity parameter can be compared to one or more event array quantity thresholds to determine whether the event array quantity parameter satisfies the respective event array quantity threshold. In some cases, if the event array quantity parameter satisfies the event array threshold, then the events taken by a provider can be considered normal, usual, acceptable, or the like. In contrast, in some cases, if the event array quantity parameter does not satisfy the event array threshold, then the events taken by a provider can be considered abnormal, unusual, unacceptable, or the like.

The event array quantity thresholds can come in many forms and can be based at least in part on the applied rule. For example, if the event array quantity parameter can include a binary output, as described above, then the event array quantity threshold can also include the binary output. For example, if the drug quantity rule includes instructions to identify whether a provider has dispensed at least a threshold amount, then the event array quantity threshold can be "yes" or "no." If the event array quantity parameter is "yes," then the event array quantity parameter satisfies the event array quantity threshold. However, if the event array quantity parameter is "no" then the event array quantity parameter does not satisfy the event array quantity threshold.

As another example, the event array quantity threshold can include a number corresponding to an amount of a drug. In cases such as these, the event array quantity parameter can satisfy the event array quantity threshold if the event array quantity parameter matches or exceeds the event array quantity threshold. Alternatively, the event array quantity parameter can satisfy the event array quantity threshold if the event array quantity parameter matches or is below the event array quantity threshold.

The event array quantity thresholds can be determined using various methods. For example, in some cases, the event array quantity thresholds are based at least in part on other individuals, such as individuals and a peer group. For example, in some cases, the event array quantity thresholds can correspond to a median, average, or total amount of a drug dispensed, administered, wasted, and/or returned by one or more other providers.

As described herein, in addition to determining whether an individual event array satisfies the event array quantity threshold, the verification system 402 can track the number of event arrays associated with a user that do or do not satisfy the event array quantity threshold or the average quantity of the individual users. This number can be compared with a quantity rule threshold to determine whether the provider satisfies a quantity rule threshold.

The verification system 402 can determine the quantity rule threshold based on individual event array quantity parameters of the event arrays of a set of data. For example, the verification system 402 can determine an average number of event arrays that satisfy the event array quantity threshold for individual users or the average quantity for individual users. A deviation or different from the average can then be used as the quantity rule threshold. If the average quantity or average number of event arrays for a particular user satisfies the event array quantity threshold, the verification system 402 can identify the user as an abnormal user or otherwise indicate that the user does not satisfy the quantity rule threshold. For example, for a set of data, if the average quantity for dispensing morphine is ml and the quantity rule threshold is ±5 ml, and a user's average dispense of morphine is ml, then the verification system 402 can determine that the user does not satisfy the quantity rule threshold, and indicate the same to a user of the verification system 402.

Location Rules

In some cases, a location associated with an event can be indicative of drug misuse. Accordingly, in some cases, one or more location rules can be applied to an event array to generate an event array parameter. A location rule can include instructions to identify various locations corresponding to the event array, and the result of the application of the location rule (for example, the result of performing the instructions) is the event array parameter.

As a non-limiting example, an event array can include two events: an event at Location A and associated with Provider A, and an event at Location B and associated with Provider A. In some cases, a location rule includes instructions to identify where a location associated with an event. In this example, a first event is associated with Location A and a second event is associated with Location B. Accordingly, in some cases, the event array location parameter can include an indication of the location. In some embodiments, the event array location parameter and event array location threshold can be values.

In some cases, the event array location parameter can be compared to one or more event array location thresholds to determine whether the event array location parameter satisfies the respective event array location threshold. In some cases, if the event array location parameter satisfies the event array location threshold, then the events taken by a provider can be considered normal, usual, acceptable, or the like. In contrast, in some cases, if the event array location parameter does not satisfy the event array location threshold, then the events taken by a provider can be considered abnormal, unusual, unacceptable, or the like.

The event array location threshold can include a location zone, such as a region on a map. In cases such as these, the event array location parameter can satisfy the event array location threshold if the event array location parameter (e.g., the location) is located within the location zone. Alternatively, the event array location parameter can satisfy the event array location threshold if the event array location parameter matches the event array location threshold.

Figure 13:
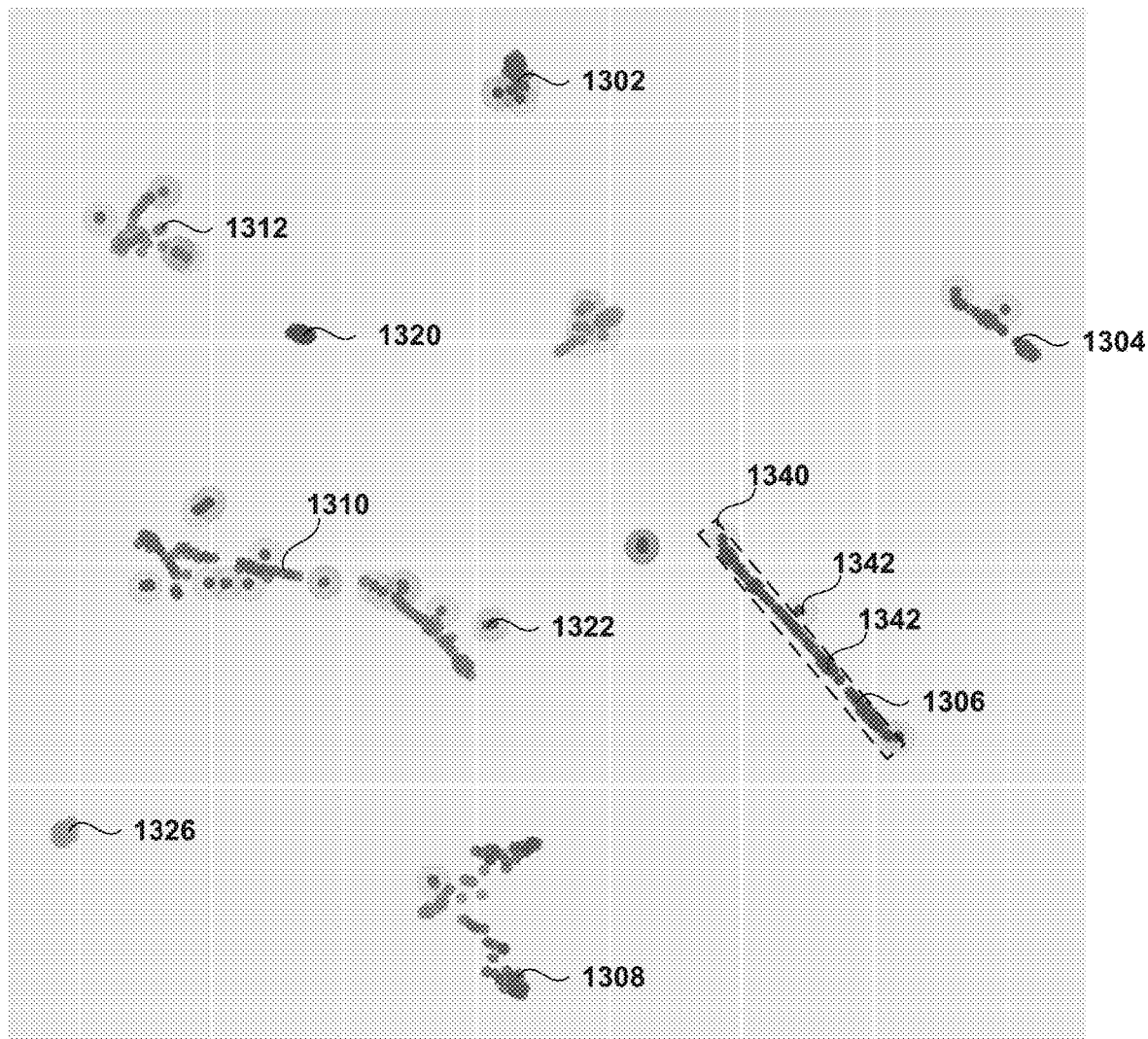
FIG. 13 illustrates an example hospital floor map indicative of an example clustering of providers into their respective care areas.

FIG. 13 illustrates an example hospital floor map indicative of an example clustering of providers into their respective care areas. In this illustration, each point on the map indicates a location of an event performed by providers. Accordingly, the various clusters 1302, 1304, 1306, 1308, 1310, and 1312 illustrate the popular or typical regions or areas that providers perform the events.

In some cases, an event array location threshold can correspond to a region on the map, such as a typical region that events are performed. As a non-limiting example, the event array location threshold can correspond to region 1340. Accordingly, in this case, if the event array location parameter (e.g., the location of the event) is associated with point 1342, then the event array location parameter does not satisfy the event array location threshold. That is because point 1342 does not fall within region 1340. However, if the event array location parameter is associated with point 1344, then the event array location parameter does satisfy the event array location threshold. That is because point 1342 falls within region 1340.

As described herein, in addition to determining whether an individual event array satisfies the event array location threshold, the verification system 402 can track the number of event arrays associated with a user that do or do not satisfy the event array location threshold. This number can be compared with a location rule threshold to determine whether the provider satisfies a location rule threshold.

The verification system 402 can determine the location rule threshold based on individual event array location parameters of the event arrays of a set of data. For example, the verification system 402 can determine an average number of event arrays that satisfy the event array location threshold for individual users. A deviation or different from the average can then be used as the location rule threshold. If the average number of event arrays for a particular user satisfies the event array location threshold, the verification system 402 can identify the user as an abnormal user or otherwise indicate that the user does not satisfy the location rule threshold. For example, for a set of data, if the average number of event arrays that satisfy the location threshold for individual users is two and the location rule threshold is >3, and a user's number of event arrays that satisfy the location threshold is five, then the verification system 402 can determine that the user does not satisfy the location rule threshold, and indicate the same to a user of the verification system 402.

Witness Rules

In some cases, a pattern of working with another provider to perform a waste event can be indicative of drug misuse. Accordingly, in some cases, one or more witness rules can be applied to an event array to generate an event array parameter. A witness rule can include instructions to identify providers (e.g., performer of the event and the witness) associated with event array, and the result of the application of the witness rule (for example, the result of performing the instructions) is the event array parameter.

As a non-limiting example, an event array can include two events: an event associated with provider A and witness B, and an event associated with provider A and witness C. In some cases, a witness rule includes instructions to identify the witness and/or provider associated with a dispensing event. Accordingly, in some cases, the event array witness parameter can include an indication of the witness, the provider, or a combination thereof.

In some cases, a witness rule includes instructions to identify how many times a particular group of providers worked together (e.g., as performer and witness) to waste a drug. Accordingly, in some cases, the event array witness parameter can include a value.

In some cases, the event array witness parameter can be compared to one or more event array witness thresholds to determine whether the event array witness parameter satisfies the respective event array witness threshold. In some cases, if the event array witness parameter satisfies the event array threshold, then the events taken by a provider can be considered normal, usual, acceptable, or the like. In contrast, in some cases, if the event array witness parameter does not satisfy the event array threshold, then the events taken by a provider can be considered abnormal, unusual, unacceptable, or the like.

The event array witness thresholds can come in many forms and can be based at least in part on the applied rule. For example, if the witness rule includes instructions to identify the witness and/or provider pair, then the event array witness threshold can, for example, be a string of their names. If the event array witness parameter matches the string, then the event array witness parameter satisfies the event array witness threshold. However, if the event array witness parameter does not match the string, then the event array witness parameter does not satisfy the event array witness threshold.

As another example, if the witness rule includes instructions to identify how many times, over a given period, that a particular pair or group of providers worked to waste a drug, then the event array witness threshold can be a value. In some cases, if the event array witness parameter is greater than or equal to that value, then the event array witness parameter satisfies the event array witness threshold. In some cases, if the event array witness parameter is less than or equal to that value, then the event array witness parameter satisfies the event array witness threshold.

As described herein, in addition to determining whether an individual event array satisfies the event array witness threshold, the verification system 402 can track the number of event arrays associated with a user that do or do not satisfy the event array witness threshold or monitor the event arrays associated with the user to identify patterns of witnesses or groups of users that frequently waste together. This number can be compared with a witness rule threshold to determine whether the provider satisfies a witness rule threshold.

The verification system 402 can determine the witness rule threshold based on individual event array witness parameters of the event arrays of a set of data. For example, the verification system 402 can determine an average number of different witnesses for individual users. A deviation or different from the average can then be used as the witness rule threshold. If the average number of event arrays for a particular user satisfies the event array witness threshold, the verification system 402 can identify the user as an abnormal user or otherwise indicate that the user does not satisfy the witness rule threshold. For example, for a set of data, if the average number of witnesses for individual users is twelve and the witness rule threshold is ±4, and a user's number of witnesses is two, then the verification system 402 can determine that the user does not satisfy the witness rule threshold, and indicate the same to a user of the verification system 402.

Behavior Rules

In some cases, a changing behavioral pattern can be indicative of drug misuse. Accordingly, in some cases, one or more behavioral rules can be applied to an event array to generate an event array behavior parameter. A behavioral rule can include instructions to identify a provider's behavior over a period time, and the application of the behavioral rule (for example, the result of performing the instructions) can result in the event array behavior parameter.

As a non-limiting example, a behavioral rule can include instructions to identify, based on a plurality of events or event arrays, patterns of behavior of a particular user and determine whether the patterns have changed. The patterns can include, but are not limited to, the amount that the provider generally dispenses, wastes, administers, or returns, the typical location at which the provider typically dispenses, administers, wastes, etc., who the provider typically works with (for example, as a witness to waste events), the typical sequence of events performed by the provider, the amount of time between events, etc. In some cases, these determinations can be made based on averages or totals.

To identify the patterns of behavior, the verification system 402 can analyze a set of data that includes multiple event arrays associated with a user over time. From the set of data, the verification system 402 can determine a variety of event array parameters, such as, but not limited to, average time between events, identification of witnesses, average amount dispensed for different drugs, typical sequence of events, typical locations for dispensing, administering, etc.

In addition, the verification system 402 can determine the various event array parameters for different portions of the set of data. For example, the verification system 402 can break up the set of data into subsets of data, determine the event array parameters for the subsets of data, and compare the event array parameters between the subsets of data or with the event array parameters of the set of data.

In some cases, the verification system 402 can generate the subsets of data based on time. For example, if the verification system 402 breaks up the set of data in to four groups, the first group can be the earliest in time event arrays. The second group can be the second earliest in time event arrays, the third group can be the third earliest in time event arrays, and the fourth group can include the last in time event arrays.

The event array parameter of the different groups can be compared to identify deviations between the groups. For example, the event array parameters for the set of data as a whole can be used as an average or the event array parameters of the different groups of the set of data can be used to determine averages for the event array parameters. The event array parameter thresholds can be determined as a deviation or difference from the averages. As such, the event array parameter thresholds can be compared with the event array parameters of the different groups to identify groups that do not satisfy the event array parameter thresholds.

In some cases, the system can determine the event array parameters for the set of data and then compared the determined event array parameters with future sets of data associated with a user. For example, the verification system 402 can determine the average time between events for a user based on weeks of data. The average time between events can then be compared with the amount of time between events of new event arrays to identify changes, etc.

Rules Scores and Overall Scores

In some cases, the verification system 402 can generate a score associated with whether an event array parameter satisfies an event array parameter threshold. For example, the score can be indicative of a number of times (for example, a number of events) in which a particular provider is associated with an event array parameter that does not satisfy the event array parameter threshold. For example, the score can be the total of number of times that the event array parameter that does not satisfy the event array parameter threshold. In some cases, the total of number of times that the event array parameter that does not satisfy the event array parameter threshold can be plotted relative to others, and outlier scores can be created in such a way that they are exponentially distributed, and are then standardized by the mean of the outlier scores. In some cases, the score value (for example, 5) can indicate that, over a specific time-period (configurable by a user), the associated provider has 5 times more, 5 times less, 5 more, 5 less, etc. that a normal provider. In some cases, the normal provider can be determined using similar rules for all or s subset of providers, exponentially distributing the data, and are then standardizing by the mean of the outlier scores.

In some cases, applying the rules to the event arrays can allow the system to identify behavior patterns, trends, or other anomalous usage information to identify particular providers suspected as a high risk drug diversion. Moreover, in some cases, the system can be configured to determine or present actionable recommendations, which can further help to minimize risk of future diversions.

In some implementations, the verification system 402 can determine an overall score, which can be indicative of a particular provider's diversion risk. For example, in some cases, the overall score can be a function of one or more of the scores associated with the applied rules, as described above. For example, the overall score can be an average, median, total, etc. of one or more scores. Alternatively, the system can weight one or more of the scores differently from other scores, and the overall score can be determined based off of the weighted scores. In some cases, the overall score can provide a holistic overview of a single provider/nurse across multiple metrics, and providers/nurses can be easily compared with one-another. Furthermore, by utilizing multiple metrics, the system can highlight the problem areas of each provider/nurse.

Figures 14A, 14B:
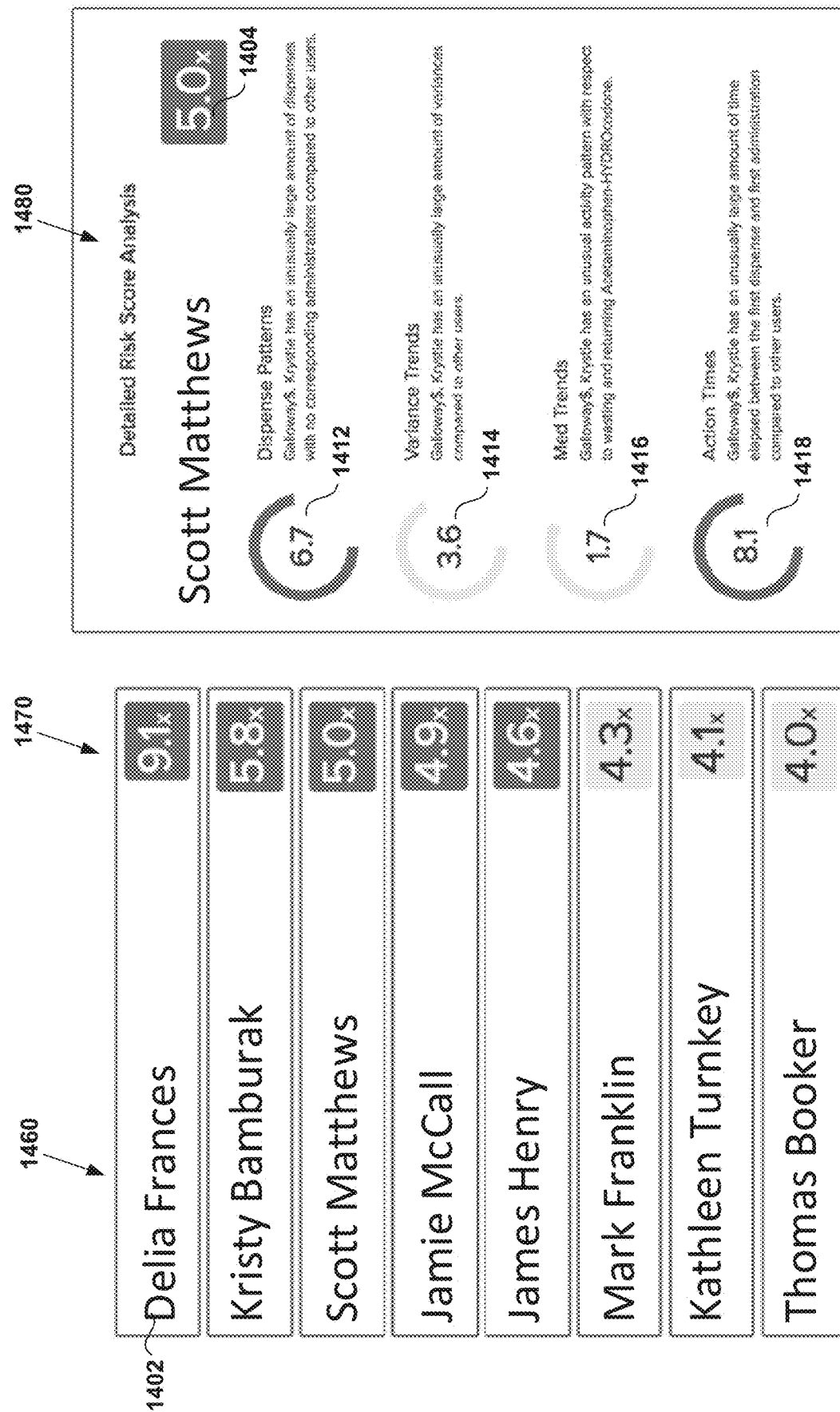
FIGS. 14A-14B illustrate example graphical user interfaces (GUIs) displaying various metrics associated with a risk of drug diversion, according to some embodiments.

FIGS. 14A-14B illustrate example graphical user interfaces (GUIs) displaying various metrics associated with a risk of drug diversion, according to some embodiments. FIG. 14A includes a ranked list of providers/nurse 1460, ordered from most unusual/risky to least, based on the overall score of each provider. As illustrated from FIG. 14A, the presentation of the overall score 1470 for each provider can allow a viewer to quickly identify a risk of diversion associated with the listed providers.

In some cases, each overall score 1470 can indicate a difference as compared to normal behavior (described in more detail below). For example, in FIG. 14A, *Delia* Frances 1402 is listed with a score of 9.1. In some cases, the overall score of 9.1 can indicate that, over a specific time-period (configurable by a user), *Delia* Frances is 9.1 more times more likely to be a drug diverter than her peers. In other words, the overall score can indicate who, if anyone, is at risk of drug diversion.

FIG. 14B illustrates a detailed risk score analysis 1480 of Scott Matthews. As illustrated, several of the metrics used to generate Scott's overall score 1404 of 5.0 are shown. For example, Scott has a "dispense patterns" score (1412) of 6.7. In some cases, the dispense patterns score can correspond to the dispensing rules, as described above. Further, Scott has a "variance trends" score (1414) of 3.6. In some cases, the variance trends score can correspond to the omission rules, as described above. Further, Scott has a "med trends" score (1416) of 1.7. In some cases, the med trends score can correspond to the sequence rules, as described above. Further, Scott has an "action times" score (1418) of 8.1. In some cases, the action times score can correspond to the timing rules, as described above.

While Scott's overall score (5.0) provides a holistic overview of Scott's drug diversion risk to the medical facility, the other metrics explain or define Scott's particular problem areas. Specifically, in this example, Scott has a very high Dispense Patterns and Action Times score. In some cases, as illustrated in FIG. 14B, the system is configured to display natural language in addition to each metric. Accordingly, medical facility personnel can see the metric, and can also understand the reasoning and why a provider/nurse is considered risky/unusual.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (e.g., not all are necessary for the practice of the algorithms). Moreover, in certain embodiments, operations, acts, functions, or events can be performed concurrently, e.g., through multi-threaded processing, interrupt processing, or multiple processors or processor cores or on other parallel architectures, rather than sequentially.

Systems and modules described herein may comprise software, firmware, hardware, or any combination(s) of software, firmware, or hardware suitable for the purposes described herein. Software and other modules may reside and execute on servers, workstations, personal computers, computerized tablets, PDAs, and other computing devices suitable for the purposes described herein. Software and other modules may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, interactive voice response, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data storage devices shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, specially-equipped computer (e.g., comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks.

These computer program instructions may also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computing device or other programmable data processing apparatus to cause a series of operations to be performed on the computing device or other programmable apparatus to produce a computer implemented process such that the instructions which execute on the computer or other programmable apparatus provide steps for implementing the acts specified in the flow chart and/or block diagram block or blocks.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application, in either this application or in a continuing application.

What is claimed is:

1. A method, comprising:
   receiving, over a network, a first plurality of events from a first system, wherein the first system generates the first plurality of events in response to user interactions with the first system;
   receiving, over the network, a second plurality of events from a second system, wherein the second system generates the second plurality of events in response to user interactions with the second system, wherein each event of the first plurality of events and the second plurality of events comprises a plurality of event parameters, wherein a first format of the first plurality of events is different from and not compatible with a second format of the second plurality of events;
   normalizing the first plurality of events to generate a normalized first plurality of events in a normalized format;
   normalizing the second plurality of events to generate a normalized second plurality of events in the normalized format;
   concurrently generating a plurality of event arrays, at least one event array of the plurality of event arrays comprising a plurality of normalized events that occurred within a particular window of time and that include at least one matching event parameter, the plurality of normalized events including at least a first normalized event corresponding to an event of the normalized first plurality of events and a second normalized event corresponding to an event of the normalized second plurality of events;
   generating at least one event array parameter based on the at least one event array;
   determining that the at least one event array parameter satisfies an event array parameter threshold; and
   based on the determining that the at least one event array parameter satisfies the event array parameter threshold, generating an indication of a potential drug diversion event.

2. The method of claim 1, wherein receiving, over the network, the first plurality of events from the first system and the second plurality of events from the second system occurs responsive to a user command.

3. The method of claim 1, wherein receiving, over the network, the first plurality of events from the first system and the second plurality of events from the second system occurs at predetermined intervals of time.

4. The method of claim 1, wherein receiving, over the network, the first plurality of events from the first system and the second plurality of events from the second system comprises receiving the first plurality of events at a first time and receiving the second plurality of events at a second time that is different from the first time.

5. The method of claim 1, wherein the normalized first plurality of events and the normalized second plurality of events comprise same event parameter fields.

6. The method of claim 1, wherein the normalizing the first plurality of events and the second plurality of events comprises:
   identifying event parameters from the plurality of event parameters of the first plurality of events and the second plurality of events for inclusion in the normalized first plurality of events and the normalized second plurality of events; and
   discarding event parameters of the first plurality of events and the second plurality of events that are not identified for inclusion in the normalized first plurality of events and the normalized second plurality of events.

7. The method of claim 1, wherein the normalizing the first plurality of events and the second plurality of events comprises:
   comparing event parameters of the first plurality of events and event parameters of the second plurality of events to identify an event of the first plurality of events that matches an event of the second plurality of events; and
   discarding the event of the first plurality of events that matches the event of the second plurality of events.

8. The method of claim 1, wherein generating the at least one event array parameter comprises applying a sequence determination rule to identify a sequence of events in the at least one event array, wherein the at least one event array parameter comprises the sequence of events.

9. The method of claim 1, wherein generating the at least one event array parameter comprises applying a timing rule to identify a duration between two or more events of the at least one event array.

10. The method of claim 1, wherein the event array parameter threshold is based at least in part on an average calculated from a set of event arrays.

11. The method of claim 10, wherein determining that the at least one event array parameter satisfies the event array parameter threshold comprises determining that the at least one event array parameter satisfies a determined variance from the average.

12. The method of claim 1, wherein the first plurality of events comprises an obfuscation identifier that is indicative of a manner in which information was abstracted in the first plurality of events by the first system, wherein normalizing the first plurality of events comprises un-abstracting the information in the first plurality of events using the obfuscation identifier.

13. The method of claim 1, wherein normalizing the first plurality of events and the second plurality of events comprises identifying one or more additional event parameters corresponding to the plurality of event parameters.

14. The method of claim 1, wherein generating the indication of the potential drug diversion event comprises generating at least one score based on comparing the at least one event array parameter to the event array parameter threshold, and wherein the method further comprises causing a display to display an indication of the at least one score.

15. The method of claim 14, wherein the at least one event array parameter comprises a plurality of event array parameters, wherein the at least one event array parameter threshold comprises a plurality of event array parameter thresholds, and wherein the at least one score comprises a score for each comparison of an event array parameter of the plurality of event array parameters and a respective event array parameter threshold of the plurality of event array parameter thresholds.

16. The method of claim 1, wherein concurrently generating the plurality of event arrays comprises:
identifying a set of normalized events that include the at least one matching event parameter, the set of normalized events including one or more first normalized events of the normalized first plurality of events and one or more second normalized events of the normalized second plurality of events; and
identifying the plurality of normalized events that occurred within the particular window of time from the set of normalized events to generate the at least one event array.

17. The method of claim 16, wherein each of the plurality of event arrays comprises a single set of related events.

18. The method of claim 16, wherein the plurality of normalized events of a particular event array of the plurality of event arrays are different from the plurality of normalized events of all other event arrays of the plurality of event arrays.

19. A system, comprising:
one or more processors configured to:
receive, over a network, a first plurality of events from a first system, wherein the first system generates the first plurality of events in response to user interactions with the first system;
receive, over the network, a second plurality of events from a second system, wherein the second system generates the second plurality of events in response to user interactions with the second system, wherein each event of the first plurality of events and the second plurality of events comprises a plurality of event parameters, wherein a first format of the first plurality of events is different from and not compatible with a second format of the second plurality of events;
normalize the first plurality of events to generate a normalized first plurality of events in a normalized format;
normalize the second plurality of events to generate a normalized second plurality of events in the normalized format;
concurrently generate a plurality of event arrays, at least one event array of the plurality of event arrays comprising a plurality of normalized events that occurred within a particular window of time and that include at least one matching event parameter, the plurality of normalized events including at least a first normalized event corresponding to an event of the normalized first plurality of events and a second normalized event corresponding to an event of the normalized second plurality of events;
generate at least one event array parameter;
determine that the at least one event array parameter satisfies an event array parameter threshold; and
based on the determination that the at least one event array parameter satisfies the event array parameter threshold, generate an indication of a potential drug diversion event.

20. Non-transitory computer-readable media comprising computer-executable instructions that, when executed by a computing system for determining event discrepancies between data sets from distributed systems, cause the computing system to:
receive, over a network, a first plurality of events from a first system, wherein the first system generates the first plurality of events in response to user interactions with the first system;
receive, over the network, a second plurality of events from a second system, wherein the second system generates the second plurality of events in response to user interactions with the second system, wherein each event of the first plurality of events and the second plurality of events comprises a plurality of event parameters, wherein a first format of the first plurality of events is different from and not compatible with a second format of the second plurality of events;
normalize the first plurality of events to generate a normalized first plurality of events in a normalized format;
normalize the second plurality of events to generate a normalized second plurality of events in the normalized format;
concurrently generate a plurality of event arrays, at least one event array of the plurality of event arrays comprising a plurality of normalized events that occurred within a particular window of time and that include at least one matching event parameter, the plurality of normalized events including at least a first normalized event corresponding to an event of the normalized first plurality of events and a second normalized event corresponding to an event of the normalized second plurality of events;
generate at least one event array parameter;
determine that the at least one event array parameter satisfies an event array parameter threshold; and
based on the determination that the at least one event array parameter satisfies the event array parameter threshold, generate an indication of a potential drug diversion event.

* * * * *